United States Patent
Hayden et al.

(10) Patent No.: US 7,696,151 B2
(45) Date of Patent: *Apr. 13, 2010

(54) METHODS AND COMPOSITIONS USING STEAROYL-COA DESATURASE TO IDENTIFY TRIGLYCERIDE REDUCING THERAPEUTIC AGENTS

(75) Inventors: Michael R. Hayden, Vancouver (CA); Alison J. Brownlie, Vancouver (CA); James M. Ntambi, Madison, WI (US); Makoto Miyazaki, Madison, WI (US); Mark P. Gray-Keller, Middleton, WI (US); Alan D. Attie, Madison, WI (US)

(73) Assignees: Xenon Pharmaceuticals Inc., Burnaby (CA); Wisconsin Alumni Research Foundation, Madison, WI (US)

( * ) Notice: Subject to any disclaimer, the term of this patent is extended or adjusted under 35 U.S.C. 154(b) by 692 days.

This patent is subject to a terminal disclaimer.

(21) Appl. No.: 11/178,808

(22) Filed: Jul. 11, 2005

(65) Prior Publication Data
US 2005/0256033 A1    Nov. 17, 2005

Related U.S. Application Data

(62) Division of application No. 09/792,468, filed on Feb. 23, 2001, now Pat. No. 6,987,001.

(60) Provisional application No. 60/184,526, filed on Feb. 24, 2000, provisional application No. 60/221,697, filed on Jul. 31, 2000, provisional application No. 60/255,771, filed on Dec. 15, 2000.

(51) Int. Cl.
*G01N 33/53* (2006.01)
*A61K 38/00* (2006.01)
*A61K 31/20* (2006.01)

(52) U.S. Cl. ............................... 514/2; 435/4; 435/7.1; 435/7.21; 435/7.71; 435/325; 514/560

(58) Field of Classification Search .................... 435/4, 435/7.1, 7.21, 7.71, 325; 514/2, 560
See application file for complete search history.

(56) References Cited

U.S. PATENT DOCUMENTS

| | | | |
|---|---|---|---|
| 4,696,916 A | | 9/1987 | Yabushita et al. |
| 5,336,496 A | * | 8/1994 | Akimoto et al. .............. 514/464 |
| 5,443,974 A | * | 8/1995 | Hitz et al. ..................... 800/264 |
| 5,554,646 A | | 9/1996 | Cook et al. |
| 5,702,902 A | | 12/1997 | Tartaglia |
| 6,162,455 A | | 12/2000 | Cleale |
| 6,288,114 B1 | | 9/2001 | Bauman et al. |
| 2003/0064950 A1 | | 4/2003 | Ntambi et al. |

FOREIGN PATENT DOCUMENTS

| EP | 87301257.9 | 2/1987 |
|---|---|---|
| GB | 9108234.6 | 8/1990 |
| WO | WO 96/05861 | 2/1996 |
| WO | WO 99/63979 | 12/1999 |
| WO | WO 00/09754 | 2/2000 |

OTHER PUBLICATIONS

Jeffcoat et al. 1977.Studies on the Inhibition of the Desaturases by Cyclopropenoid Fatty Acids, Lipids, vol. 12, pp. 480-485.*
Shimizu et al., Lipids, vol. 26, pp. 512-516 (1991).
Seifried and Gaylor, J. Biol. Chem. vol. 251, pp. 7468-7473 (1976).
Talamo and Bloch, Analytical Biochemistry, vol. 29, pp. 300-304 (1969).
Clarke et al., Prog. Lipid Res., 32, 139-149 (1993).
Kim et al., J. Lipid Res., 41, 1310-1316 (2000).
Skrede et al., Biochim. Biophys. Acta, 1344, 115-131 (1997).
Li et al., Int.J. Cancer, 57, 348-352 (1994).
Miyazaki et al., J. Biol. Chem., 275, 30132-30138 (2000).
Paisley et al., J. Nutr., 126, 2730-2737 (1996).
Waters et al., J. Biol. Chem., 269, 27773-27777 (1994).
Choi, et al., "The trans-10, cis-12 Isomer of Conjugated Linoleic Acid Downregulates Stearoyl-CoA Desaturase 1 Gene Expression in 3T3-L1 Adipocytes," J. Nutrition, vol. 130, pp. 1920-1924 (2000).
Zoeller, et al., "The importance of the stearoyl-CoA desaturase system in octadecenoate metabolism in the Morris hepatona7288C," Biochim. Biophys. Acta, vol. 845, pp. 380-388 (1985).
Bretillon, et al., "Effects of Conjugated Linoleic Acid Isomers on the Hepatic Microsomal Desaturation Activities in Vitro," Lipids, vol. 24, No. 9, pp. 965-969 (1999).
Hovik, et al., "Thia fatty acids as substrates and inhibitors of stearoyl-CoA desaturase," Biochim. Biophys. Acta, vol. 845, pp. 251-256 (1997).
Khoo, et al., "Manipulation of body fat composition with sterculic acid can inhibit mammary carcinomas in vivo," British J. Cancer, vol. 63, pp. 97-101 (1991).
Cao, et al., "Inhibition of fatty acid Δ6- and Δ5-desaturation by cyclopropene fatty acids in rat liver microsomes," Biochim. Biophys. Acta, vol. 1210, pp. 27-34 (1993).
Park, et al., "Inhibition of hepatic stearoyl-CoA desaturase activity by trans-10, cis-12 conjugated linoleic acid and its derivatives," Biochim. Biophys. Acta, vol. 1486, pp. 285-292 (2000).
de Antueno, et al., "Relationship Between Mouse liver Δ9 Desaturase Activity," Lipids, vol. 28, No. 4 (1993).
Legrand, et al., "Inhibiting Δ9-Desaturase Activity Impairs Triacylglycerol Secretion in Cultured Chicken Hepatocytes" J. Nutrition, vol. 127, pp. 249-256 (1997).
Grinari, et al., "Conjugated Linoleic Acid is Synthesized Endogenously in Lactating Dairy Cows by Δ9-Desaturase," J. Nutrition, vol. 130, pp. 2285-2291, (2000).

(Continued)

*Primary Examiner*—Jon P Weber
*Assistant Examiner*—Kailash C Srivastava
(74) *Attorney, Agent, or Firm*—Elliot M. Olstein; Alan J. Grant

(57) ABSTRACT

The use of screening assays based on the role of human stearoyl-CoA desaturase-1 ("hSCD1") in human diseases, disorders or conditions relating to serum levels of triglyceride, VLDL, HDL, LDL, total cholesterol, or production of secretions from mucous membranes, monounsaturated fatty acids, wax esters, and the like, is disclosed. Also disclosed are conventions useful in the prevention and/or treatment of such diseases.

8 Claims, 21 Drawing Sheets

OTHER PUBLICATIONS

Jeffcoat, et al., "Studies on the Inhibition of the Desaturases by Cyclopropenoid Fatty Acids," Lipids, vol. 12, pp. 480-485 (1977).

Jeffcoat, et al., "Interrelationship between the Dietary Regulation of Fatty Acid Synthesis and the Fatty Acyl-CoA Desaturases," Lipids, vol. 12, pp. 469-474 (1977).

Kaestner, et al., "Differentiation-induced Gene Expression in 3T3-L1 Preadipocytes," Journal of Biological Chemistry, vol. 264, No. 25, pp. 14755-14761 (1991).

Ntambi, "Scd1 is expressed in sebaceous glands and is disrupted in the asebia mouse," Nature Genetics, vol. 23, p. 268 (1999).

Ntambi, "Regulation of stearoyl-CoA desaturase by polyunsaturated fatty acids and cholesterol," Journal of Lipid Research, vol. 40, pp. 1549-1558 (1999).

Legrand, et al., "Hepatic Δ9 desaturation and plasma VLDL level in genetically lean and fat chickens," International Journal of Obesity, vol. 16, pp. 289-294 (1992).

Legrand, et al., "Stearoyl-CoA Desaturase Activity in Primary Culture of Chicken Hepatocytes. Influence of Insulin, Glucocorticoid, Fatty Acids and Cordycepin," Int'l. J. Biochem, vol. 26, No. 6, pp. 777-785 (1994).

Lefevre, et al., "Hormonal Regulation of Stearoyl Coenzyme-A Desaturase 1 Activity and Gene Expression in Primary Cultures of Chiken Hepatocytes," Archives of Biochemistry and Biophysics, vol. 368, No. 2, pp. 329-337 (Aug. 15, 1999).

Legrand, et al., Effect of Insulin on Triacylglycerol Synthesis and Secretion by Chicken Hepatocyts in Primary Culture, Int'l. J. Biochem Cell Bio., vol. 28, No. 4, pp. 431-440 (1996).

Li, et al., "Partial Characterization of a cDNA for Human Stearoyl-CoA Desaturase and Changes in its mRNA Expression in Some Normal and Malignant Tissues," Int'l. J. Cancer, vol. 57, pp. 348-352 (1994).

Waters et al., "Localization of a Negative Thyroid Hormone-Response Region in Hepatic Stearoyl-CoA Desaturase Gene 1", Biochem. Biophys. Res. Comm., vol. 233, pp. 838-843, (1997).

Zhang et al., "Human Stearoyl-CoA Desaturase: Alternative Transcripts enerated from a Single Gene by Usage of Tandem Polyadenylation Sites", Biochem. J., vol. 340, pp. 255-264 (1999).

Database Biosis Online. Waters & Ntambi: "Polyunsaturated Fatty Acids Inhibit Hepatic Stearoyl-CoA Desaturase-1 Gene in Diabetic Mice", vol. 31, No. Suppl., pp. S33-S36 (1996), Accession No. PREV199698795704.

Kurebayashi S. et al., "Thiazolidinediones Downregulate Stearoyl-CoA Desaturase 1 Gene Expression in 3T3-L1 Adipocytes", Diabetes, vol. 46, pp. 2115-2118, Dec. 1997.

Singh & Ntambi, "Nuclear Factor 1 is Essential Fir the Expression of Stearoyl-CoA Desaturase 1 Gene During Preadipocyte Differentiation", Biochim. Biophys. Acta., vol. 1398, 1998, pp. 148-156.

Sessler et al., "Regulation of Stearoyl-CoA Desaturase 1 mRNA Stability by Polyunsaturated Fatty Acids in 3T3-L1 Adipocytes", J. Biol. Chem., vol. 271, No. 47, pp. 29854-29858 (Nov. 22, 1996).

Ntambi, J.M., "Regulation of Stearoyl-CoA Desaturase by Polyunsaturated Fatty Acids and Cholesterol", J. Lipid Res. vol. 40, pp. 1549-1558 (1999).

Park et al., "Lipid Level and Type Alter Stearoyl CoA Desaturase mRNA Abundance Differently in Mice with Distinct Susceptibilities to Diet-Influenced Diseases", J. Nutrition, vol. 127, pp. 566-573 (1997).

Agrawal et al., Molecular Med. Today, vol. 6, pp. 72-81 (2000).

Branch, A., Trends in Biochem. Sci. (TIBS), vol. 23, pp. 45-50 (1998).

Cook, S.T., Antisense Res. And Applica., Chapter 2, pp. 51-101, S. Crooke, S. Ed. (Springer-Verlag 1998).

Crooke, S.T., Antisense Res. and Applica., Chapter 1, pp. 1-50, S. Crooke, S. Ed. (Springer-Verlag 1998).

Derossi et al., J. Biol. Chem., vol. 269, pp. 10,444-10,450 (1994).

Elliott et al., Cell, vol. 88, pp. 223-233 (1997).

Hamilton, J., J. Lipid Res., vol. 39, pp. 467-481 (1998).

Kinsella et al., Am. J. Clin. Nutr., vol. 52, pp. 1-28 (1990).

Lee et al., Atherosclerosis, vol. 108, pp. 19-25 (1994).

Martin et al., J. Nutrition, vol. 130, pp. 1524-1530 (2000).

Moreton et al., Applied Microbiol. Biotech., vol. 22, pp. 42-45 (1984).

Pan et al., J. Nutrition, vol. 124 (No. 9), pp. 1555-1565 (1994).

Pooga, M., FASEB J., vol. 12, pp. 67-77 (1998).

Bjorntorp, Clin. Endocrinology and Medicine, vol. 13, pp. 47-69 (1999).

Joshi et al., J. Lipid Res., vol. 18, pp. 32-36 (1977).

Landschulz et al., Biochem. Biophys. Res. Comm., vol. 200, pp. 763-768 (1994).

Madsen et al., J. Lipid Res., vol. 38, pp. 554-563 (1997).

Miller and Ntambi, PNAS, vol. 93, pp. 9443-9448 (1996).

Miller et al., Biochem. Biophys. Res. Comm., vol, 231, 206-210 (1997).

Sessler et al., J. Nutrition., vol. 128, pp. 923-926 (1998).

Tabor et al., J. Biol. Chem., vol. 274, pp. 274, pp. 20603-20610 (1999).

* cited by examiner

Figure 1
A
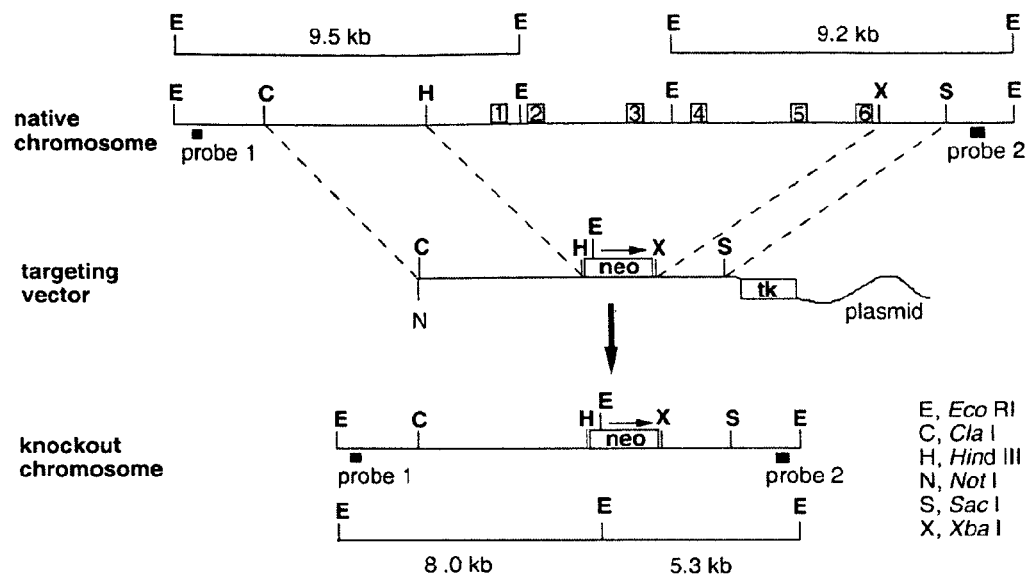
B
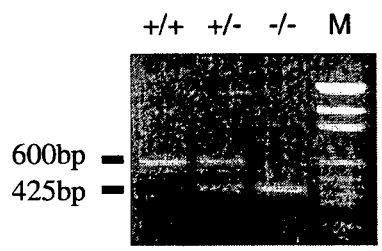
C
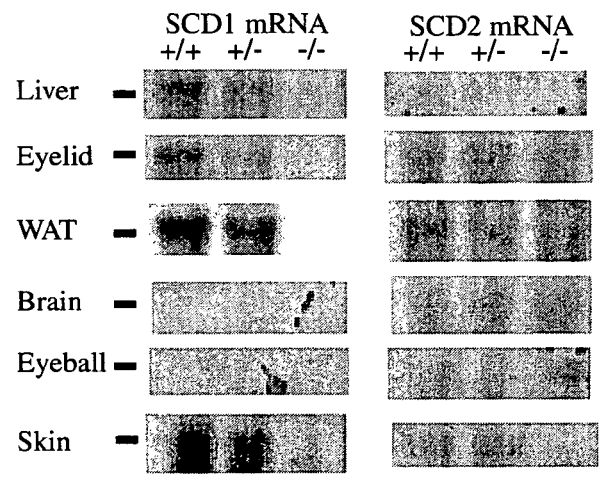
D
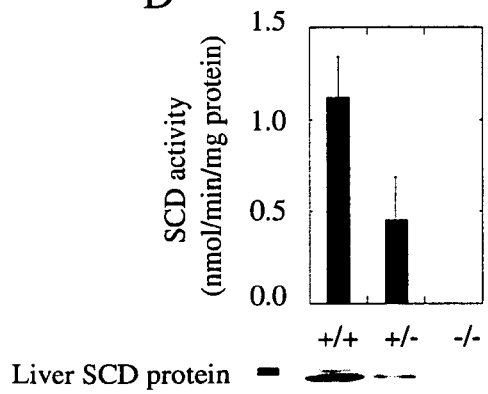

Figure 2
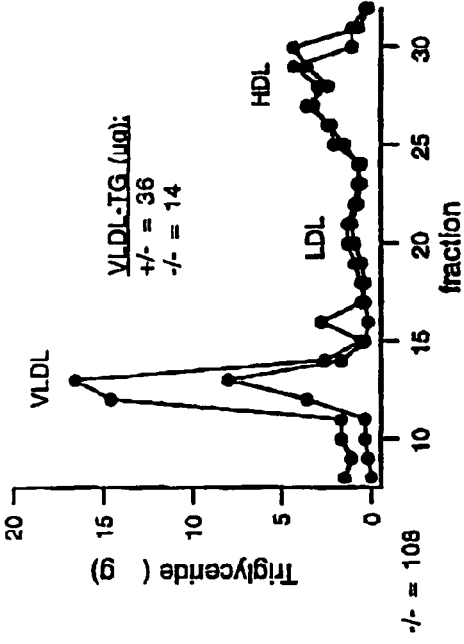
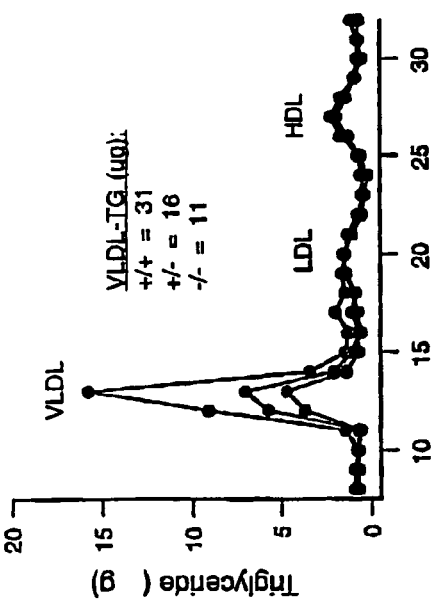
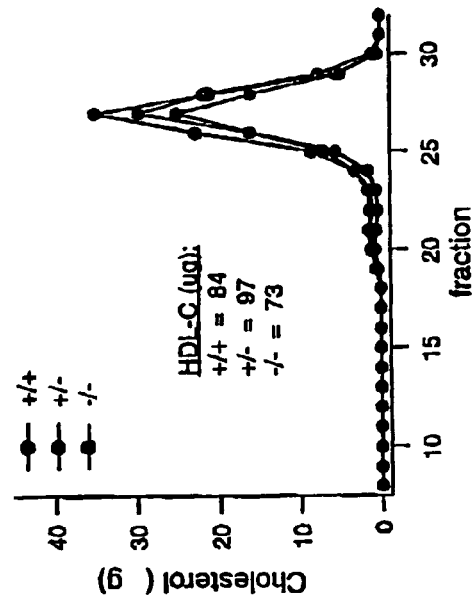

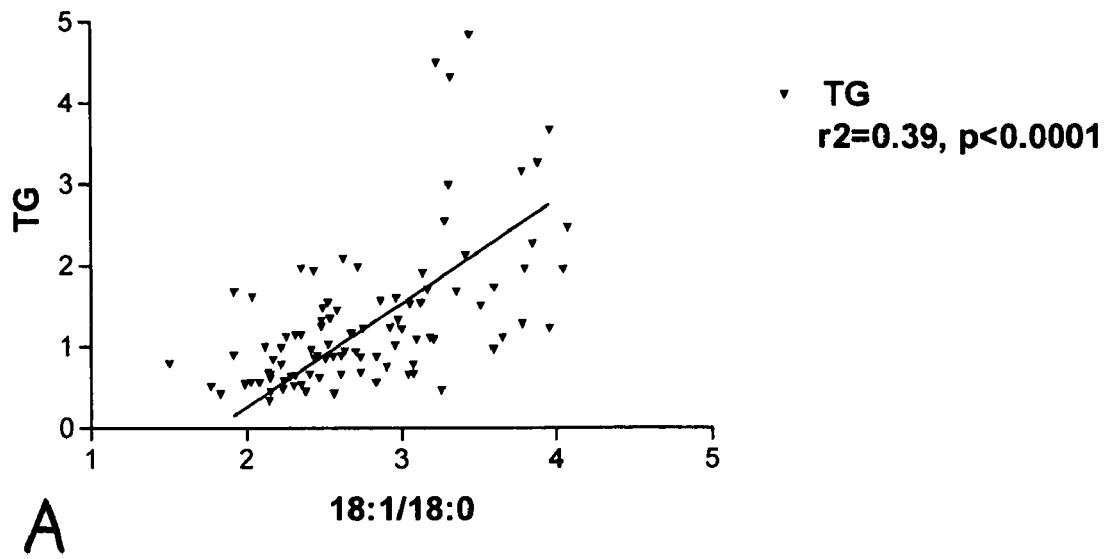
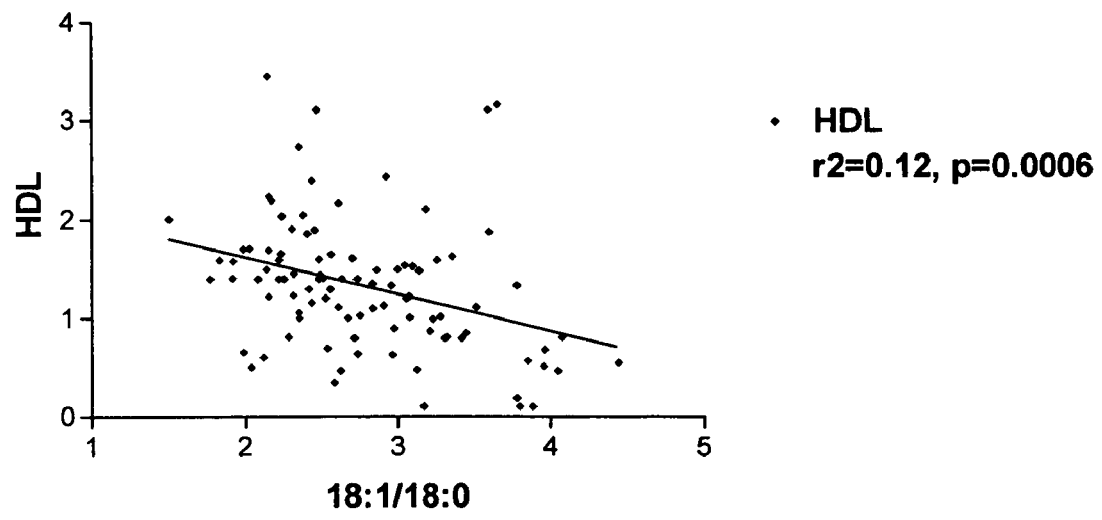
Figure 5

Figure 8
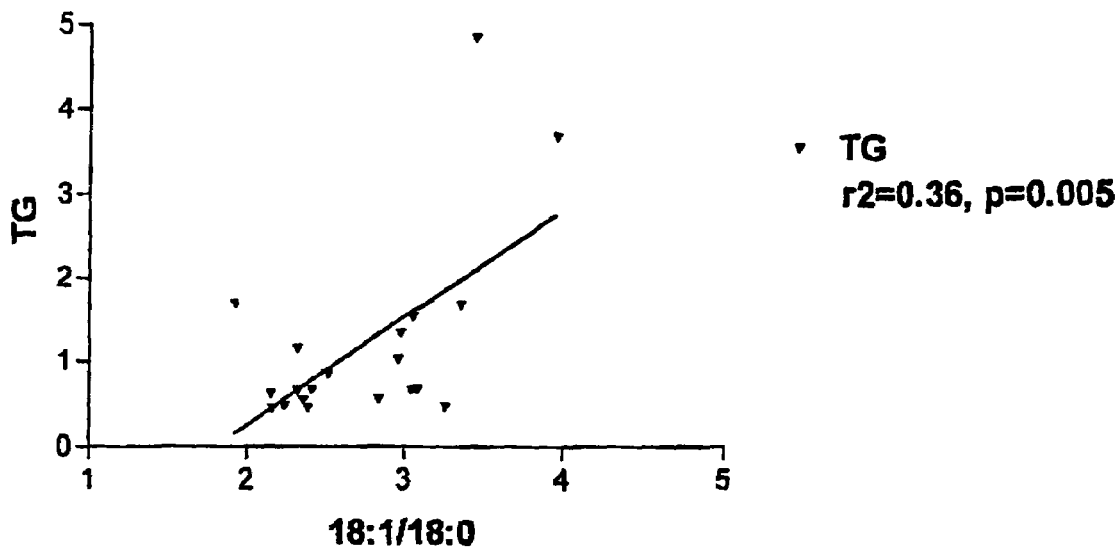
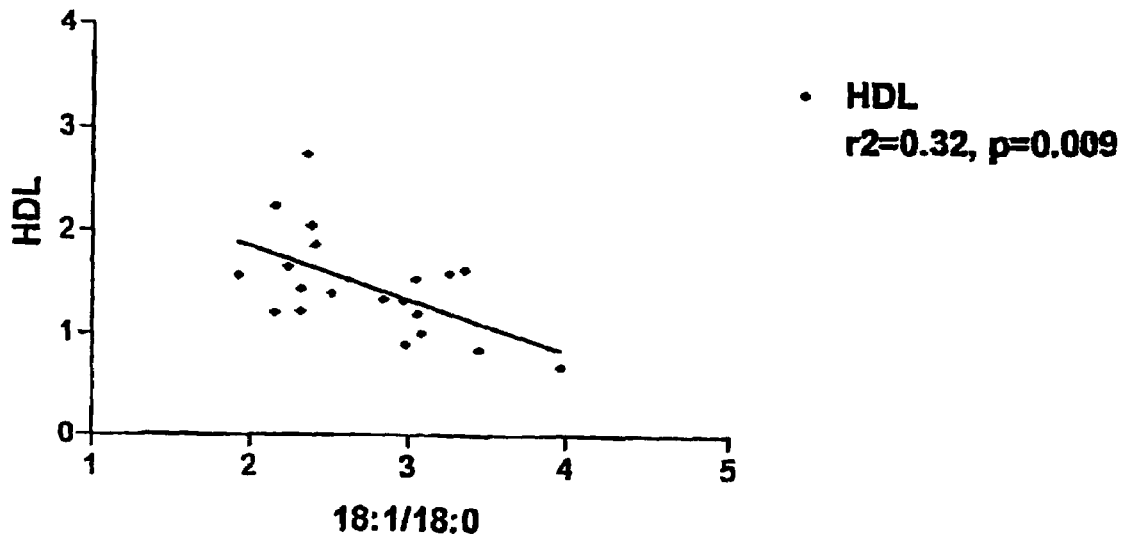

Figure 10
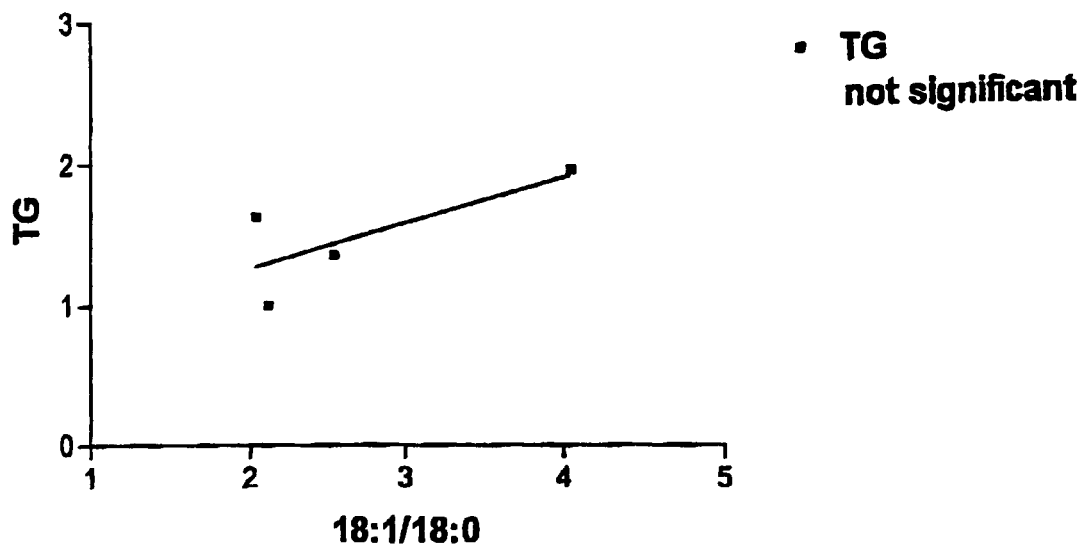
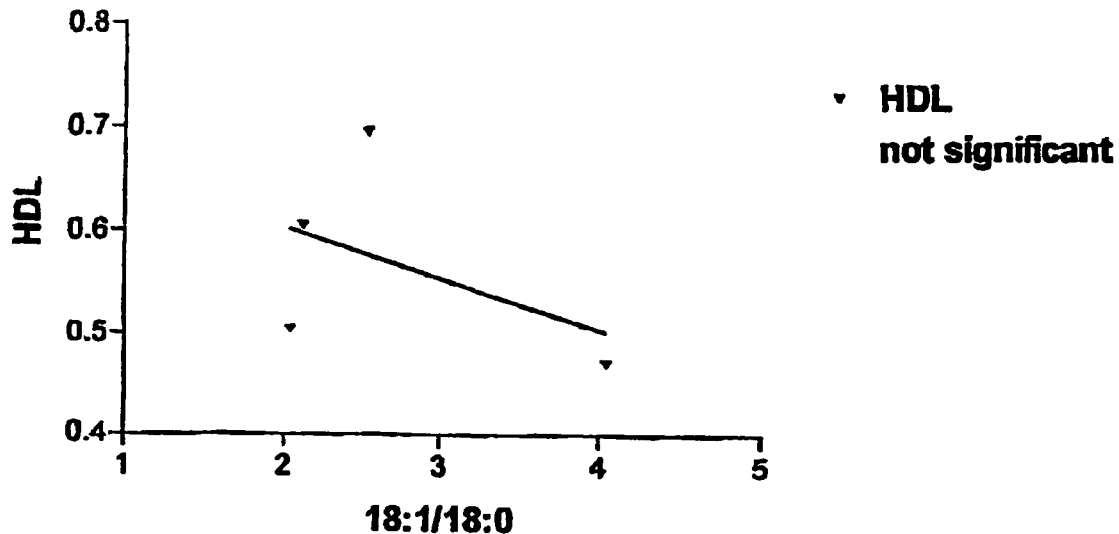

Figure 11
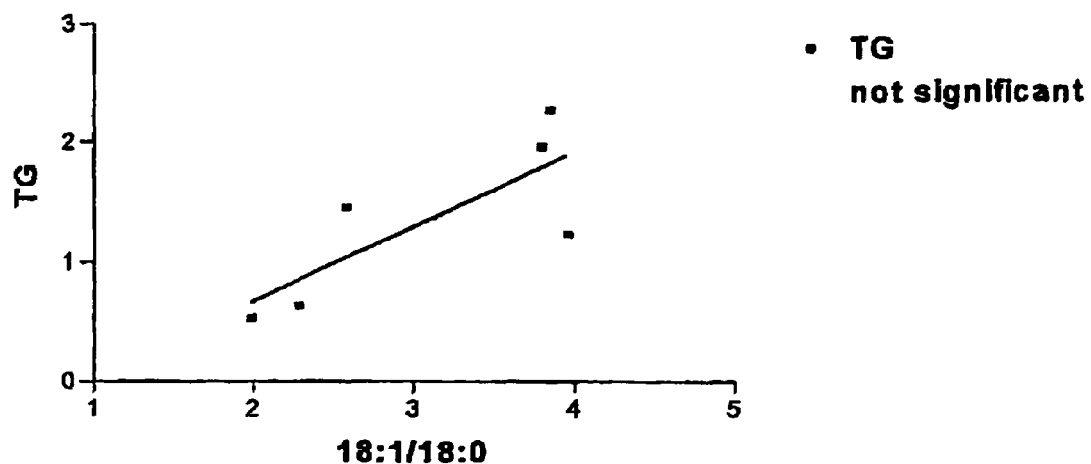
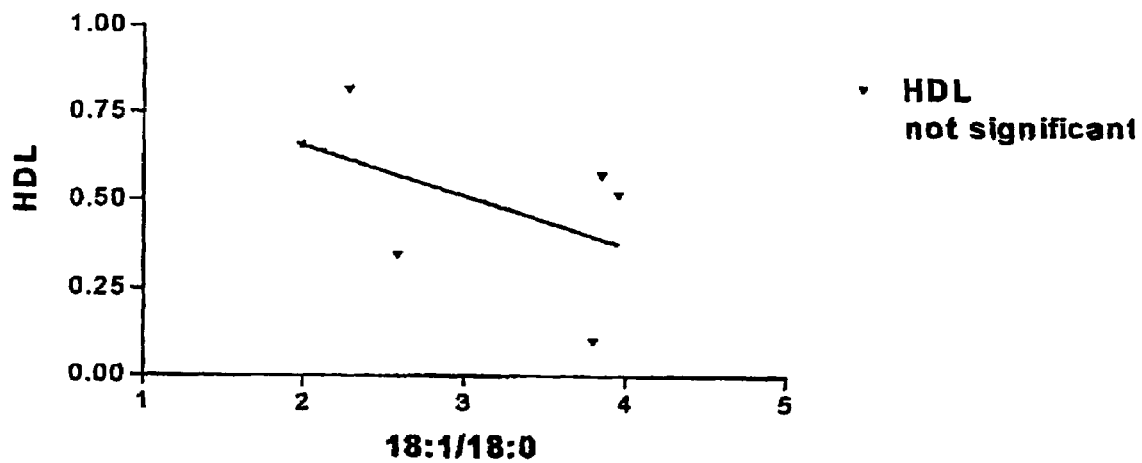

C

Homology between Mouse and Human Stearoyl-CoA Desaturase Promoters

Figure 19
Inhibition of Stearoyl-CoA Desaturase with 3 Fatty Acids
12/19,20/00 Inhibitor screen
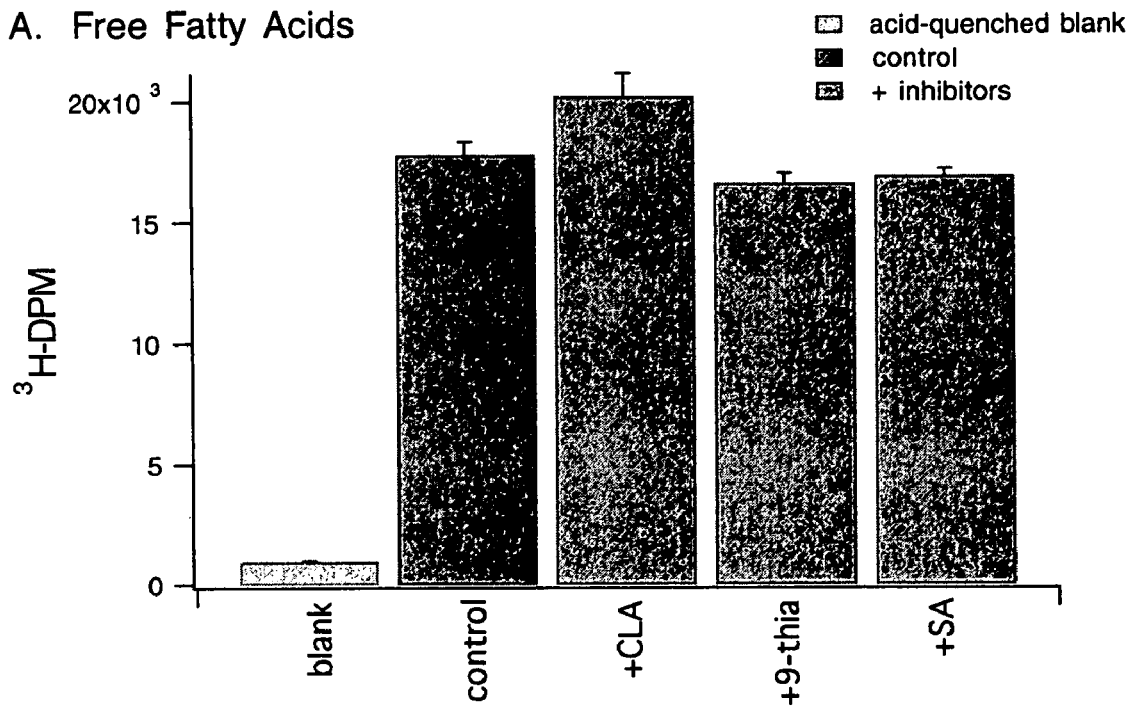
A. Free Fatty Acids
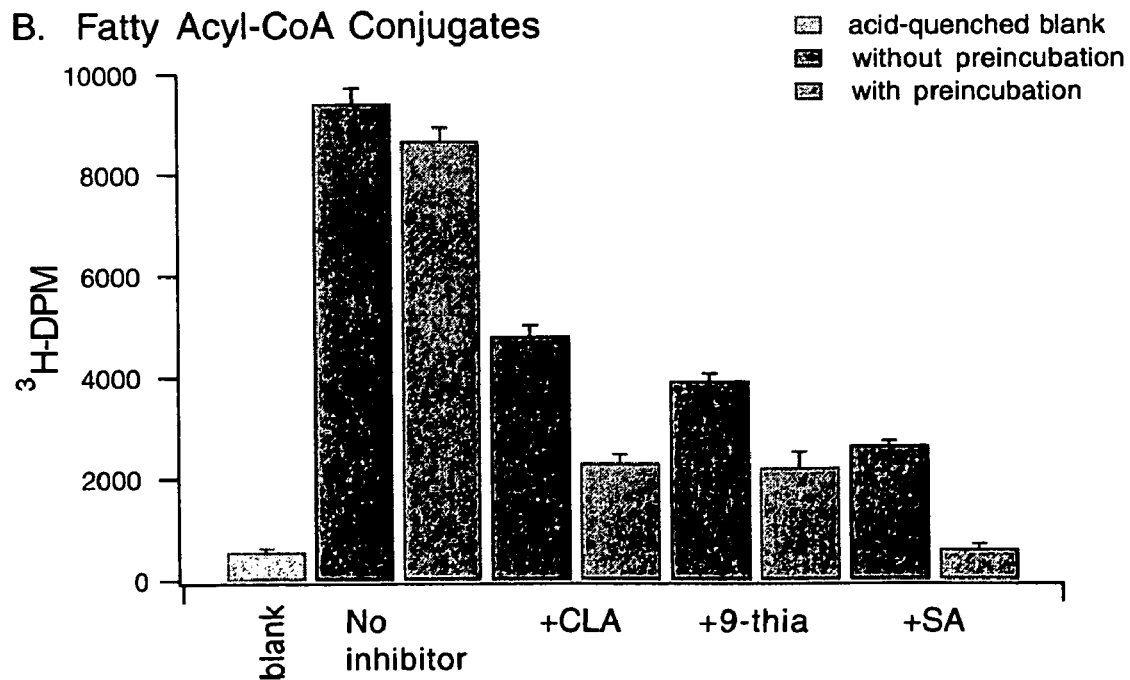
B. Fatty Acyl-CoA Conjugates Stearoyl-CoA desaturation in +/+ SCD1 liver microsomes
1/10/01 second addition of stearoyl-CoA (A), 0.3ml volume (B)

SEQUENCE LISTING

<160> NUMBER OF SEQ ID NOS: 6

<210> SEQ ID NO 1
<211> LENGTH: 617
<212> TYPE: DNA
<213> ORGANISM: Homo sapiens

<400> SEQUENCE: 1

```
ggtccccgcc ccttccagag agaaagctcc cgacgcggga tgccgggcag aggcccagcg      60
gcgggtggaa gagaagctga gaaggagaaa cagaggggag ggggagcgag gagctggcgg     120
cagagggaac agcagattgc gccgagccaa tggcaacggc aggacgaggt ggcaccaaat     180
tcccttcggc caatgacgag ccggagttta cagaagcctc attagcattt ccccagaggc     240
aggggcaggg gcagaggccg ggtggtgtgg tgtcggtgtc ggcagcatcc ccggcgccct     300
gctgcggtcg ccgcgagcct cggcctctgt ctcctccccc tcccgccctt acctccacgc     360
gggaccgccc gcgccagtca actcctcgca ctttgcccct gcttggcagc ggataaaagg     420
gggctgagga aataccggac acggtcaccc gttgccagct ctagccttta aattcccggc     480
tcggggacct ccacgcaccg cggctagcgc cgacaaccag ctagcgtgca aggcgccgcg     540
gctcagcgcg taccggcggg cttcgaaacc gcagtcctcc ggcgaccccg aactccgctc     600
cggagcctca gccccct                                                    617
```

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: PCR Primer for Exon 6.

<400> SEQUENCE: 2

```
gggtgagcat ggtgctcagt ccct                                             24
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: PCR Primer for the neo gene.

<400> SEQUENCE: 3

```
atagcaggca tgctggggat                                                  20
```

```
<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: PCR
      amplification primer.

<400> SEQUENCE: 4
cacaccatat ctgtccccga caaatgtc                                         28

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Upstream
      PCR amplification primer.
<220> FEATURE:
<221> NAME/KEY: misc_feature
<222> LOCATION: (1)...(14)
<223> OTHER INFORMATION: n=a,t,g or c

<400> SEQUENCE: 5
nnnnggtacc ttnngaaaag aacagcgccc                                       30

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Downstream
      PCR amplification primer.
<220> FEATURE:
<221> NAME/KEY: misc_feature
<222> LOCATION: (1)...(4)
<223> OTHER INFORMATION: n=a,t,g or c

<400> SEQUENCE: 6
nnnnagatct gtgcgtggag gtccccg                                          27
```

METHODS AND COMPOSITIONS USING STEAROYL-COA DESATURASE TO IDENTIFY TRIGLYCERIDE REDUCING THERAPEUTIC AGENTS

This application is a divisional of U.S. application Ser. No. 09/792,468, filed 23 Feb. 2001, now U.S. Pat. No. 6,987,001, which claims priority of U.S. Provisional Application 60/184,526, filed 24 Feb. 2000, U.S. Provisional Application 60/221,697, filed 31 Jul. 2000, and U.S. Provisional Application 60/255,771, filed 15 Dec. 2000, the disclosures of all of which are hereby incorporated by reference in their entirety.

FIELD OF THE INVENTION

The present invention relates generally to the field of stearoyl-CoA desaturase and its involvement in various human diseases. Stearoyl-CoA desaturase, and the gene encoding it, are useful for identification and development of therapeutic agents for the treatment of such diseases.

BACKGROUND OF THE INVENTION

Acyl desaturase enzymes catalyze the formation of double bonds in fatty acids derived from either dietary sources or de novo synthesis in the liver. Mammals synthesize four desaturases of differing chain length specificity that catalyze the addition of double bonds at the $\Delta 9$, $\Delta 6$, $\Delta 5$ and $\Delta 4$ positions. Stearoyl-CoA desaturases (SCDs) introduce a double bond in the $\Delta 9$-position of saturated fatty acids. The preferred substrates are palmitoyl-CoA (16:0) and stearoyl-CoA (18:0), which are converted to palmitoleoyl-CoA (16:1) and oleoyl-CoA (18:1), respectively. The resulting mono-unsaturated fatty acids are substrates for incorporation into phospholipids, triglycerides, and cholesterol esters.

A number of mammalian SCD genes have been cloned. For example, two genes have been cloned from rat (SCD1, SCD2) and four SCD genes have been isolated from mouse (SCD1, 2, 3, and 4). A single SCD gene, SCD1, has been characterized in humans.

While the basic biochemical role of SCD has been known in rats and mice since the 1970's (Jeffcoat R. and James, A T. 1984. Elsevier Science, 4: 85-112; de Antueno, R J. 1993. Lipids 28(4)285-290), it has not, prior to this invention, been directly implicated in human disease processes. Studies in non-human animals have obscured our understanding of the role of SCD in humans due to the well documented differences in the biochemical processes in different species. In rodents, for example, lipid and cholesterol metabolism is particularly obscured by the absence of Cholesterol Ester Transport Protein (CETP) (see Foger, B. et al. 1999. J. Biol. Chem. 274(52) 36912).

Further, the existence of multiple SCD genes in mice and rats adds additional complexity to determining the specific role of each of these genes in disease processes. Differences in tissue expression profiles, substrate specificity, gene regulation and enzyme stability may be important in elucidating which SCD gene plays the dominant role in each disorder. Most previous SCD studies assess SCD gene function by measuring mRNA levels or by measuring levels of monounsaturated fatty acids as an indirect measure of SCD enzyme activity. In both these cases this analysis may be misleading. In the latter method it has been particularly misleading and difficult to discern the relative contribution of SCD1 to the plasma desaturation index (the ratio of monounsaturated fatty acids to saturated fatty acids of a specific chain length) due to the fact that multiple SCD enzymes may contribute to the production of monounsaturated fatty acids. Prior to this invention, the relative contributions of the multiple SCD isoforms to the desaturation index was unknown. In summary, previous studies have not differentiated which SCD isoforms play a major role in the total desaturase activity as measured by the desaturation index.

Recent work in in vitro chicken hepatocyte cell culture relates delta-9 desaturase activity to impaired triacylglycerol secretion (Legrand, P. and Hermier, D. (1992) *Int. J. Obesity* 16, 289-294; Legrand, P., Mallard, J., Bernard-Griffiths, M. A., Douaire, M., and Lemarchal, P. *Comp. Biochem. Physiol.* 87B, 789-792; Legrand, P., Catheline, D., Fichot, M.-C., Lemarchal, P. (1997) *J. Nutr.* 127, 249-256). This work did not distinguish between isoforms of delta-9 desaturase that may exist in the chicken, once again failing to directly implicate a specific SCD enzyme to account for a particular biological effect, in this case, impaired triglyceride secretion.

Nor does this in vitro work correlate well to humans because substantial differences exist between chicken and human lipoprotein metabolism in vivo. Such differences include the presence, in chicken, of entirely different lipoproteins, such as vitellogenin, and distinct processes such as the massive induction of hepatic triglyceride synthesis during ovulation. Other differences such as the type of lipoproteins used for cholesterol transport and the process of secretion of dietary triglyceride in chylomicrons are well documented. These major differences between avians and mammals mean that extrapolation from the avians to mammals in the area of triglyceride metabolism must be considered provisional pending confirmation in humans.

Two other areas of background art form an important basis to the instant invention. Firstly, this invention relates to cholesterol and lipid metabolism, which in humans has been intensely studied. Since cholesterol is highly apolar, it is transported through the bloodstream in the form of lipoproteins consisting essentially of a core of apolar molecules such as cholesterol ester and triglyceride surrounded by an envelope of amphipathic lipids, primarily phospholipids. In humans, approximately 66% of cholesterol is transported on low density lipoprotein (LDL) particles, about 20% on high density lipoprotein (HDL) particles, and the remainder on very low density lipoprotein (VLDL) particles. An excellent reference to the basic biochemistry of cholesterol metabolism in humans and other organisms is found at Biology of Cholesterol. Ed. Yeagle, P. CRC Press, Boca Raton, Fla., 1988.

Secondly, this invention takes advantage of new findings from the Asebia mouse (Gates, et al. (1965) Science. 148: 1471-3). This mouse is a naturally occurring genetic variant mouse that has a well known defect in sebaceous glands, resulting in hair loss and scaly skin. The Asebia mouse has recently been reported to have a deletion in SCD1 resulting in the formation of an early termination site in exon 3 of the SCD1 gene. Animals homozygous for this mutation, or a distinct deletion allele which encompasses exons 1-4, do not express detectable amounts of the wild-type SCD1 mRNA transcript (November 1999. *Nature Genetics*. 23:268 et seq.; and PCT patent publication WO 00/09754)]. Since the full extent of this naturally occurring deletion is unknown, it is also unknown if other genes neighboring SCD1, or elsewhere in the genome, could also be involved in the Asebia phenotype. In order to specifically study the activity of SCD1 in these disease processes, a specific SCD1 knockout mouse is required. The prior work on this variant has focused on the role of this mutation in skin disorders and not on triglyceride or VLDL metabolism.

It is an object of the instant invention to identify diseases and disorders that are linked specifically to SCD1 biological activity in humans, and in a preferred embodiment, diseases and disorders of triglyceride metabolism. It is a further object to develop screening assays to identify and develop drugs to treat those diseases, disorders and related conditions. Further, it is an object of this invention to provide compositions for use in treating these disease, disorders and related conditions.

BRIEF SUMMARY OF THE INVENTION

This invention discloses, for the first time, the role of human stearoyl-CoA desaturase-1 ("hSCD1") in a wide range of human diseases and disorders. In particular, SCD1 biological activity in humans is directly related to serum levels of triglycerides and VLDL. In addition, SCD1 biological activity also affects serum levels of HDL, LDL, and/or total cholesterol, reverse cholesterol transport, and the production of secretions from mucous membranes, monounsaturated fatty acids, wax esters, and/or the like.

It is an object of the present invention to provide a process or screening assay for identifying, from a library of test compounds, a therapeutic agent which modulates the biological activity of said human stearoyl-CoA desaturase (hSCD1) and is useful in treating a human disorder or condition relating to serum levels of triglyceride or VLDL. Preferably, the screening assay identifies inhibitors of hSCD1 which lower serum triglyceride levels and provide an important cardioprotective benefit for humans.

It is also an object of the present invention to provide a process or screening assay for identifying, from a library of test compounds, a therapeutic agent which modulates the biological activity of said human stearoyl-CoA desaturase (hSCD1) and is useful in treating a human disorder or condition relating to serum levels of HDL, LDL, and/or total cholesterol, reverse cholesterol transport or the production of secretions from mucous membranes, monounsaturated fatty acids, wax esters, and/or the like In one aspect, the present invention relates to vectors comprising human stearoyl-CoA desaturase (hSCD1) genes and promoter sequences and to recombinant eukaryotic cells, and cell lines, preferably mammalian cells, and most preferably human cells, and cell lines, transfected so as to comprise such vectors and/or said polynucleotides and wherein said cells express hSCD1. Disclosed herein is the full length promoter sequence for hSCD1, SEQ ID. No. 1.

It is also an object of the present invention to provide agents capable of modulating the activity and/or expression of human stearoyl-CoA desaturase 1 (hSCD1) as disclosed herein, especially where said modulating ability was first determined using an assay comprising hSCD1 biological activity or a gene encoding hSCD1. Pharmaceutical compositions comprising such agents are specifically contemplated.

It is a still further object of the present invention to provide agents wherein said agent is useful in treating, preventing and/or diagnosing a disease or condition relating to hSCD1 biological activity.

It is a yet further object of the present invention to provide a process for preventing or treating a disease or condition in a patient afflicted therewith comprising administering to said patient a therapeutically or prophylactically effective amount of a composition as disclosed herein.

In a pharmacogenomic application of this invention, an assay is provided for identifying cSNPs (coding region single nucleotide polymorphisms) in hSCD1 of an individual which are associated with human disease processes or response to medication.

In other aspects, the present invention also provides a process for diagnosing a disease or condition in a patient, commonly a human being, suspected of being afflicted therewith, or at risk of becoming afflicted therewith, comprising obtaining a tissue sample from said patient and determining the level of activity of hSCD1 in the cells of said tissue sample and comparing said activity to that of an equal amount of the corresponding tissue from a patient not suspected of being afflicted with, or at risk of becoming afflicted with, said disease or condition.

In other aspects, the present invention also provides a process for diagnosing a disease or condition in a patient, commonly a human being, suspected of being afflicted therewith, or at risk of becoming afflicted therewith, comprising obtaining a tissue sample from said patient and identifying mutations in the hSCD1 gene in the cells of said tissue sample and comparing said gene to that of a corresponding tissue from a patient not suspected of being afflicted with, or at risk of becoming afflicted with, said disease or condition.

BRIEF DESCRIPTION OF THE DRAWINGS

FIG. 5 shows a linear regression analysis using a human data set. The ratio of 18:1/18:0 showed a significant relationship to TG levels ($r_2$=0.39, p<0.0001) (Panel A), as well as a significant correlations to HDL levels ($r^2$=0.12, p=0.0006) (Panel B). The experimental details are further described in Example 2.

FIG. 8 shows an observed relationship between 18:1/18:0 and TG levels was observed in a family (HA-1) that segregates a high HDL phenotype. Using linear regression analysis, a significant relationship between 18:1/18:0 and TG was observed ($r^2=0.36$, $p=0.005$ (Panel A)). Panel B shows a significant relationship between 18:1/18:0 ratio and HDL levels in this family ($r^2=0.32$, $p=0.009$).

FIG. 10 shows an analysis of a family (NL-001), which segregated a low HDL phenotype of unknown genetic etiology and tended towards the relationships observed in FIGS. 5-9.

FIG. 11 shows an analysis of family NL-0020 which segregated an ABCA1 mutation and tended towards the relationships noted in FIGS. 5-9.

FIG. 19 shows inhibition of SCD1 with 3 known fatty acid inhibitors. Microsomes from wild type mice were used to test the effectiveness of three known inhibitors of SCD1: conjugated linoleic acid (CLA), 9-thia stearic acid (9-thia) and sterculic acid (SA). Panel A shows that when added as the free fatty acid none were effective to suppress SCD1activity. However, panel B shows that if pre-conjugated to CoA (done by incubating the microsomes with CoA and ATP prior to the addition of $^3$H-stearoyl CoA) the three inhibitors show graded inhibition of SCD1 with sterculic acid suppressing nearly 100% of the activity for the preincubation condition. This experiment establishes that SCD1 activity can be inhibited with known inhibitors but they appear to require conjugation with CoA. An important use of this screening assay is to find small molecules that are potent inhibitors of SCD1 biological activity without conjugation to CoA.

DEFINITIONS

Figure 3:
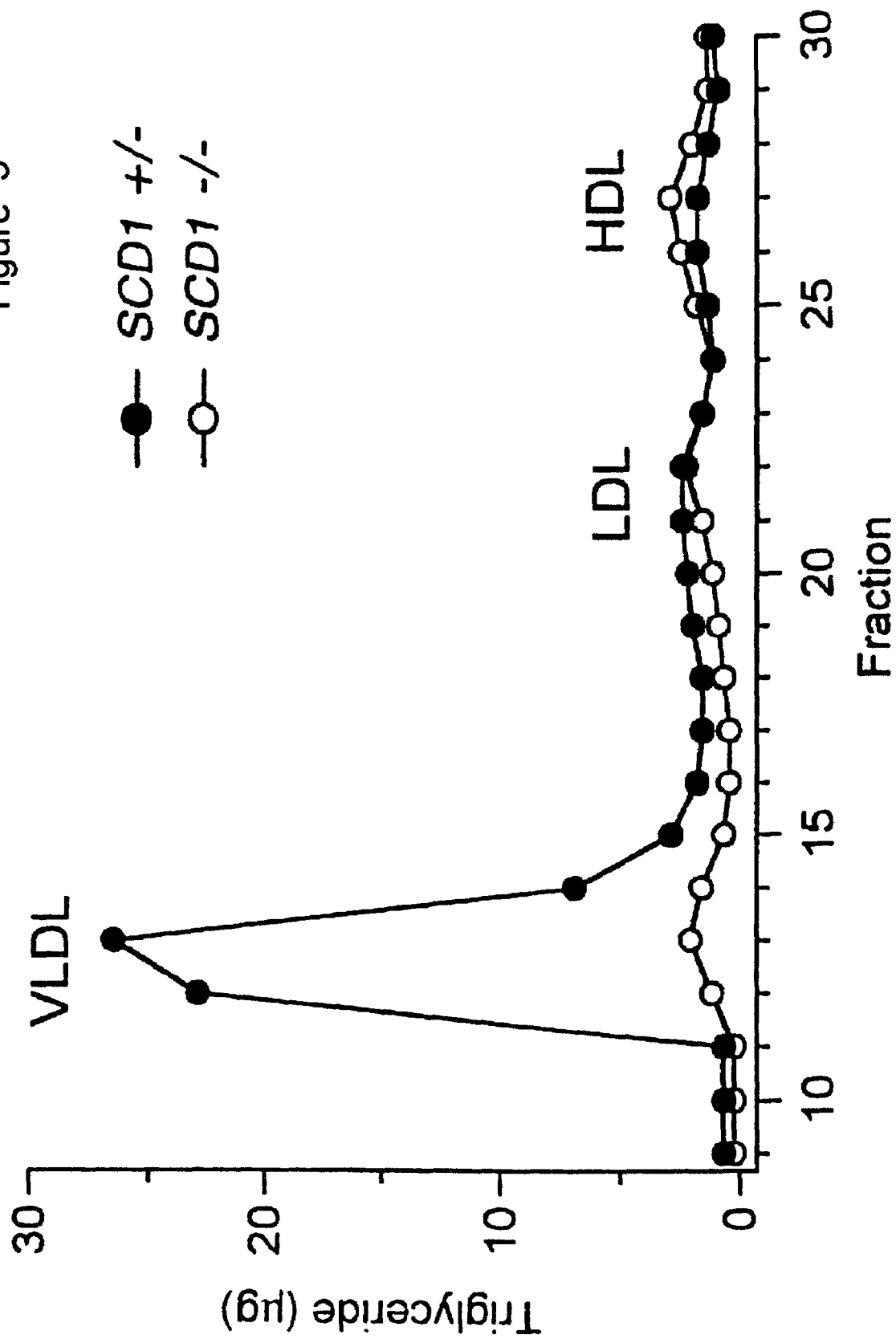
FIG. 3. VLDL-triglyceride levels in Asebia (SCD1–/–) and SCD1+/– mice. Plasma lipoproteins were separated by fast performance liquid chromatography and the distribution of triglycerides among lipoproteins in the various density fractions of the mice (n=3) were measured. SCD–/– (open circles), SCD1+/– (filled circles). The lipoprotein peaks for VLDL, LDL and HDL are indicated.

"Isolated" in the context of the present invention with respect to polypeptides or polynucleotides means that the material is removed from its original environment (e.g., the natural environment if it is naturally occurring). For example, a naturally-occurring polynucleotide or polypeptide present in a living organism is not isolated, but the same polynucleotide or polypeptide, separated from some or all of the co-existing materials in the natural system, is isolated. Such polynucleotides could be part of a vector and/or such polynucleotides or polypeptides could be part of a composition, and still be isolated in that such vector or composition is not part of its natural environment. The polypeptides and polynucleotides of the present invention are preferably provided in an isolated form, and preferably are purified to homogeneity.

The nucleic acids and polypeptide expression products disclosed according to the present invention, as well as expression vectors containing such nucleic acids and/or such polypeptides, may be in "enriched form." As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, claimed polypeptide which has a purity of preferably 0.001%, or at least 0.01% or 0.1%; and even desirably 1% by weight or greater is expressly contemplated.

The term "coding region" refers to that portion of a gene which either naturally or normally codes for the expression product of that gene in its natural genomic environment, i.e., the region coding in vivo for the native expression product of the gene. The coding region can be from a normal, mutated or altered gene, or can even be from a DNA sequence, or gene, wholly synthesized in the laboratory using methods well known to those of skill in the art of DNA synthesis.

In accordance with the present invention, the term "nucleotide sequence" refers to a heteropolymer of deoxyribonucleotides (for DNA) or ribonucleotides (for RNA). Generally, DNA segments encoding the proteins provided by this invention are assembled from cDNA fragments and short oligonucleotide linkers, or from a series of oligonucleotides, to provide a synthetic gene which is capable of being expressed in a recombinant transcriptional unit comprising regulatory elements derived from a microbial or viral operon.

The term "expression product" means that polypeptide or protein that is the natural translation product of the gene and any nucleic acid sequence coding equivalents resulting from genetic code degeneracy and thus coding for the same amino acid(s).

The term "fragment," when referring to a coding sequence, means a portion of DNA comprising less than the complete coding region whose expression product retains essentially the same biological function or activity as the expression product of the complete coding region.

The term "primer" means a short nucleic acid sequence that is paired with one strand of DNA and provides a free 3'OH end at which a DNA polymerase starts synthesis of a deoxyribonucleotide chain.

The term "promoter" means a region of DNA involved in binding of RNA polymerase to initiate transcription, and includes all nucleotides upstream (5') of the transcription start site.

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence.

The present invention further relates to a polypeptide which has the deduced amino acid sequence, as well as fragments, analogs and derivatives of such polypeptide.

The terms "fragment," "derivative" and "analog" when referring to the polypeptide, means a polypeptide which retains essentially the same biological function or activity as such polypeptide. Thus, an analog includes a proprotein which can be activated by cleavage of the proprotein portion to produce an active mature polypeptide. Such fragments, derivatives and analogs must have sufficient similarity to the SCD1 polypeptide so that activity of the native polypeptide is retained.

The polypeptide of the present invention may be a recombinant polypeptide, a natural polypeptide or a synthetic polypeptide, and is preferably a recombinant polypeptide.

The fragment, derivative or analog of the SCD1 polypeptide may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

As known in the art "similarity" between two polypeptides is determined by comparing the amino acid sequence and its conserved amino acid substitutes of one polypeptide to the sequence of a second polypeptide.

In accordance with the foregoing, the present invention also relates to an isolated stearoyl-CoA desaturase encoded by the isolated polynucleotide of the invention.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, such terms refer to the products produced by treatment of said polynucleotides with any of the common endonucleases.

DETAILED SUMMARY OF THE INVENTION

The present invention relates to the activity of human stearoyl-CoA desaturase-1 in human disease processes. In accordance therewith, compounds that specifically modulate human stearoyl-CoA desaturase-1 activity or expression level are useful in the treatment of a human disorder or condition relating to serum levels of triglyceride or VLDL, and provide an important cardioprotective benefit when administered to humans. Compounds that modulate hSCD1 activity or expression are also useful for modulating serum levels of HDL, LDL, and/or total cholesterol, and/or reverse cholesterol transport. Finally, compounds that modulate hSCD1 activity or expression are also useful for modulating the production of secretions from mucous membranes, monounsaturated fatty acids, wax esters, and the like.

The SCD1 Gene and Protein

Human Stearoyl-CoA Desaturase-1 (also called SCD1, hSCD and hSCD1) has been identified with the full cDNA sequence first released to GenBank as GenBank Accession Y13647 (also NM005063) dated Jun. 6, 1997. Further descriptions of SCD1, including partial promoter sequences can be found on GenBank under the following accession numbers: gb|AF097514.1|AF097514; dbj|AB032261.1|AB032261; gb|AF116616.1|AF116616; ref|XM_005719.1|; gb|AF113690.1 |AF113690; and gb|S70284.1|S70284

In one aspect the present invention relates to uses of an isolated polynucleotide comprising a non-genomic polynucleotide having at least 90% identity, preferably 95% identity, most preferably at least a 98% identity to the sequence of human stearoyl-CoA reductase-1, especially where said sequences are the same and including any of the complements of any of the foregoing.

Figure 14:
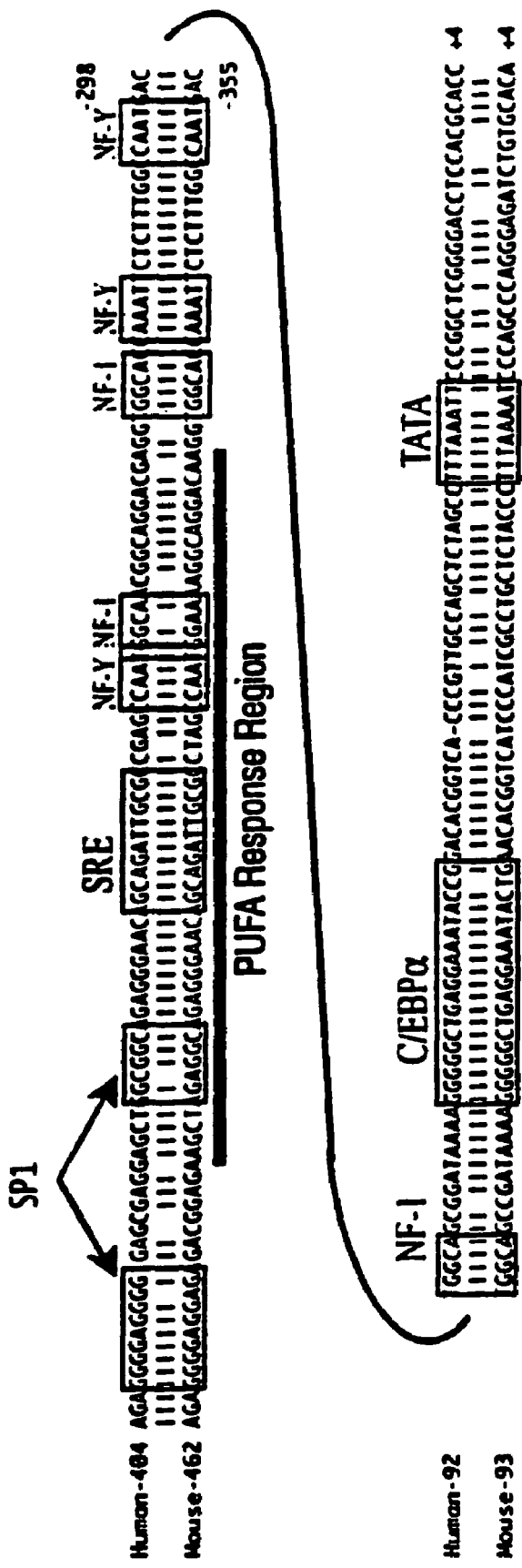
FIG. 14. Location of regulatory sequences and binding sites in homologous region of the mouse SCD1 and human SCD1 promoter and 5'-flanking regions. The top scale denotes the position relative to the transcriptional start site. Important promoter sequence elements are indicated.

The full promoter sequence of hSCD1 is SEQ ID. No. 1 and FIG. 14 illustrates the functional elements conserved between the mouse and human SCD1 promoter regions.

In one aspect the present invention relates to uses of an isolated polypeptide having at least 90% identity, preferably 95% identity, most preferably at least a 98% identity to human stearoyl-CoA reductase-1, especially where said sequences are the same. The polypeptide sequence has been previously disclosed and can be found at the following SwissProtein database accession series: ACCESSION No. O00767; PID g3023241; VERSION O00767 GI:3023241; DBSOURCE: swissprot: locus ACOD_HUMAN, accession O00767. Alternatively, the polypeptide sequence can be determined from the cDNA sequence references provided above.

SCD1 in Human Disease Processes

As disclosed herein, a number of human diseases and disorders are the result of aberrant SCD1 biological activity and may be ameliorated by modulation of SCD1 biological activity using therapeutic agents.

The most significant teaching of the present disclosure relates to the role of SCD1 in modulating serum triglyceride and VLDL levels in humans. Two major findings are established herein. Firstly, Example 1 below shows that the lipoprotein profiles of SCD1 knock-out mice demonstrate a 65% reduction in serum triglyceride and VLDL levels. These correspond with the lipoprotein profiles of Asebia mice which are also included herein. The lipoprotein profiles of both the Asebia and the SCD1 knock-out mouse were not previously known but due to the targeted and specific nature of the engineered mutation, the correlation of SCD1 activity and serum triglyceride levels can be drawn with certainty. While other SCD isoforms may play a role in triglyceride levels, this data indicates that SCD1, specifically, plays the major role in this process.

There are significant differences in lipoprotein metabolism between mouse and humans, and while the foregoing data are convincing in the mouse for a major and specific role for SCD1 in modulation of trigylceride levels, this still needed confirmatory experiments in humans. The second major finding, therefore, presented in Example 2, below, demonstrates a significant correlation between SCD activity in humans and levels of serum triglycerides. It has thus been discovered that SCD1 biological activity in humans is directly related to levels of serum triglycerides.

In accordance with the present invention, the Asebia mouse phenotype (first described by Gates, et al. (1965) Science. 148:1471-3) shows a major and significant alteration in serum lipoprotein profile including a large reduction in triglyceride and VLDL levels. In addition, these animals have a large decrease in liver content of cholesterol esters. In accordance therewith, effective inhibition of SCD1 activity would lead to a reduction in triglyceride levels, due to decreased availability of monounsaturated fatty acids. Monounsaturated fatty acids are the preferred substrate for the enzyme responsible for triglyceride (TG) synthesis from fatty acids and glycerol phosphate (viz., glycerol phosphate acyl transferase (GPAT)).

Also in accordance with the disclosure herein, increased esterification of cholesterol prevents the toxic accumulation of free cholesterol in liver, and the increase in the availability of cholesterol esters and triglycerides also facilitates their secretion in the form of VLDL. Increased cholesterol esterification in macrophages may also enhance the formation of foam cells and thereby contribute to atherosclerotic lesion development. Thus, the inhibition of SCD activity may have the added effect of reducing the level of VLDL particles in the bloodstream and inhibiting atherosclerosis.

Further in accordance with the present invention, inhibition of SCD1 is also advantageous in increasing the formation of HDL at peripheral tissues. In a healthy individual, cellular cholesterol is predominantly in the esterified form, with low levels of free cholesterol. Acyl-CoA:cholesterol acyltransferase (ACAT) is the enzyme responsible for esterifying cholesterol using monounsaturated fatty acyl-CoA's as a preferred substrate. SCD generates the monounsaturated products, which are then available for cholesterol esterification by ACAT. The increased flux of free cholesterol out of cells and through HDL is thought to be therapeutically beneficial because it would signify enhanced "reverse cholesterol transport" (RCT).

Inhibition of SCD1 is also useful in increasing reverse cholesterol transport (RCT) without necessarily raising the serum HDL level. Serum HDL level is a surrogate marker for the process of RCT, which in fact preferably is measured by the overall flux of cholesterol from peripheral tissues to the liver. The invention identifies modulators of SCD1 biological activity as effective therapeutic agents for increasing RCT. RCT can be directly measured, for example, by injecting radiolabelled cholesterol ether incorporated into HDL particles directly into the blood, and measuring the clearance rate (the rate at which it is taken-up into the liver of an organism).

In accordance with the present invention, it has been found that modulation of SCD1 activity in the liver and other tissues results in an increase in SR-B1, a liver receptor which removes HDL from the circulation, thus increasing RCT with less obvious effects on HDL levels in the blood. The linkage between SCD1 biological activity and SR-B1 mRNA expression has not previously been identified. Previous work has established that SR-B1-overexpressing mice are cardioprotected, demonstrating reduced atherogenesis and reduced cardiovascular disease. This understanding also suggests for the first time that certain therapeutic agents, such as inhibitors of SCD1 biological activity, may increase RCT without any obvious changes on HDL levels. This is achieved by obtaining a balanced increase in both HDL formation in peripheral tissues and HDL removal by the liver.

The experiment compared SR-B1 mRNA expression in the liver of +/+ versus −/− SCD1 mice (strains as described in the Examples below). When expressed relative to the +/+ animal on chow diet the results show the following for changes in ABCA1 and SR-B1 mRNA levels:

| genotype | diet | ABC1 | SR-B1 |
|---|---|---|---|
| +/+ | Chow | 1 | 1 |
| -/- | Chow | 0.7 | 11 |
| +/+ | Hi Cholesterol | 1.1 | 27 |
| -/- | Hi Cholesterol | 0.4 | 27 |

The changes in ABC1 are not significant while those shown for SR-B1 on a chow diet are. An increase in SR-B1 expression indicates increased flux, or RCT, of cholesterol to the liver and may explain why there is no observation of elevated HDL-C in the plasma of the -/- SCD1 mouse. Increased RCT is further confirmed by the finding that -/- animals on high cholesterol diet have a gall bladder roughly 10-times the size of the +/+ animals and which are engorged with bile. These observations are consistent with increased removal of cholesterol by the liver, hence increased RCT. Further, the apparently identical increase in SR-B1 in +/+ and -/- mice may not reflect an identical phenotype or biological process in these animals.

Inhibition of SCD expression may also affect the fatty acid composition of membrane phospholipids, as well as triglycerides and cholesterol esters. The fatty acid composition of phospholipids ultimately determines membrane fluidity, while the effects on the composition of triglycerides and cholesterol esters can affect lipoprotein metabolism and adiposity.

The present invention also relates to the involvement of SCD1 in other human disorders or conditions relating to serum levels of HDL, LDL, and total cholesterol as well as the role of SCD1 in other human disorders or conditions relating to the production of secretions from mucous membranes, monounsaturated fatty acids, wax esters, and the like. The invention encompasses modulators of SCD1 that are useful for treating these disorders.

Previous work not using human subjects has shown that aberrant SCD biological activity in those organisms (but not specifying which isoform of SCD was responsible) may be implicated in various skin diseases, as well as such diverse maladies as cancer and multiple sclerosis, non-insulin-dependent diabetes mellitus, hypertension, neurological diseases, skin diseases, eye diseases, immune disorders, and cancer. Modulators discovered using the processes of the present invention would thereby also find use in treating those diseases and disorders in human subjects.

In Example 4, transcription regulating proteins for SCD1 are identified. These proteins are targets for compounds that increase or decrease SCD1 expression in cells, thereby influencing, either positively or negatively, SCD1 biological activity of cells. PPAR-gamma and SREBP are examples. Compounds which are known to act through such transcription regulators may now be identified as relevant for treating the SCD1 related diseases and disorders now identified in humans.

Screening Assays

The present invention provides screening assays employing the hSCD1 gene and/or protein for use in identifying therapeutic agents for use in treating a disorder or condition relating to serum levels of triglyceride, VLDL, HDL, LDL, total cholesterol, reverse cholesterol transport, the production of secretions from mucous membranes, monounsaturated fatty acids, wax esters, and the like.

"SCD1 Biological Activity"

"SCD1 biological activity" as used herein, especially relating to screening assays, is interpreted broadly and contemplates all directly or indirectly measurable and identifiable biological activities of the SCD1 gene and protein. Relating to the purified SCD1 protein, SCD1 biological activity includes, but is not limited to, all those biological processes, interactions, binding behavior, binding-activity relationships, pKa, pD, enzyme kinetics, stability, and functional assessments of the protein. Relating to SCD1 biological activity in cell fractions, reconstituted cell fractions or whole cells, these activities include, but are not limited the rate at which the SCD introduces a cis-double bond in its substrates palmitoyl-CoA (16:0) and stearoyl-CoA (18:0), which are converted to palmitoleoyl-CoA (16:1) and oleoyl-CoA (18:1), respectively, and all measurable consequences of this effect, such as triglyceride, cholesterol, or other lipid synthesis, membrane composition and behavior, cell growth, development or behavior and other direct or indirect effects of SCD1 activity. Relating to SCD1 genes and transcription, SCD1 biological activity includes the rate, scale or scope of transcription of genomic DNA to generate RNA; the effect of regulatory proteins on such transcription, the effect of modulators of such regulatory proteins on such transcription; plus the stability and behavior of mRNA transcripts, post-transcription processing, mRNA amounts and turnover, and all measurements of translation of the mRNA into polypeptide sequences. Relating to SCD1 biological activity in organisms, this includes but is not limited biological activities which are identified by their absence or deficiency in disease processes or disorders caused by aberrant SCD1 biological activity in those organisms. Broadly speaking, SCD1 biological activity can be determined by all these and other means for analyzing biological properties of proteins and genes that are known in the art.

The screening assays contemplated by the present invention may also employ isoforms of SCD from humans or other organisms that demonstrate similar biological activity as hSCD1 so long as they succeed in identifying therapeutic agents for human diseases. The functional equivalency of delta-9 desaturases from vertebrates has been recognized by those in the art. Consequently, specific embodiments of the present invention may employ one or more functionally equivalent delta-9 desaturase enzymes from another vertebrate species to identify therapeutic agents useful for humans. Functionally equivalent desaturases include all of the mouse, rat, cow, pig or chicken SCDs identified above, in addition to the genes identified at the UniGene Cluster Hs. 119597 SCD for Stearoyl-CoA desaturase (delta-9-desaturase). See also LocusLink: 6319; OMIM: 604031 or HomoloGene: Hs. 119597. Other known delta-9 desaturases include pig: 002858 (swiss-prot); and cow: AF188710 (NCBI, [6651449, Genbank])

Selected model Organism Protein Similarities (organism, protein reference and percent identity and length of aligned amino acid (aa) region)

| | | |
|---|---|---|
| H. sapiens: | SP: O00767- | 100%/358 aa |
| M. musculus: | PIR: A32115- | 83%/357 aa |
| R. norvegicus: | SP: P07308- | 84%/357 aa |
| D. melanogaster: | PID: g1621653- | 57%/301 aa |
| C. elegans: | PID: g3881877- | 52%/284 aa |
| S. cerevisiae: | PID: e243949- | 36%/291 aa |
| B. Taurus | O02858 | 85%/359 aa |
| S. Scrofa | 6651449 | 86%/334 aa |

Design and Development of SCD Screening Assays

The present disclosure facilitates the development of screening assays that may be cell based, cell extract (i.e. microsomal assays), cell free (i.e. transcriptional) assays, and assays of substantially purified protein activity. Such assays are typically radioactivity or fluorescence based (i.e. fluorescence polarization or fluorescence resonance energy transfer or FRET), or they may measure cell behavior (viability, growth, activity, shape, membrane fluidity, temperature sensitivity etc). Alternatively, screening may employ multicellular organisms, including genetically modified organisms such as knock-out or knock-in mice, or naturally occurring genetic variants. Screening assays may be manual or low throughput assays, or they may be high throughput screens which are mechanically/robotically enhanced.

The aforementioned processes afford the basis for screening processes, including high throughput screening processes, for determining the efficacy of potential therapeutic and diagnostic drugs for treating the diseases described herein, preferably diseases in which increased or decreased activity or expression of stearoyl-CoA desaturase (hSCD1 of the invention) plays a key role in mediating such disease.

As such this invention relates to a method for identifying, such as from a library of test compounds, a therapeutic agent which is useful in humans for the treatment of a disorder or condition relating to serum levels of triglyceride, VLDL, HDL, LDL, total cholesterol or production of secretions from mucous membranes, monounsaturated fatty acids, wax esters, and the like, comprising
  a) providing a screening assay having SCD1 biological activity;
  b) contacting said screening assay with a test compound; and
  c) subsequently measuring said biological activity;
  wherein a test compound which modulates said biological activity is said therapeutic agent, or an analog thereof.

In one aspect, the present invention relates to a process for identifying, from a library of test compounds, a therapeutic agent which is useful in humans for the treatment of a disorder or condition relating to serum levels of triglyceride or very low density lipoprotein (VLDL) comprising
  a) providing a screening assay having stearoyl-Coenzyme A desaturase type 1 (SCD1) biological activity as a component thereof;
  b) contacting said SCD1 activity with a test compound;
  c) administering to a human a compound found to modulate said activity in (b); and
  (d) detecting a change in serum level of triglyceride or VLDL in said human following said administering;
  thereby identifying an agent useful in the treatment of a disorder or condition relating to serum levels of triglyceride or very low density lipoprotein (VLDL).

In one embodiment, said agent is an antagonist or inhibitor of SCD1 biological activity. In another specific embodiment thereof, said agent is an agonist of SCD1 biological activity.

In another embodiment, where said modulator is an inhibitor, said inhibitor does not substantially inhibit the biological activity in a human of a delta-5 desaturase, delta-6 desaturase or fatty acid synthetase In one embodiment of the present invention, the assay process further comprises the step of assaying said therapeutic agent to further select compounds which do not substantially inhibit in a human the activity of delta-5 desaturase, delta-6 desaturase or fatty acid synthetase.

In specific embodiments, the present invention also encompasses a process wherein said SCD1 biological activity is measured by an assay selected from among:

a) SCD1 polypeptide binding affinity;
b) SCD1 desaturase activity in microsomes;
c) SCD1 desaturase activity in a whole cell assay
d) quantification of SCD1 gene expression level; and
e) quantification of SCD1 protein level.

Specific embodiments of such an assay may employ a recombinant cell as disclosed herein.

The present invention also relates to a process wherein the identified compound is further selected from among those compounds that do not substantially inhibit in humans the biological activity of delta-5 desaturase, delta-6 desaturase or fatty acid synthetase.

In other specific embodiments, the present invention contemplates employing SCD1 nucleic acid as disclosed herein and/or SCD1 polypeptide as disclosed herein for use in identifying compounds useful for treatment of a disorder or condition relating to serum levels of triglyceride or VLDL.

The assays disclosed herein essentially require the measurement, directly or indirectly, of an SCD1 biological activity. Those skilled in the art can develop such assays based on well known models, and many potential assays exist. For measuring whole cell activity of SCD1 directly, methods that can be used to quantitatively measure SCD activity include for example, measuring thin layer chromatographs of SCD reaction products over time. This method and other methods suitable for measuring SCD activity are well known (Henderson Henderson R J, et al. 1992. Lipid Analysis: A Practical Approach. Hamilton S. Eds. New York and Tokyo, Oxford University Press. pp 65-111. ) Gas chromatography is also useful to distinguish mononunsaturates from saturates, for example oleate (18:1) and stearate (18:0) can be distinguished using this method. A description of this method is in the examples below. These techniques can be used to determine if a test compound has influenced the biological activity of SCD1, or the rate at which the SCD introduces a cis-double bond in its substrate palmitate (16:0) or stearate (18:0) to produce palmitolyeoyl-CoA (16:1) or oleyoyl-CoA (18: 1), respectively.

In a preferred embodiment, the invention employs a microsomal assay having a measurable SCD1 biological activity. A suitable assay may be taken by modifying and scaling up the rat liver microsomal assay essentially as described by Shimomura et al. (Shimomura, I., Shimano, H., Korn, B. S., Bashmakov, Y., and Horton, J. D. (1998). Tissues are homogenized in 10 vol. of buffer A (0.1M potassium buffer, pH 7.4). The microsomal membrane fractions (100,000×g pellet) are isolated by sequential centrifugation. Reactions are performed at 37° C. for 5 min with 100 µg of protein homogenate and 60 µM of [1-$^{14}$C]-stearoyl-CoA (60,000 dpm), 2 mM of NADH, 0.1M of Tris/HCl buffer (pH 7.2). After the reaction, fatty acids are extracted and then methylated with 10% acetic chloride/methanol. Saturated fatty acid and monounsaturated fatty acid methyl esters are separated by 10% AgNO$_3$-impregnated TLC using hexane/diethyl ether (9:1) as developing solution. The plates are sprayed with 0.2 % 2',7'-dichlorofluorescein in 95% ethanol and the lipids are identified under UV light. The fractions are scraped off the plate, and the radioactivity is measured using a liquid scintillation counter.

Specific embodiments of such SCD1 biological activity assay take advantage of the fact that the SCD reaction produces, in addition to the monounsaturated fatty acyl-CoA product, H$_2$O. If 3H is introduced into the C-9 and C-10 positions of the fatty-acyl-CoA substrate, then some of the radioactive protons from this reaction will end up in water. Thus, the measurement of the activity would involve the measurement of radioactive water. In order to separate the labeled water from the stearate, investigators may employ substrates such as charcoal, hydrophobic beads, or just plain old-fashioned solvents in acid pH.

In a preferred embodiment, screening assays measure SCD1 biological activity indirectly. Standard high-throughput screening assays centre on ligand-receptor assays. These may be fluorescence based or luminescence based or radiolabel detection. Enzyme immunoassays can be run on a wide variety of formats for identifying compounds that interact with SCD1 proteins. These assays may employ prompt fluorescence or time-resolved fluorescence immunoassays which are well known. $P^{32}$ labeled ATP, is typically used for protein kinase assays. Phosphorylated products may be separated for counting by a variety of methods. Scintillation proximity assay technology is an enhanced method of radiolabel assay. All these types of assays are particularly appropriate for assays of compounds that interact with purified or semi-purified SCD1 protein.

In a preferred embodiment, the assay makes use of $^3$H-stearoyl CoA (with the $^3$H on the 9 and 10 carbon atoms), the substrate for SCD1. Desaturation by SCD1, produces oleoyl CoA and 3H-water molecules. The reaction is run at room temperature, quenched with acid and then activated charcoal is used to separate unreacted substrate from the radioactive water product. The charcoal is sedimented and amount of radioactivity in the supernatant is determined by liquid scintillation counting. This assay is specific for SCD1-dependent desaturation as judged by the difference seen when comparing the activity in wild type and SCD1-knockout tissues. Further, the method is easily adapted to high throughput as it is cell-free, conducted at room temperature and is relatively brief (1 hour reaction time period versus previous period of 2 days). This procedure is illustrated more fully in FIGS. 17 to 20.

While the instant disclosure sets forth an effective working embodiment of the invention, those skilled in the art are able to optimize the assay in a variety of ways, all of which are encompassed by the invention. For example, charcoal is very efficient (>98%) at removing the unused portion of the stearoyl-CoA but has the disadvantage of being messy and under some conditions difficult to pipette. It may not be necessary to use charcoal if the stearoyl-CoA complex sufficiently aggregates when acidified and spun under moderate g-force. This can be tested by measuring the signal/noise ratio with and without charcoal following a desaturation reaction. There are also other reagents that would efficiently sediment stearoyl-CoA to separate it from the $^3$H-water product.

Figure 20:
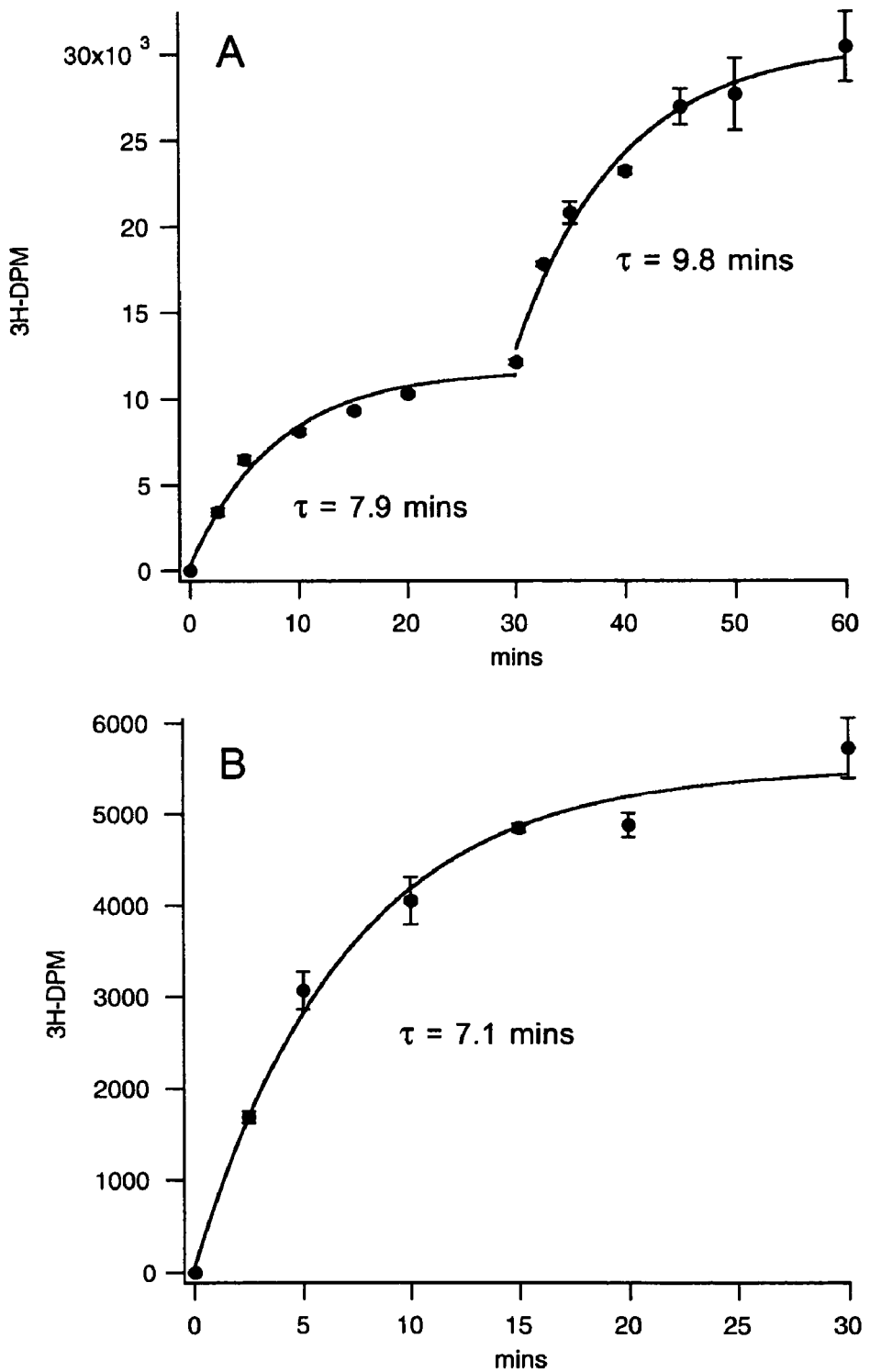
FIG. 20 (A) Demonstration that stearoyl-CoA mass limits the kinetics and magnitude of the $^3$H-production signal we are taking as a measure of SCD1-dependent desaturation. This experiment is essentially a repeat of that shown in FIG. 17 with the exception that at 30 mins an additional aliquot of stearoyl-CoA mass/radioactivity was added, resulting in the second exponential production of $^3$H signal. This shows that the amount of stearoyl-CoA limits the reaction as expected for SCD1-catalyzed desaturation. (B) Demonstration that the experiment is adaptable to high throughput. All previous experiments were done where the total reaction volume was 1.1 ml (0.2 ml reaction buffer containing microsomes, 0.2 ml 6% PCA to quench the reaction and 0.7 ml 10% charcoal solution to sediment the unreacted substrate). The experiment illustrated in B was done with a total reaction volume of 0.31 ml (0.1 ml reaction buffer with microsomes, 0.01 ml 60% PCA to quench and 0.2 ml 10% charcoal to sediment).

As shown in FIG. 20 (Panel A) the amount of stearoyl-CoA limits the kinetics and magnitude of the $^3$H-DPM signal monitored as SCD1-dependent desaturation activity. However, not all of the stearoyl-CoA was consumed by SCD1; >90% remains unavailable to SCD1 either because other enzymes present in the microsomes (e.g., acyl transferase reactions) utilize it as a substrate and compete with SCD1 and/or stearoyl-CoA is unstable under the conditions of the experiment. These possibilities may be examined by monitoring incorporation of the label into phospholipids or by including a buffer mixture (Mg++, ATP and CoA) that would regenerate stearoyl-CoA from stearate and CoA.

As shown in FIG. 20 (Panel B) the assay can be done in a small volume appropriate for high throughput screening. A preferred embodiment would employ a microcentrifuge satisfactory for spinning 96 well plates.

The following assays are also suitable for measuring SCD1 biological activity in the presence of potential therapeutic agents. These assays are also valuable as secondary screens to further select SCD1 specific modulators, inhibitors or agonists from a library of potential therapeutic agents.

Cellular based desaturation assays can also be used. By tracking the conversion of stearate to oleate in cells (3T3L1 adipocytes are known to have high SCD1 expression and readily take up stearate when complexed to BSA) we can evaluate compounds found to be inhibitory in the primary screen for additional qualities or characteristics such as whether they are cell permeable, lethal to cells, and/or competent to inhibit SCD1 activity in cells. This cellular based assay may employ a recombinant cell line containing a delta-9 desaturase, preferably hSCD1 (human SCD1). The recombiant gene is optionally under control of an inducible promoter and the cell line preferably over-expresses SCD1 protein.

Other assays for tracking other SCD isoforms could be developed. For example, rat and mouse SCD2 is expressed in brain. In a preferred embodiment, a microsome preparation is made from the brain as previously done for SCD1 from liver. The object may be to find compounds that would be specific to SCD1. This screen would compare the inhibitory effect of the compound for SCD1 versus SCD2.

Although unlikely, it is possible that a compound "hit" in the SCD1 assay may result from stimulation of an enzyme present in the microsome preparation that competitively utilizes stearoyl-CoA at the expense of that available for SCD1-dependent desaturation. This would mistakenly be interpreted as SCD1 inhibition. One possibility to examine this problem would be incorporation into phospholipids of the unsaturated lipid (stearate). By determining effects of the compounds on stimulation of stearate incorporation into lipids researchers are able to evaluate this possibility.

Cell based assays may be preferred, for they leave the SCD1 gene in its native format. Particularly promising for SCD1 analysis in these types of assays are fluorescence polarization assays. The extent to which light remains polarized depends on the degree to which the tag has rotated in the time interval between excitation and emission. Since the measurement is sensitive to the tumbling rate of molecules, it can be used to measure changes in membrane fluidity characteristics that are induced by SCD1 activity—namely the delta-9 desaturation activity of the cell. An alternate assay for SCD1 involves a FRET assay. FRET assays measure fluorescence resonance energy transfer which occurs between a fluorescent molecule donor and an acceptor, or quencher. Such an assay may be suitable to measure changes in membrane fluidity or temperature sensitivity characteristics induced by SCD1 biological activity.

The screening assays of the invention may be conducted using high throughput robotic systems. In the future, preferred assays may include chip devices developed by, among others, Caliper, Inc., ACLARA BioSciences, Cellomics, Inc., Aurora Biosciences Inc., and others.

In other embodiments of the present invention, SCD1 biological activity can also be measured through a cholesterol efflux assay that measures the ability of cells to transfer cholesterol to an extracellular acceptor molecule and is dependent on ABCA1 function. A standard cholesterol efflux assay is set out in Marcil et al., Arterioscler. Thromb. Vasc. Biol. 19:159-169, 1999, incorporated by reference herein for all purposes.

Preferred assays are readily adapted to the format used for drug screening, which may consist of a multi-well (e.g., 96-well, 384 well or 1536 well or greater) format. Modification of the assay to optimize it for drug screening would include scaling down and streamlining the procedure, modifying the labeling method, altering the incubation time, and changing the method of calculating SCD1 biological activity etc. In all these cases, the SCD1 biological activity assay remains conceptually the same, though experimental modifications may be made.

Another preferred cell based assay is a cell viability assay for the isolation of SCD1 inhibitors. Overexpression of SCD decreases cell viability. This phenotype can be exploited to identify inhibitory compounds. This cytotoxicity may be due to alteration of the fatty acid composition of the plasma membrane. In a preferred embodiment, the human SCD1 cDNA would be placed under the control of an inducible promoter, such as the Tet-On Tet-Off inducible gene expression system (Clontech). This system involves making a double stable cell line. The first transfection introduces a regulator plasmid and the second would introduce the inducible SCD expression construct. The chromosomal integration of both constructs into the host genome would be favored by placing the transfected cells under selective pressure in the presence of the appropriate antibiotic. Once the double stable cell line was established, SCD1 expression would be induced using the tetracycline or a tetracycline derivative (eg. Doxycycline). Once SCD1 expression had been induced, the cells would be exposed to a library of chemical compounds for HTS of potential inhibitors. After a defined time period, cell viability would then be measured by means of a fluorescent dye or other approach (e.g. turbidity of the tissue culture media). Those cells exposed to compounds that act to inhibit SCD1 activity would show increased viability, above background survival. Thus, such an assay would be a positive selection for inhibitors of SCD1 activity based on inducible SCD1 expression and measurement of cell viability.

An alternative approach is to interfere with the desaturase system. The desaturase system has three major proteins: cytochrome $b_5$, NADH (P)-cytochrome $b_5$ reductase, and terminal cyanide-sensitive desaturase. Terminal cyanide-sensitive desaturase is the product of the SCD gene. SCD activity depends upon the formation of a stable complex between the three aforementioned components. Thus, any agent that interferes with the formation of this complex or any agent that interferes with the proper function of any of the three components of the complex would effectively inhibit SCD activity.

Another type of modulator of SCD1 activity involves a 33 amino acid destabilization domain located at the amino terminal end of the pre-SCD1 protein (Mziaut et al., PNAS 2000, 97: p 8883-8888). It is possible that this domain may be cleaved from the SCD1 protein by an as yet unknown protease. This putative proteolytic activity would therefore act to increase the stability and half-life of SCD1. Inhibition of the putative protease, on the other hand, would cause a decrease in the stability and half life of SCD1. Compounds which block or modulate removal of the destabilization domain therefore will lead to reductions in SCD1 protein levels in a cell. Therefore, in certain embodiments of the invention, a screening assay will employ a measure of protease activity to identify modulators of SCD1 protease activity. The first step is to identify the specific protease which is responsible for cleavage of SCD1. This protease can then be integrated into a screening assay. Classical protease assays often rely on splicing a protease cleavage site (i.e., a peptide containing the cleavable sequence pertaining to the protease in question) to a protein, which is deactivated upon cleavage. A tetracycline efflux protein may be used for this purpose. A chimera containing the inserted sequence is expressed in E. coli. When the protein is cleaved, tetracycline resistance is lost to the bacterium. In vitro assays have been developed in which a peptide containing an appropriate cleavage site is immobilized at one end on a solid phase. The other end is labeled with a radioisotope, fluorophore, or other tag. Enzyme-mediated loss of signal from the solid phase parallels protease activity. These techniques can be used both to identify the protease responsible for generating the mature SCD1 protein, and also for identifying modulators of this protease for use in decreasing SCD1 levels in a cell.

In another aspect, the present invention relates to a process for determining the ability of an agent to modulate the activity of a human stearoyl-CoA desaturase, comprising the steps of:
  (a) contacting the agent under suitable conditions with the human stearoyl-CoA desaturase of the invention at a predetermined level of said agent;
  (b) determining if the activity of said stearoyl-CoA desaturase changes after said contact,
  thereby determining if said agent has modulated said activity.

Such an assay may be carried out as a cell free assay employing a cellular fractional, such as a microsomal fraction, obtained by conventional methods of differential cellular fractionation, most commonly by ultracentrifugation methods. In specific embodiments, such modulation may be an increase or decrease in the activity of the desaturase.

These results suggest that inhibitors of SCD biological activity, such as hSCD1, in a human, may have the beneficial effect of reducing triglycerides and/or increasing HDL levels. In addition, increased SCD activity is also associated with increased body weight index. This result identifies hSCD1 as a useful target for identifying agents for modulating obesity and related conditions. In these human data results, SCD biological activity was measured via the surrogate marker of the ratio of 18:1 to 18:0 fatty acids in the total plasma lipid fraction. This marker indirectly measures hSCD1 biological activity.

In a further aspect, the present invention relates to a process for determining the ability of an agent to modulate the activity of a human stearoyl-CoA desaturase in cells expressing the human stearoyl-CoA desaturase of the invention, comprising the steps of:
  (a) contacting the agent under suitable conditions with a eukaryotic cell expressing the human stearoyl-CoA desaturase of the invention at a predetermined level of said agent and under conditions where said agent may or may not modulate the expression level of said desaturase;
  (b) determining if the activity of said stearoyl-CoA desaturase changes after said contact,
  thereby determining if said agent has modulated said expression level.

In specific embodiments of said processes, the modulation may be an increase or decrease in activity of the desaturase and cells useful in these processes are preferably mammalian cells, most preferably human cells, and include any of the recombinant cells disclosed herein.

SCD1 Recombinant Cell Lines

In certain embodiments, the present invention contemplates use of a SCD1 gene or protein in a recombinant cell line. SCD1 recombinant cell lines may be generated using techniques known in the art, and those more specifically set out below.

The present invention also relates to vectors which contain polynucleotides of the present invention, and host cells which are genetically engineered with vectors of the invention, especially where such cells result in a cell line that can be used for assay of hSCD1 activity, and production of SCD1 polypeptides by recombinant techniques.

Host cells are preferably eukaryotic cells, preferably insect cells of *Spodoptera* species, most especially SF9 cells. Host cells are genetically engineered (transduced or transformed or transfected) with the vectors, especially baculovirus) of this invention which may be, for example, a cloning vector or an expression vector. Such vectors can include plasmids, viruses and the like. The engineered host cells are cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein. Such transformation will be permanent and thus give rise to a cell line that can be used for further testing. Such cell lines used for testing will commonly be mammalian cells, especially human cells.

As representative examples of appropriate hosts, there may be mentioned *Spodoptera* Sf9 (and other insect expression systems) and animal cells such as CHO, COS or Bowes melanoma; adenoviruses; plant cells, and even bacterial cells, etc, all of which are capable of expressing the polynucleotides disclosed herein. The selection of an appropriate host is deemed to be within the knowledge of those skilled in the art based on the teachings herein. For use in the assay methods disclosed herein, mammalian, especially human, cells are preferred.

More particularly, the present invention also includes recombinant constructs comprising one or more of the sequences as broadly described above. The constructs comprise a vector, such as a plasmid or viral vector, especially where the Baculovirus/SF9 vector/expression system is used, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); pTRC99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacd, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)). A preferred embodiment utilizes expression from insect cells, especially SF9 cells from *Spodoptera frugiperda*.

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), Wu et al, Methods in Gene Biotechnology (CRC Press, New York, N.Y., 1997), Recombinant Gene Expression Protocols, in Methods in Molecular Biology, Vol. 62, (Tuan, ed., Humana Press, Totowa, N.J., 1997), and Current Protocols in Molecular Biology, (Ausabel et al, Eds.,), John Wiley & Sons, NY (1994-1999), the disclosures of which are hereby incorporated by reference in their entirety.

Transcription of the DNA encoding the polypeptides of the present invention by eukaryotic cells, especially mammalian cells, most especially human cells, is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* Trp1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal or C-terminal identification peptide imparting desired characteristics, e.g., stabilization or simplified purification of expressed recombinant product.

Use of a Baculovirus-based expression system is a preferred and convenient method of forming the recombinants disclosed herein. Baculoviruses represent a large family of DNA viruses that infect mostly insects. The prototype is the nuclear polyhedrosis virus (ACMNPV) from *Autographa californica*, which infects a number of lepidopteran species. One advantage of the baculovirus system is that recombinant baculoviruses can be produced in vivo. Following co-transfection with transfer plasmid, most progeny tend to be wild type and a good deal of the subsequent processing involves screening. To help identify plaques, special systems are available that utilize deletion mutants. By way of non-limiting example, a recombinant AcMNPV derivative (called Bac-PAK6) has been reported in the literature that includes target sites for the restriction nuclease Bsu361 upstream of the polyhedrin gene (and within ORF 1629) that encodes a capsid gene (essential for virus viability). Bsf36I does not cut elsewhere in the genome and digestion of the BacPAK6 deletes a portion of the ORF1629, thereby rendering the virus non-viable. Thus, with a protocol involving a system like Bsu361-cut BacPAK6 DNA most of the progeny are non-viable so that the only progeny obtained after co-transfection of transfer plasmid and digested BacPAK6 is the recombinant because the transfer plasmid, containing the exogenous DNA, is inserted at the Bsu36I site thereby rendering the recombinants resistant to the enzyme. [see Kitts and Possee, A method for producing baculovirus expression vectors at high frequency, BioTechniques, 14, 810-817 (1993). For general procedures, see King and Possee, The Baculovirus Expression System: A Laboratory Guide, Chapman and Hall, New York (1992) and Recombinant Gene Expression Protocols, in Methods in Molecular Biology, Vol. 62, (Tuan, ed., Humana Press, Totowa, N.J., 1997), at Chapter 19, pp. 235-246.

In accordance with the foregoing, the present invention further relates to vectors comprising a polynucleotide of the invention and to recombinant eukaryotic cells expressing the stearoyl-CoA desaturase of the present invention, preferably wherein said cell is a mammalian cell, most preferably a human cell.

The present invention further relates to processes for using the polynucleotides, enzymes, and cells disclosed herein in a process for determining the ability of an agent to modulate the expression of said human stearoyl-CoA desaturase in cells expressing said human stearoyl-CoA desaturase of the invention, comprising the steps of:

(a) contacting the agent under suitable conditions with a eukaryotic cell expressing the human stearoyl-CoA desaturase of the invention at a predetermined level of said agent;

(b) determining if the expression level of said stearoyl-CoA desaturase changes after said contact, thereby determining if said agent has modulated said expression level.

Alternatively, the screening assay may employ a vector construct comprising the hSCD1 promoter sequence of SEQ ID. No. 3 operably linked to a reporter gene. Such a vector can be used to study the effect of potential transcription regulatory proteins, and the effect of compounds that modulate the effect of those regulatory proteins, on the transcription of SCD1. An example of this type of vector is the pSCD-500 plasmid described in the examples below. Reporter gene constructs such as this are commonly used to indicate whether a test compound has succeeded in activating the transcription of genes under the control of a particular promoter.

In specific embodiments, the present invention contemplates a process wherein said modulation is an increase or decrease in said expression level and where said cell may be a mammalian cell, especially a human cell, including any of the recombinant cells disclosed herein. In one embodiment, the expression level is determined by determining the level of messenger RNA produced after contact of said cell with said agent.

Factors that may modulate gene expression include transcription factors such as, but not limited to, retinoid X receptors (RXRs), peroxisomal proliferation-activated receptor (PPAR) transcription factors, the steroid response element binding proteins (SREBP-1 and SREBP-2), REV-ERBα, ADD-1, EBPα, CREB binding protein, P300, HNF 4, RAR, LXR, and RORα, NF-Y, C/EBPalpha, PUFA-RE and related proteins and transcription regulators. Screening assays designed to assess the capacity of test compounds to modulate the ability of these transcription factors to transcribe SCD1 are also contemplated by this invention.

Physiological benefits of an increase or decrease in the activity or expression of hSCD1 include, but are not limited to, decreased plasma triglycerides and/or increased plasma HDL leading to cardioprotective benefit, therapeutic benefit in Type II diabetes, weight loss, improved gland secretions, and decreased chance of malignancy. Thus, the determination of the ability of agents to modulate such activity or expression affords an opportunity to discover useful therapeutic agents producing such effects.

In addition, variations in hSCD1 gene expression, function, stability, catalytic activity and other characteristics may be due to allelic variations in the polynucleotide sequences encoding such enzymes. The processes disclosed according to the present invention may likewise be used to determine such genomic effects on expression of hSCD1. Using the processes of the present invention, such variations may be determined at the level of DNA polymorphism within the hSCD1 gene and/or promoter sequences. Such effects lead to the elucidation of associations between such polymorphisms and predisposition to cancer, neurological disease, skin disease, obesity, diabetes, immune function and lipid metabolism through both population and family-based genetic analysis.

Finally, those skilled in the art are able to confirm the relevance of hSCD1 to human health by analogy to animal models. Well known animal disease models may be used to ascertain the effect of an hSCD1 modulator on the growth, development, or disease process in these animals. Additionally, models include genetically modified multicellular animals, such as knock-out or knock-in mice (as detailed in the examples below).

In a general aspect, the present invention relates to a process for identifying a SCD1-modulating agent, comprising:
 a) contacting under physiological conditions a chemical agent and a molecule having or inducing SCD1 activity;
 b) detecting a change in the activity of said molecule having or inducing SCD1 activity following said contacting;
 thereby identifying an SCD1 modulating agent.

In specific embodiments of the invention, said molecule having or inducing SCD1 activity is a polypeptide having such activity, or a polynucleotide encoding a polypeptide having such activity, or a polypeptide modulating the activity of a polynucleotide encoding a polypeptide having such activity.

In specific embodiments, said change in activity is an increase in activity or is a decrease in activity.

In addition, said contacting may be accomplished in vivo. In one such embodiment, said contacting in step (a) is accomplished by administering said chemical agent to an animal afflicted with a triglyceride (TG)- or very low density lipoprotein (VLDL)-related disorder and subsequently detecting a change in plasma triglyceride level in said animal thereby identifying a therapeutic agent useful in treating a triglyceride (TG)- or very low density lipoprotein (VLDL)-related disorder. In such embodiment, the animal may be a human, such as a human patient afflicted with such a disorder and in need of treatment of said disorder.

In specific embodiments of such in vivo processes, said change in SCD1 activity in said animal is a decrease in activity, preferably wherein said SCD1 modulating agent does not substantially inhibit the biological activity of a delta-5 desaturase, delta-6 desaturase or fatty acid synthetase.

In such processes as just disclosed, the detected change in SCD1 activity is detected by detecting a change in any, some or all of the following:
 a) SCD1 polypeptide binding affinity;
 b) SCD1 desaturase activity in microsomes;
 c) SCD1 desaturase activity in a whole cell;
 d) SCD1 gene expression; or
 e) SCD1 protein level.

In accordance with the foregoing, the present invention is also directed to a recombinant cell line comprising a recombinant SCD1 protein as disclosed herein. In one such embodiment, the whole cell of (c) above is derived from such a cell line, preferably wherein said SCD1 modulating agent does not substantially inhibit in humans the biological activity of delta-5 desaturase, delta-6 desaturase or fatty acid synthetase.

A recombinant cell line of the invention may also comprise the SCD1 promoter nucleic acid sequence of SEQ ID No. 1 operably linked to a reporter gene construct. In a specific embodiment thereof, the whole cell of (c) above is derived from a recombinant cell of such a cell line.

In accordance with the disclosure herein, the present invention is also directed to an isolated stearoyl-CoA desaturase encoded by the polynucleotide sequence comprising SEQ ID No. [SCD1 cDNA] as well as a reporter gene construct comprising the SCD1 promoter nucleic acid sequence of SEQ ID No. 1 operably linked to a reporter gene, advantageously including usable vectors comprising such the nucleic acids and constructs thereof. Likewise, the present invention also contemplates an isolated polypeptide having stearoyl-CoA reductase activity and a process as disclosed herein that successfully identifies a chemical agent that binds to or interacts with such a polypeptide, which process comprises:
 a) contacting such a polypeptide, or a cell expressing such polypeptide, with a chemical agent; and
 b) detecting binding or interaction of the chemical agent with said polypeptide.

In specific embodiments of the process just described, the binding of the chemical agent to the polypeptide is detected by a method selected from the group consisting of:
 a) direct detection of chemical agent/polypeptide binding;
 b) detection of binding by competition binding assay; and
 c) detection of binding by assay for SCD1 biological activity.

In such processes, modulation of the activity of such polypeptide is detected by a process comprising contacting the polypeptide or a cell expressing the polypeptide with a compound that binds to the polypeptide in sufficient amount to modulate the activity of the polypeptide. In specific embodiments of this process, the molecule having or inducing SCD1 activity is selected from the group consisting of an SCD1 nucleic acid and/or SCD1 polypeptide as disclosed herein.

In accordance with the foregoing, following identification of chemical agents having the desired modulating activity, the present invention also relates to a process for treating an animal, especially a human, such as a human patient, afflicted with a disease or condition relating to serum levels of triglyceride or VLDL comprising inhibiting SCD1 activity in said human. In a preferred embodiment, said inhibition of SCD1 activity is not accompanied by substantial inhibition of activity of delta-5 desaturase, delta-6 desaturase or fatty acid synthetase. In a specific embodiment, the present invention relates to a process for treating a human patient afflicted with a disorder or condition relating to serum levels of triglyceride or VLDL comprising administering to said patient a therapeutically effective amount of an agent whose therapeutic activity was first identified by the process of the invention.

In accordance with the foregoing, the present invention also relates to a modulator of SCD1 activity and which is useful in humans for treatment of a disorder or condition relating to serum levels of triglyceride or VLDL wherein said activity was first identified by its ability to modulate SCD1 activity, especially where such modulation was first detected using a process as disclosed herein according to the present invention. In a preferred embodiment thereof, such modulating agent does not substantially inhibit fatty acid synthetase, delta-5 desaturase or delta-6 desaturase of humans.

Thus, the present invention also relates to a process for identifying a vertebrate delta-9 stearoyl-CoA desaturase-modulating agent, comprising:
 a) contacting under physiological conditions a chemical agent and a molecule having or inducing vertebrate delta-9 stearoyl-CoA desaturase activity;
 b) detecting a change in the activity of said molecule having or inducing vertebrate delta-9 stearoyl-CoA desaturase activity following said contacting;
 thereby identifying a vertebrate delta-9 stearoyl-CoA desaturase modulating agent.

In a specific embodiment of such process, the contacting in step (a) is accomplished by administering said chemical agent to an animal afflicted with a disorder or condition related to serum levels of triglyceride, VLDL, HDL, LDL, total cholesterol, reverse cholesterol transport or production or secretion of mucous membranes, monounsaturated fatty acids, wax esters, and like parameters, detecting a change in the activity of said molecule having or inducing vertebrate delta-9 stearoyl-CoA desaturase activity following said contacting and thereby identifying a therapeutic agent useful in treating a triglyceride, VLDL, HDL, LDL, total cholesterol, reverse cholesterol transport or production or secretion of mucous membranes, monounsaturated fatty acids, wax esters, and like disease-related disorder.

In accordance with the foregoing, the present invention further relates to a process for treating a human patient afflicted with a disease or condition relating to serum levels of triglyceride, VLDL, HDL, LDL, total cholesterol, reverse cholesterol transport or production or secretion of mucous membranes, monounsaturated fatty acids, wax esters, and like parameters, comprising administering to said human patient a therapeutically effective amount of an agent for which such therapeutic activity was identified by a process as disclosed herein according to the invention.

In a preferred embodiments of such process, the modulating agent does not substantially inhibit fatty acid synthetase, delta-5 desaturase or delta-6 desaturase of humans.

Test Compounds/Modulators/Library Sources

In accordance with the foregoing, the present invention also relates to therapeutic and/or diagnostic agents, regardless of molecular size or weight, effective in treating and/or diagnosing and/or preventing any of the diseases disclosed herein, preferably where such agents have the ability to modulate activity and/or expression of the hSCD1 disclosed herein, and most preferably where said agents have been determined to have such activity through at least one of the screening assays disclosed according to the present invention.

Test compounds are generally compiled into libraries of such compounds, and a key object of the screening assays of the invention is to select which compounds are relevant from libraries having hundreds of thousands, or millions of compounds having unknown therapeutic efficacy.

Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

Thus, in one aspect the present invention relates to agents capable of modulating the activity and/or expression of human stearoyl-CoA desaturase 1 (hSCD1) as disclosed herein, especially where said modulating ability was first determined using an assay of comprising hSCD1or a gene encoding hSCD1, or an assay which measures hSCD1 activity. As used herein the term "capable of modulating" refers to the characteristic of such an agent whereby said agent has the effect of changing the overall biological activity of hSCD1, either by increasing or decreasing said activity, under suitable conditions of temperature, pressure, pH and the like so as to facilitate such modulation to a point where it can be detected either qualitatively or quantitatively and wherein such modulation may occur in either an in vitro or in vivo environment. In addition, while the term "modulation" is used herein to mean a change in activity, more specifically either an increase or decrease in such activity, the term "activity" is not to be limited to specific enzymatic activity alone (for example, as measured in units per milligram or some other suitable unit of specific activity) but includes other direct and indirect effects of the protein, including increases in enzyme activity due not to changes in specific enzyme activity but due to changes (i.e., modulation) of expression of polynucleotides encoding and expressing said hSCD1 enzyme. Human SCD1 activity may also be influenced by agents which bind specifically to substrates of hSCD1. Thus, the term "modulation" as used herein means a change in hSCD1 activity regardless of the molecular genetic level of said modulation, be it an effect on the enzyme per se or an effect on the genes encoding the enzyme or on the RNA, especially mRNA, involved in expression of the genes encoding said enzyme. Thus, modulation by such agents can occur at the level of DNA, RNA or enzyme protein and can be determined either in vivo or ex vivo.

In specific embodiments thereof, said assay is any of the assays disclosed herein according to the invention. In addition, the agent(s) contemplated by the present disclosure includes agents of any size or chemical character, either large or small molecules, including proteins, such as antibodies, nucleic acids, either RNA or DNA, and small chemical structures, such as small organic molecules.

In other aspects, the present invention contemplates agents wherein said agent is useful in treating, preventing and/or diagnosing a disease or condition which is identified as being SCD1 related according to this invention. Specific embodiments are directed to situations wherein the disease or condition includes, but is not limited to, serum levels of triglyceride, VLDL, HDL, LDL, total cholesterol, reverse cholesterol transport or production of secretions from mucous membranes, monounsaturated fatty acids, wax esters, and the like, cholesterol disorders, lipidemias, cardiovascular disease, diabetes, obesity, baldness, skin diseases, cancer and multiple sclerosis, especially where the disease is a cardiovascular disease or a skin disease or where the condition is baldness. In a preferred embodiment, such agents will increase HDL levels in a patient and/or decrease triglyceride levels in a patient. Either or both effects are directly associated with reduced risk of cardiovascular disease and coronary artery disease.

Some of the known modulators of SCD1 activity include conjugated linoleic acid especially trans-10, cis-12 isomer, and thiazoladinedione compounds such as troglitazone.

While it is envisaged that any suitable mechanism for the inhibition or modulation of SCD1 activity can be used, three specific examples of inhibitor classes are envisioned. One class includes those inhibitors that effectively inhibit SCD1 expression, such as thiazoladinedione compounds and polyunsaturated fatty acids. A second class includes those inhibitors that effectively inhibit SCD1 enzymatic activity, such as thia-fatty acids, cyclopropenoid fatty acids, and certain conjugated linoleic acid isomers. Finally, the third class of inhibitors includes those agents that are capable of interfering with the proteins essential to the desaturase system, such as those agents that interfere with cytochrome $b_5$, NADH (P)-cytochrome $b_5$ reductase, and terminal cyanide-sensitive desaturase.

For effectively inhibiting the expression of the SCD1 gene, it is envisioned that any agent capable of disrupting the transcription of the SCD1 gene could be utilized. Since SCD1 is regulated by several known transcription factors (e.g. PPAR-γ, SREBP), any agent that affects the activity of such transcription factors can be used to alter the expression of the SCD1 gene. One group of such agents includes thiazoladine compounds which are known to activate PPAR-γ and inhibit SCD1 transcription. These compounds include Pioglitazone, Ciglitazone, Englitazone, Troglitazone, and BRL49653. Other inhibitory agents may include polyunsaturated fatty acids, such as linoleic acid, arachidonic acid and dodecahexaenoic acid, which also inhibit SCD1 transcription.

For effectively inhibiting the enzymatic activity of the SCD1 protein, it is envisaged that any agent capable of disrupting the activity of the SCD1 protein could be utilized. For example, certain conjugated linoleic acid isomers are effective inhibitors of SCD1 activity. Specifically, Cis-12, trans-10 conjugated linoleic acid is known to effectively inhibit SCD enzyme activity and reduce the abundance of SCD1 mRNA while Cis-9, trans-11 conjugated linoleic acid does not. Cyclopropenoid fatty acids, such as those found in stercula and cotton seeds, are also known to inhibit SCD activity. For example, sterculic acid (8-(2-octyl-cyclopropenyl)octanoic acid) and Malvalic acid (7-(2-octyl-cyclopropenyl)heptanoic acid) are C18 and C16 derivatives of sterculoyl- and malvaloyl fatty acids, respectively, having cyclopropene rings at their Δ9 position. These agents inhibit SCD activity by inhibiting Δ9 desaturation. Other agents include thia-fatty acids, such as 9-thiastearic acid (also called 8-nonylthiooctanoic acid) and other fatty acids with a sulfoxy moiety.

The known modulators of delta-9 desaturase activity are either not known to be useful for treating the diseases and disorders linked to SCD1 biological activity as claimed in this invention, or else they are otherwise unsatisfactory therapeutic agents. The thia-fatty acids, conjugated linoleic acids and cyclopropene fatty acids (malvalic acid and sterculic acid) are neither useful at reasonable physiological doses, nor are they specific inhibitors of SCD1 biological activity, rather they demonstrate cross inhibition of other desaturases, in particular the delta-5 and delta-6 desaturases by the cyclopropene fatty acids. These compounds may be useful for establishing control or test modulators of the screening assays of the invention, but are not subject to the claims of this invention. Preferred SCD1 modulators of the invention have no significant or substantial impact on unrelated classes of proteins. In some cases, assays specific for the other proteins, such as delta-5 and delta-6 activity, will also have to be tested to ensure that the identified compounds of the invention do not demonstrate significant or substantial cross inhibition.

The known non-specific inhibitors of SCD1 can be useful in rational design of a therapeutic agent suitable for inhibition of SCD1. All three inhibitors have various substitutions between carbons #9 and #10; additionally they require conjugation to Co-A to be effective; and are probably situated in a relatively hydrophobic active site. This information combined with the known X-ray co-ordinates for the active site for plant (soluble) SCD can assist the "in silico" process of rational drug design for therapeutically acceptable inhibitors specific for SCD1.

This invention also provides an antibody which specifically binds to human SCD1 having the amino acid sequence shown in the SwissProt accession numbers listed above, and which thereby inhibits the activity of SCD1. The instant antibody can be a polyclonal antibody, a monoclonal antibody, or an SCD-binding fragment thereof. In one embodiment, the antibody is isolated, ie.e., an antibody free of any other antibodies. Methods of making and isolating antibodies are well known in the art (Harlow, et al. 1988. Antibodies: A Laboratory Manual; Cold Spring Harbor, N.Y., Cold Spring Harbor Laboratory).

This invention also provides an antisense oligonucleotide which specifically binds to human SCD1 mRNA, and which thereby reduces the level of SCD1 gene transcription. Methods of making and using antisense molecules against known target genes are known in the art (Agarwal, S. (1996) Antisense Therapeutics. Totowa, N.J., Humana Press, Inc.)

Combinatorial and Medicinal Chemistry

Typically, a screening assay, such as a high throughput screening assay, will identify several or even many compounds which modulate the activity of the assay protein. The compound identified by the screening assay may be further modified before it is used in humans as the therapeutic agent. Typically, combinatorial chemistry is performed on the modulator, to identify possible variants that have improved absorption, biodistribution, metabolism and/or excretion, or other important therapeutic aspects. The essential invariant is that the improved compounds share a particular active group or groups which are necessary for the desired modulation of the target protein. Many combinatorial chemistry and medicinal chemistry techniques are well known in the art. Each one adds or deletes one or more constituent moieties of the compound to generate a modified analog, which analog is again assayed to identify compounds of the invention. Thus, as used in this invention, therapeutic compounds identified using an SCD1 screening assay of the invention include actual compounds so identified, and any analogs or combinatorial modifications made to a compound which is so identified which are useful for treatment of the disorders claimed herein.

Pharmaceutical Preparations and Dosages

In another aspect the present invention is directed to compositions comprising the polynucleotides, polypeptides or other chemical agents, including therapeutic, prophylactic or diagnostic agents, such as small organic molecules, disclosed herein according to the present invention wherein said polynucleotides, polypeptides or other agents are suspended in a pharmacologically acceptable carrier, which carrier includes any pharmacologically acceptable diluent or excipient. Pharmaceutically acceptable carriers include, but are not limited to, liquids such as water, saline, glycerol and ethanol, and the like, including carriers useful in forming sprays for nasal and other respiratory tract delivery or for delivery to the ophthalmic system. A thorough discussion of pharmaceutically acceptable carriers, diluents, and other excipients is presented in REMINGTON'S PHARMACEUTICAL SCIENCES (Mack Pub. Co., N.J. current edition).

The inhibitors utilized above may be delivered to a subject using any of the commonly used delivery systems known in the art, as appropriate for the inhibitor chosen. The preferred delivery systems include intravenous injection or oral delivery, depending on the ability of the selected inhibitor to be adsorbed in the digestive tract. Any other delivery system appropriate for delivery of small molecules, such as skin patches, may also be used as appropriate.

In another aspect the present invention further relates to a process for preventing or treating a disease or condition in a patient afflicted therewith comprising administering to said patient a therapeutically or prophylactically effective amount of a composition as disclosed herein.

Diagnosis & Pharmacogenomics

In an additional aspect, the present invention also relates to a process for diagnosing a disease or condition in a patient, commonly a human being, suspected of being afflicted therewith, or at risk of becoming afflicted therewith, comprising obtaining a tissue sample from said patient and determining the level of activity of hSCD1 in the cells of said tissue sample and comparing said activity to that of an equal amount of the corresponding tissue from a patient not suspected of being afflicted with, or at risk of becoming afflicted with, said disease or condition. In specific embodiments thereof, said disease or condition includes, but is not limited to, cholesterol disorders, lipidemias, cardiovascular disease, diabetes, obesity, baldness, skin diseases, cancer and multiple sclerosis, especially wherein said disease is a cardiovascular disease or a skin disease or said condition is baldness.

In an additional aspect, this invention teaches that hSCD1 has pharmacogenomic significance. Variants of hSCD1 including SNPs (single nucleotide polymorphisms), cSNPs (SNPs in a cDNA coding region), polymorphisms and the like may have dramatic consequences on a subject's response to administration of a prophylactic or therapeutic agent. Certain variants may be more or less responsive to certain agents. In another aspect, any or all therapeutic agents may have greater or lesser deleterious side-effects depending on the hSCD1 variant present in the subject.

In general, the invention discloses a process of selecting a prophylactic and/or therapeutic agent for administration to a subject in need thereof comprising,
 (a) determining at least a part of the hSCD1 nucleic acid sequence of said subject; and
 (b) comparing said hSCD1 nucleic sequence to known variants of hSCD1 nucleic acids;
 wherein said known variants are correlated with responsiveness to said agent and said agent is selected for said subject on the basis of a desired correlation. In this method the correlation may be a prophylactic and/or therapeutic effect or it may be avoidance of a deleterious side effect, or any other desired correlation.

In a pharmacogenomic application of this invention, an assay is provided for identifying cSNPs (coding region small nucleotide polymorphisms) in hSCD1 of an individual which are correlated with human disease processes or response to medication. The inventors have identified two putative cSNPs of hSCD1 to date:In exon 1, a C/A cSNP at nt 259, corresponding to a D/E amino acid change at position 8; and in exon 5, a C/A cSNP at nt 905, corresponding to a UM amino acid change at position 224. (Sequence numbering according to GenBank Accession: AF097514). It is anticipated that these putative cSNPs may be correlated with human disease processes or response to medication of individuals who contain those cSNPs versus a control population. Those skilled in the art are able to determine which disease processes and which responses to medication are so correlated.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

In applying the disclosure, it should be kept clearly in mind that other and different embodiments of the methods disclosed according to the present invention will no doubt suggest themselves to those of skill in the relevant art.

EXAMPLE 1

Disruption of Stearoyl-CoA Desaturase1 Gene in Mice Causes Decreased Plasma Triglycerides Levels, as Well as other Defects in Lipid Metabolism This example identifies, for the first time, specific SCD1 biological activities in mouse by characterizing an SCD1 gene specific knock-out mouse.

To investigate the physiological functions of SCD, we have generated SCD1 null (SCD1−/−) mice. The lipoprotein profile of SCD1 null (knock-out) mice demonstrates a striking decrease in triglyceride (i.e., VLDL) levels while maintaining approximately normal HDL and LDL levels. This result confirms that a mutation in SCD1 is a causative mutation of a low triglyceride (TG) lipoprotein profile in mice, and is distinct from other SCD isoforms in the mouse in this regard. Due to the severity of this phenotype it is clear that other SCD isoforms are unlikely to affect TG levels to such a great extent.

Targeted Disruption of the SCD1 Gene

Figure 1:
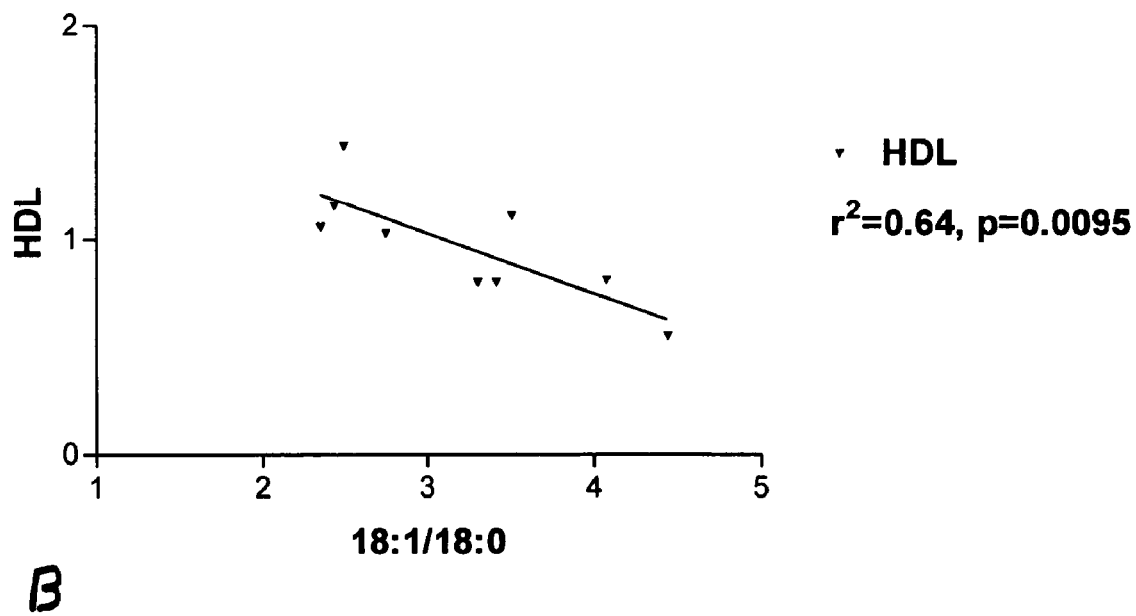
FIG. 1. Generation of SCD1 null mice (A) Targeting strategy for SCD1. A partial map of the genomic locus surrounding the Scd1 locus is shown. Homologous recombination resulted in the replacement of exons 1-6 by neo 7 gene. Gene-targeting events were verified by Southern blot analysis using EcoRI and probe A or B or by PCR analysis. (B) PCR analysis demonstrating SCD–/– mice. In breeding heterozygotes, wild-type, heterozygotes and homozygotes were born in Mendelian fashion (+/+:+/–:–/–=21:43:20 $x^2$=0.395). (C) Northern blot analysis. 20 μg of total RNA was isolated from the liver and subjected to Northern blot analyses. Blots were probed with a mouse SCD1 and 2 cDNA fragments. (D) Immunoblot analysis of liver showed the absence of immunoreactive SCD in SCD1–/– mice, whereas SCD1 protein was detected in liver tissue from both wild-type and heterozygote mice in a manner dependent on gene dosage. (E) Liver SCD activity was abolished in SCD–/– mice. As mentioned above, heterozygotes present an intermediate phenotype when compared to wild-type and null littermates. Enzyme activity is represented as nanomoles of substrate desaturated per milligram of protein per minute. Data are denoted as the mean ±SD (n=3).

FIG. 1A shows the strategy used to knock out the SCD1 gene. The mouse SCD1 gene includes 6 exons. The first 6 exons of the gene were replaced by a neomycin-resistant cassette by homologous recombination, resulting in the replacement of the complete coding region of the SCD1 gene (FIG. 1A). The vector was electroporated into embryonic stem cells and the clones that integrated the neo cassette were selected by growth on geneticin. Targeted ES clones were injected into C57Bl/6 blastocysts yielding four lines of chimeric mice that transmitted the disrupted allele through the germ-line. The mutant mice were viable and fertile and bred with predicted Mendelian distributions. A PCR based screen to assay successful gene targeting of the SCD1 locus is shown in FIG. 1B. To determine whether the expression of the SCD1 gene was ablated we performed Northern blot analysis (FIG. 1C) SCD1 mRNA is undetectable in liver of SCD1−/− mice and reduced by approximately 50% in SCD+/− mice. SCD2 mRNA was expressed at low levels in both SCD1−/− mice and wild-type mice. Consistent with Northern blot results, Western blot analysis showed no immunoreactive SCD protein in liver from SCD−/− mice, whereas SCD1 protein was detectable in both heterozygous and wild-type liver tissue in a manner dependent on gene dosage. SCD enzyme activity in liver, as measured by the rate of conversion of [1-$^{14}$C] stearoyl-CoA to [1-$^{14}$C]oleate (FIG. 1E) was high in the wild-type mice but was undetectable in the total extracts of livers of the SCD1−/− mice.

Lipid Analysis

Analysis of liver cholesterol ester (0.8±0.1 vs. 0.3±0.1 mg/g liver) and liver triglycerides (12.6±0.3 vs. 7.5±0.6 mg/g liver) showed that SCD1 KO animals have lower amounts of both cholesterol esters and triglycerides than wild-type controls. Plasma lipoprotein analysis showed a decrease in plasma triglycerides (120.6±6.8 vs. 45.4±3.8) in SCD−/− mice compared to normal controls. These findings are similar to findings in asebia mice. FIG. 2 records the plasma lipoprotein profile obtained using fast performance liquid chromatography. SCD1 Knock-Out mice showed a 65% reduction of triglyceride in VLDL fraction; but little or no significant difference in LDL or HDL levels.

Asebia mice are compared with the SCD1 Knock-Out mice in FIG. 2. The findings are remarkably similar. Asebia mice plasma lipoproteins were separated by fast performance liquid chromatography and the distribution of triglycerides among lipoproteins in the various density fractions of the mice (n=3) are shown. FIG. 3 shows an additional example of an Asebia mouse lipoprotein profile. These profiles showed a major difference in the distribution of triglycerides in the VLDL fraction of the SCD−/− and SCD−/+ mice. The levels of triglycerides in the SCD−/+ were 25 mg/dl in the VLDL, with very low levels in the LDL and HbL fractions. In contrast the SCD−/− had very low levels of triglycerides in the three lipoprotein fractions.

Fatty Acid Analysis

We also determined the levels of monounsaturated fatty acids in various tissues. Table 1 shows the fatty acid composition of several tissues in wild-type and SCD−/− mice. The relative amounts of palmitoleate (16:1n-7) in liver and plasma from SCD−/− mice decreased by 55% and 47% while those of oleate (18:1n-9) decreased by 35% and 32%, respectively. The relative amount of palmitoleate in white adipose tissue and skin of SCD−/− mice were decreased by more than 70%, whereas the reduction of oleate in these tissues was less than 20% although the reduction was significant statistically. These changes in levels of monounsaturated fatty acids resulted in reduction of desaturation indices indicating reduction in desaturase activity. In contrast to these tissues, the brain, which expresses predominantly the SCD2 isoform, had a similar fatty acid composition and unaltered desaturation index in both wild type and SCD−/− mice. We conclude that SCD1 plays a major role in the production of monounsaturated fatty acids in the liver.

TABLE I

Fatty acid composition of several tissues from SCD1 knockout mice

|  | 14:0 | 16:0 | 16:1n-7 | 18:0 | 18:1n-9 | 18:1n-7 | 18:2n-6 | 20:0 | 20:1n-9 | 20:1n-7 |
|---|---|---|---|---|---|---|---|---|---|---|
| Liver | | | | | | | | | | |
| +/+ | 0.8 | 25.9 | 1.1 | 16.1 | 16.2 | 1.6 | 16.3 | 0.0 | 0.0 | 0.0 |
| −/− | 1.0 | 27.2 | 0.5 | 22.8 | 10.6 | 1.0 | 13.9 | 0.0 | 0.0 | 0.0 |
| Eyelid | | | | | | | | | | |
| +/+ | 1.3 | 15.0 | 2.4 | 9.3 | 19.6 | 3.4 | 5.2 | 5.2 | 24.1 | 9.6 |
| −/− | 1.9 | 22.4 | 1.5 | 20.3 | 16.1 | 3.7 | 6.8 | 7.5 | 3.7 | 7.4 |
| WAT | | | | | | | | | | |
| +/+ | 3.3 | 27.6 | 5.2 | 5.7 | 35.1 | 1.9 | 19.5 | 0.0 | 0.0 | 0.0 |
| −/− | 2.7 | 29.2 | 1.5 | 14.8 | 29.1 | 1.7 | 18.7 | 0.0 | 0.0 | 0.0 |
| Skin | | | | | | | | | | |
| +/+ | 3.5 | 29.3 | 4.0 | 9.7 | 32.4 | 2.1 | 15.0 | 0.0 | 0.0 | 0.0 |
| −/− | 3.1 | 30.7 | 1.4 | 14.2 | 28.1 | 1.8 | 17.6 | 0.0 | 0.0 | 0.0 |
| Brain | | | | | | | | | | |
| +/+ | 1.1 | 25.7 | 0.8 | 21.6 | 16.5 | 3.1 | 1.1 | 0.0 | 0.0 | 0.0 |
| −/− | 1.1 | 26.2 | 0.8 | 21.1 | 15.8 | 3.3 | 1.2 | 0.0 | 0.0 | 0.0 |
| Eye Ball | | | | | | | | | | |
| +/+ | 2.9 | 31.3 | 1.6 | 28.5 | 19.1 | 2.6 | 0.0 | 0.0 | 0.0 | 0.0 |
| −/− | 3.2 | 32.3 | 1.5 | 29.8 | 18.8 | 2.4 | 0.0 | 0.0 | 0.0 | 0.0 |

|  | 20:4n-6 | 22:6n-3 | 16:1/16:0 | 18:1n-9/18:0 | 18:1n-7/18:0 | 20:1n-9/20:0 | 20:1n-7/20:0 |
|---|---|---|---|---|---|---|---|
| Liver | | | | | | | |
| +/+ | 9.2 | 7.8 | 0.041 | 1.006 | 0.100 | 0.000 | 0.000 |
| −/− | 6.8 | 8.8 | 0.018 | 0.465 | 0.044 | 0.000 | 0.000 |
| Eyelid | | | | | | | |
| +/+ | 0.9 | 0.8 | 0.160 | 2.108 | 0.366 | 4.635 | 1.846 |
| −/− | 1.7 | 1.5 | 0.067 | 0.793 | 0.182 | 0.493 | 0.987 |
| WAT | | | | | | | |
| +/+ | 0.3 | 0.2 | 0.190 | 6.211 | 0.340 | 0.000 | 0.000 |
| −/− | 0.4 | 0.8 | 0.050 | 1.967 | 0.115 | 0.000 | 0.000 |
| Skin | | | | | | | |
| +/+ | 0.9 | 0.7 | 0.136 | 3.351 | 0.219 | 0.000 | 0.000 |
| −/− | 0.9 | 0.8 | 0.045 | 1.982 | 0.128 | 0.000 | 0.000 |
| Brain | | | | | | | |
| +/+ | 9.4 | 12.4 | 0.032 | 0.764 | 0.145 | 0.000 | 0.000 |
| −/− | 9.5 | 13.1 | 0.030 | 0.752 | 0.154 | 0.000 | 0.000 |

TABLE I-continued

Fatty acid composition of several tissues from SCD1 knockout mice

Eye Ball

| | | | | | | | |
|---|---|---|---|---|---|---|---|
| +/+ | 2.9 | 7.2 | 0.051 | 0.671 | 0.091 | 0.000 | 0.000 |
| -/- | 2.3 | 5.8 | 0.046 | 0.632 | 0.081 | 0.000 | 0.000 |

Tissue total lipids from each mouse were extracted.
The lipids were methyl esterified and quantified by GLC as described under Experimental Procedures.
Standard errors for all values were less than 25% of the mean and were omitted from table for clarity.
Bold values represent a statistical significance of p < 0.05 between wild-type and SCD -/- mice (student's t test).
The values of monounsaturated/saturated fatty acids were calculated from the mean value.

Figure 4:
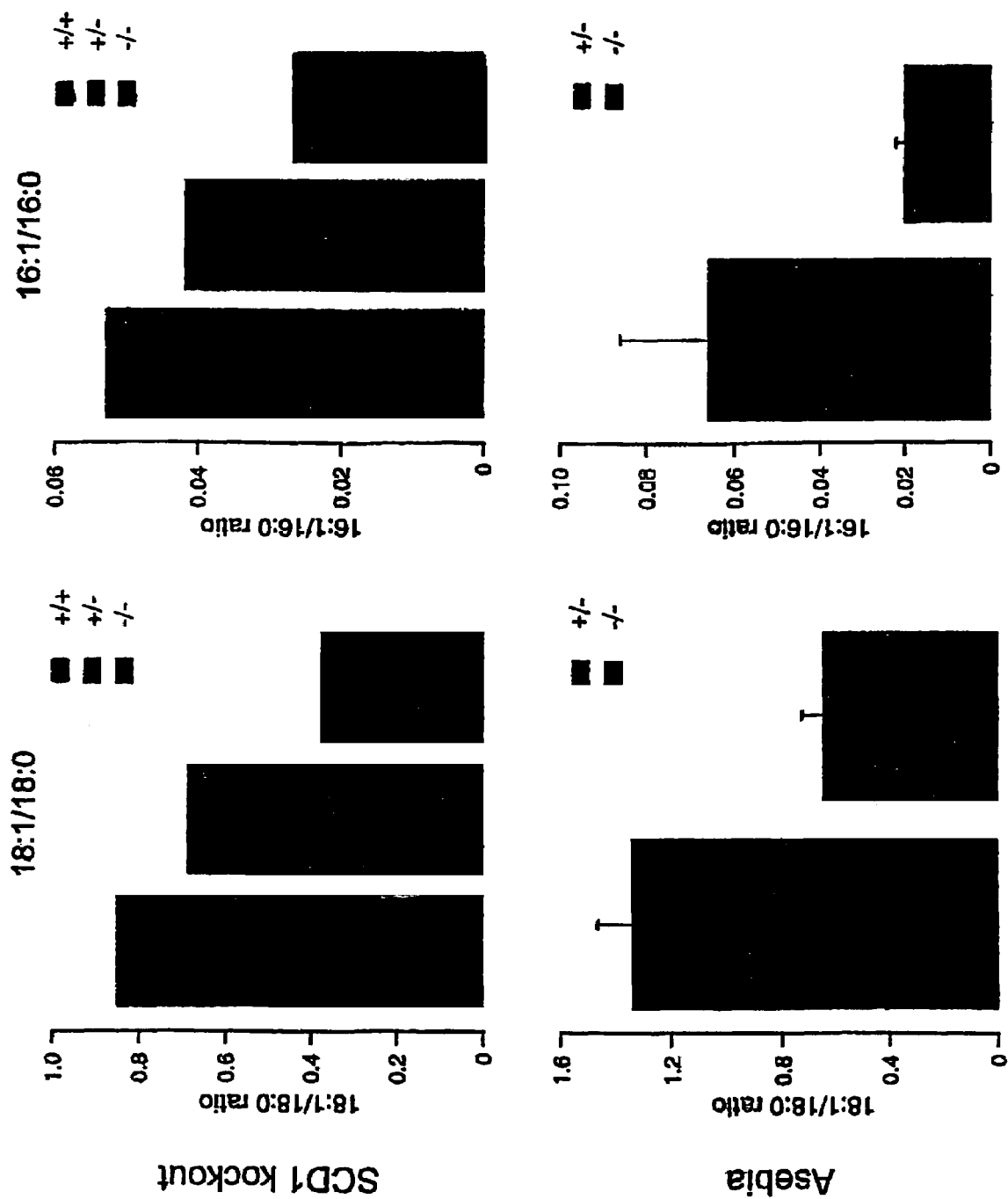
FIG. 4. Ratio of monounsaturated to saturated fatty acid in mouse plasma (the desaturation index) decreases in a manner directly proportional to the level of SCD activity I. Comparison of SCD1 knock-out and asebia mice to their respective controls.

FIG. 4 (quantified in Table 2) demonstrate that SCD1 is a major contributor to the plasma desaturation indices (ratio of plasma 18:1/18:0 or 16:1/16:0 in the total lipid fraction), as judged by plasma fatty acid analysis of both the SCD1 KO and asebia mice. In both animal models, a reduction of approximately 50% or greater is observed in the plasma desaturation indices. This demonstrates that the plasma desaturation index is highly dependent on the function of SCD1

TABLE 2

Fatty acid desaturation indices in asebia mutants and heterozygotes

| Sex/genotype | 18:1/18:0 | 16:1/16:0 |
|---|---|---|
| Male +/- | 1.393 | 0.044 |
| Male -/- | 0.732 | 0.018 |
| Female +/- | 1.434 | 0.074 |
| Female -/- | 0.642 | 0.021 |
| Female +/- | 1.203 | 0.081 |
| Female -/- | 0.574 | 0.022 |

Experimental Procedures for Knockout Mice:

Generation of the SCDI Knockout Mice.

Mouse genomic DNA for the targeting vector was cloned from 129/SV genomic library. The targeting vector construct was generated by insertion of a 1.8-kb Xba I/Sac I fragment with 3' homology as a short arm and 4.4-kb Cla I/Hind III fragment with 5' homology cloned adjacent to neo expression cassette. The construct also contains a HSV thymidine kinase cassette 3' to the 1.8-kb homology arm, allowing positive/negative selection. The targeting vector was linearized by Not I and electroporated into embryonic stem cells. Selection with geneticin and gancyclovior was performed. The clones resistant to both geneticin and gancyclovior were analyzed by Southern blot after EcoRI restriction enzyme digestion and hybridized with a 0.4-kb probe located downstream of the vector sequences. For PCR genotyping, genomic DNA was amplified with primer A

5'-GGGTGAGCATGGTGCTCAGTCCCT-3'    (SEQ ID NO: 2)

which is located in exon 6, primer B

5'-ATAGCAGGCATGCTGGGGAT-3'    (SEQ ID NO: 3)

which is located in the neo gene (425 bp product, targeted allele), and primer C

5'-CACACCATATCTGTCCCCGACAAATGTC-3'    (SEQ ID NO: 4)

which is located in downstream of the targeting gene (600 bp product, wild-type allele). PCR conditions were 35 cycles, each of 45 sec at 94° C., 30 sec at 62° C., and 1 min at 72° C. The targeted cells were microinjected into C57BI/6 blastocysts, and chimeric mice were crossed with C57BLU6 or 129/SvEv Taconic females, and they gave the germ-line transmission. Mice were maintained on a 12-h dark/light cycle and were fed a normal chow diet, a semi-purified diet or a diet containing 50% (% of total fatty acids) triolein, tripalmitolein or trieicosenoin. The semi-purified diet was purchased from Harlan Teklad (Madison, Wis.) and contained: 20% vitamin free casein, 5% soybean oil, 0.3% L-cystine, 13.2% Maltodextrin, 51.7% sucrose, 5% cellulose, 3.5% mineral mix (AIN-93G-MX), 1.0% vitamin mix (AIN-93-VX), 0.3% choline bitartrate. The fatty acid composition of the experimental diets was determined by gas liquid chromatography. The control diet contained 11% palmitic acid (16: 0), 23% oleic acid (18:1n-9), 53% linoleic acid (18:2n-6) and 8% linolenic acid (18:3n-3). The high triolein diet contained 7% 16:0, 50% 18:1n-9, 35% 18:2n-6 and 5% 18:3n-3.

Materials

Radioactive [-$^{32}$P]dCTP (3000 Ci/mmol) was obtained from Dupont Corp. (Wilmington, Del.). Thin layer chromatography plates (TLC Silica Gel G60) were from Merck (Darmstadt, Germany). [1-$^{14}$C]-stearoyl-CoA was purchased from American Radiolabeled Chemicals, Inc. (St. Louis, Mo.). Immobilon-P transfer membranes were from Millipore (Danvers, Mass.). ECL Western blot detection kit was from Amersham-Pharmacia Biotech, Inc. (Piscataway, N.J.). All other chemicals were purchased from Sigma (St. Louis, Mo.).

Lipid Analysis

Total lipids were extracted from liver and plasma according to the method of Bligh and Dyer (Bligh and Dyer, 1959), and phospholipids, wax esters, free cholesterol, triglycerides and cholesterol esters were separated by silica gel high performance TLC. Petroleum hexane/diethyl ether/acetic acid (80: 30:1) or benzene/hexane (65:35) was used as a developing solvent (Nicolaides and Santos, 1985). Spots were visualized by 0.2% 2',7'-dichlorofluorecein in 95% ethanol or by 10% cupric sulfate in 8% phosphoric acid. The wax triester, cholesterol ester and triglyceride spots were scraped, 1 ml of 5% HCl-methanol added and heated at 100° C. for 1 h (Miyazaki et al., 2000). The methyl esters were analyzed by gas-liquid chromatography using cholesterol heptadecanoate, triheptadecanoate and heptadecanoic acid as internal standard. Free cholesterol, cholesterol ester and triglycerides contents of eyelid and plasma were determined by enzymatic assays (Sigma St. Louis, Mo. and Wako Chemicals, Japan).

Isolation and Analysis of RNA

Total RNA was isolated from livers using the acid guanidinium-phenol-chloroform extraction method (Bemlohr et al., 1985). Twenty micrograms of total RNA was separated by 1.0% agarose/2.2 M formaldehyde gel electrophoresis and transferred onto nylon membrane. The membrane was hybridized with 32P-labeled SCD1 and SCD2 probes. pAL15 probe was used as control for equal loading (Miyazaki, M., Kim, Y. C., Gray-Keller, M. P., Attie, A. D., and Ntambi, J. M. (2000). The biosynthesis of hepatic cholesterol esters and triglycerides is impaired in mice with a disruption of the gene for stearoyl-CoA desaturase 1. J Biol Chem 275, 30132-8).

SCD Activity Assay

Stearoyl-CoA desaturase activity was measured in liver microsomes essentially as described by Shimomura et al. (Shimomura, I., Shimano, H., Kom, B. S., Bashmakov, Y., and Horton, J. D. (1998). Nuclear sterol regulatory element-binding proteins activate genes responsible for the entire program of unsaturated fatty acid biosynthesis in transgenic mouse liver. J Biol Chem 273, 35299-306. ). Tissues were homogenized in 10 vol. of buffer A (0.1M potassium buffer, pH 7.4). The microsomal membrane fractions (100,000×g pellet) were isolated by sequential centrifugation. Reactions were performed at 37° C. for 5 min with 100 µg of protein homogenate and 60 µM of [1-$^{14}$C]-stearoyl-CoA (60,000 dpm), 2 mM of NADH, 0.1M of Tris/HCl buffer (pH 7.2). After the reaction, fatty acids were extracted and then methylated with 10% acetic chloride/methanol. Saturated fatty acid and monounsaturated fatty acid methyl esters were separated by 10 % AgNO$_3$-impregnated TLC using hexane/diethyl ether (9:1) as developing solution. The plates were sprayed with 0.2 % 2',7'-dichlorofluorescein in 95% ethanol and the lipids were identified under UV light. The fractions were scraped off the plate, and the radioactivity was measured using a liquid scintillation counter. The enzyme activity was expressed as nmole min$^{-1}$ mg$^{-1}$ protein.

Immunoblotting

Pooled liver membranes from 3 mice of each group were prepared as described by Heinemann et al (Heinemann and Ozols, 1998). The same amount of protein (25 µg) from each fraction was subjected to 10% SDS-polyacrylamide gel electrophoresis and transferred to Immobilon-P transfer membranes at 4° C. After blocking with 10% non-fat milk in TBS buffer (pH 8.0) plus Tween at 4° C. overnight, the membrane was washed and incubated with rabbit anti-rat SCD as primary antibody and goat anti-rabbit IgG-HRP conjugate as the secondary antibody. Visualization of the SCD protein was performed with ECL western blot detection kit.

Histology

Tissues were fixed with neutral-buffered formalin, embedded in paraffin, sectioned and stained with hematoxylin and eosin.

This work was supported by a grant-in-aid from the American Heart Association-Wisconsin affiliate and in part by grant #DAMD17-99-9451 from DOD.

Experimental Procedures for Asebia Mice:

Animals and Diets-Asebia homozygous (ab J/ab J or −/−) and heterozygous (+/ab J or +/−) mice were obtained from the Jackson Laboratory (Bar Harbor, Me.) and bred at the University of Wisconsin Animal Care Facility. In this study, comparisons are made between the homozygous (−/−) and the heterozygous (+/−) mice since the latter are indistinguishable from normal mice. Mice were housed in a pathogen-free barrier facility operating a 12-h light/12-h dark cycle. At 3 weeks of age, these mice were fed ad libitum for 2 wks or 2 months, on laboratory chow diet or on a semi-purified diet containing 50% (% of total fatty acids) triolein or tripalmitolein. The semi-purified diet was purchased from Harlan Teklad (Madison, Wis.) and contained: 18% vitamin free casein, 5% soybean oil, 33.55% corn starch, 33.55% sucrose, 5% cellulose, 0.3%-L methionine, 0.1% choline chloride, salt mix (AIN-76A) and vitamin mix (AIN-76A). The fatty acid composition of the experimental diets was determined by gas liquid chromatography. The control diet contained 11% palmitic acid (16:0), 23% oleic acid (18:1n-9), 53% linoleic acid (18:2n-6) and 8% linoleic acid (18:3n-3). The high triolein diet contained 7% 16:0, 50% 18:1n-9, 35% 18:2n-6 and 5% 18:3n-3. The high trpalmitolein diet contained 6% 16:0, 49% palmitoleic acid (16:1n-7), 12% 18:1n-9, 27% 18:2n-6 and 4% 18:3n-3.

Animals were anesthetized at about 10:00 a.m. by intraperitoneal injection of pentobarbital sodium (0.08 mg/g of body weight) Nembutal, Abbot, North Chicago, Ill.). Liver was isolated immediately, weighed, and kept in liquid nitrogen. Blood samples were obtained from the abdominal vein.

Materials-Radioactive α-$^{32}$P]dCTP (3000 Ci/mmol) was obtained from Dupont Corp. (Wilmington, Del.). Thin layer chromatography plates (TLC Silica Gel G60) were from Merck (Darmstadt, Germany). [1-$^{14}$C]-stearoyl-CoA, [$^3$H] cholesterol and [1-$^{14}$C]oleoyl-CoA were purchased from American Radiolabeled Chemicals, Inc. (St. Louis, Mo.). Immobilon-P transfer membranes were from Millipore (Danvers, Mass.). ECL Western blot detection kit was from Amersham-Pharmacia Biotech, Inc. (Piscataway, N.J.). LT-1 transfection reagent was from PanVera (Madison, Wis.). All other chemicals were purchased from Sigma (St. Louis, Mo.). The antibody for rat liver microsome SCD was provided by Dr. Juris Ozols at University of Connecticut Health Center. pcDNA3-1 expression vector SCD1 was provided by Dr. Trabis Knight at Iowa state university.

Lipid Analysis-Total lipids were extracted from liver and plasma according to the method of Bligh and Dyer (Bligh, E. G., and Dyer, W. J. (1959) Can J Biochem Physiol 37, 911-917. ), and phospholipids, free cholesterol, triglycerides and cholesterol esters were separated by silica gel TLC. Petroleum ether/diethyl ether/acetic acid (80:30:1) was used as a developing solvent. Spots were visualized by 0.2% 2',7'-dichlorofluorecein in 95% ethanol or by 10% cupric sulfate in 8% phosphoric acid. The phospholipid, cholesterol ester and triglyceride spots were scraped, 1 ml of 5% HCl-methanol added and heated at 100° C. for 1 h. The methyl esters were analyzed by gas-liquid chromatography using cholesterol heptadecanoate as internal standard (Lee, K. N., Pariza, M. W., and Ntambi, J. M. (1998) Biochem. Biophys. Res. Commun. 248, 817-821; Miyazaki, M., Huang, M. Z., Takemura, N., Watanabe, S., and Okuyama, H. (1998) Lipids 33, 655-61). Free cholesterol, cholesterol ester and triglycerides contents of liver and plasma were determined by enzymatic assays (Sigma St. Louis, Mo. and Wako Chemicals, Japan).

Plasma Lipoprotein Analysis-Mice were fasted a minimum of 4 hours and sacrificed by CO 2 asphyxiation and/or cervical dislocation. Blood was collected aseptically by direct cardiac puncture and centrifuged (13,000×g, 5 min, 4° C.) to collect plasma. Lipoproteins were fractionated on a Superose 6HR 10/30 FPLC column (Pharmacia). Plasma samples were diluted 1:1 with PBS, filtered (Cameo 3AS syringe filter, 0.22 µm) and injected onto the column that had been equilibrated with PBS containing 1 mM EDTA and 0.02% NaN 3. The equivalent of 100 µl of plasma was injected onto the column. The flow rate was set constant at 0.3 ml/min. 500 µl fractions were collected and used for total triglyceride measurements (Sigma). Values reported are for total triglyceride mass per fraction. The identities of the lipoproteins have been confirmed by utilizing anti-ApoB immunoreactivity for LDL and Anti-Apo A1 immnunoreactivity for HDL (not shown).

EXAMPLE 2

Demonstration of Significant Correlation Between the 18:1/18:0 FFA Ratio and TG/HDL Levels in Humans This example demonstrates, for the first time, that delta-9 desaturase activity in humans correlates directly with serum levels of triglyceride (VLDL) and inversely with serum HDL level and total serum cholesterol.

Experimental Design:

Plasma from a total of 97 individuals was analyzed for fatty acid content by gas chromatography (GC). Total free fatty acid (FFA) content was measured and the ratios of oleate to stearate (18:1/18:0) and palmitoleate to palmitate (16:1/16:0) were computed, defined as the desaturation indices, as above. We sought to find a relationship between these ratios and three clinical indicators; plasma TG (triglyceride) levels, plasma HDL (high density lipoprotein) levels, and total plasma cholesterol.

Patient Sample:

The patient sample was chosen to maximize phenotypic diversity in terms of HDL. Within our cohort, 21 individuals displayed a high HDL phenotype (>$90^{th}$ percentile for age and sex), 12 individuals displayed a low HDL phenotype of unknown etiology (<$5^{th}$ percentile for age and sex), while six displayed a low HDL phenotype due to mutations in the ABCA1 gene. 33 individuals fall within normal HDL parameters (<$90^{th}$ and >$5^{th}$ percentile for age and sex).

We also attempted to diversity our sample in terms of TG levels, by including 9 individuals with Familial Combined Hyperlipidemia (FCHL) who have high TG and/or cholesterol as well as 16 additional control individuals with normal TG levels.

In some cases, multiple individuals from the same family were tested. Five of the six individuals with an ABCA1 mutation are part of the same family (NL-020). Multiple individuals were also tested from other pedigrees segregating a low HDL phenotype that is not genetically linked to ABCA1. In this category, two affected individuals were tested from NL-008, while four affected individuals were tested from NL-001. The remaining six individuals with a low HDL phenotype are not related to one another, and were chosen from distinct pedigrees. Of those individuals with high HDL, seven of them were unrelated to one another. It is not yet clear if the high HDL observed in these individuals has a clear genetic basis in family members. The remaining 14 individuals with a high HDL phenotype, six of them are from family HA-1 and eight are from a distinct family, HA-3. Unaffected individuals related to those with both low and high HDL were also tested.

Our cohort show wide variation in TG and HDL levels. In general, individuals with low HDL have high TG levels and those with high TG levels tend to have low HDL levels. This relationship between TG and HDL has been previously noted in the literature (Davis et al., 1980).

Analysis of fatty acid esters was determined as follows. Cells from patient samples were washed twice with cold phosphate-buffered saline and total cellular lipids were extracted three times with CHCl3/MeOH (2:1 v/v). The three lipid extractions were combined in a screw-capped glass tube, dried under N2 gas at 40° C. in a heat block, and resuspended in toluene. Fatty acid methyl esters were produced from BCl3/MeOH (Alltech, Deerfield Ill.), extracted with hexane, dried, and resuspended in hexane. Fatty acid methyl esters were identified using a Hewlett-Packard 6890 gas chromatograph equipped with a 7683 auto injector and an HP-5 column (30 m' 0.25 mm, 0.25 µm film thickness) connected to a flame ionization detector set at 275° C. The injector was maintained at 250° C. The column temperature was held at 180° C. for 2 min following injection, increased to 200° C. at 8° C./min, held at 200° C. for 15 min, and then increased to 250° C. at 8° C./min. Under these conditions, the ?9?16:1?, 16:0?, ?9?18:1- and 18:0-methyl esters eluted at 9.2 min, 9.7 min, 15.3 min, and 16.4 min, respectively. See Lee et al. (1998). Biochem. Biophys. Res. Commun. 248:817-821; Miyazaki et al. (1998) Lipids 33:655-661; and Miyazaki M, Kim Y C, Gray-Keller M P, Attie A D, Ntambi J M. 2000. J Biol Chem. 275(39): 30132-8.

Results

Linear regression analysis was carried out using the entire human data set. The ratio of 18:1/18:0 showed a significant relationship to TG levels ($r^2$=0.39, p<0.0001) (FIG. 5a), as well as significant correlations to HDL levels ($r^2$=0.12, p=0.0006) (FIG. 5b).

Figure 6:
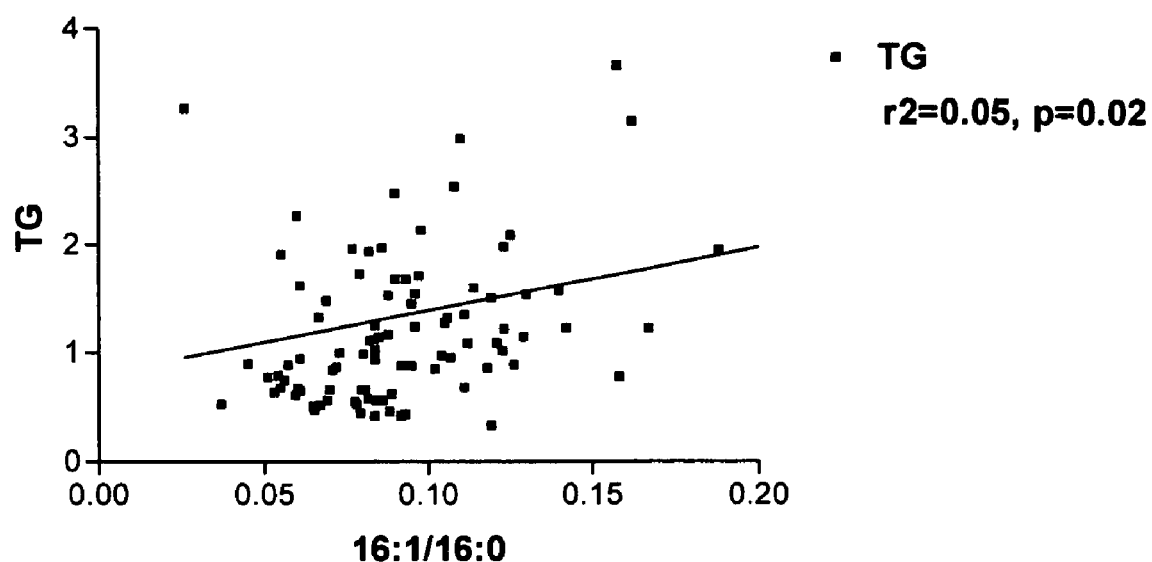
FIG. 6 shows a linear regression analysis indicating a weak relationship between the relative level of 16:1/16:0 to plasma TG levels was observed ($r^2=0.05$, $p=0.03$). Experimental details are in Example 2.

The 16:1/16:0 plasma fatty acid ratio was measured in a similar manner, although the results were not as striking. A weak relationship between the relative level of 16:1/16:0 to plasma TG levels was observed ($r^2$=0.05, p=0.03) (FIG. 6), whereas the relationship between the 16:1/16:0 ratio and HDL levels did not reach significance (not shown). In contrast to the 18:1/18:0 ratio, the 16:1/16:0 ratio did explain a portion of the variance in total cholesterol levels ($r^2$=0.06, p=0.02) (not shown).

Overall the 18:1/18:0 ratio accounted for 18% of the variance in total plasma fatty acid content (p=0.005) while the 16:1/16:0 ratio accounted for 8% of the variation in this value (p=0.02), when the individuals with FCHL and their associated controls were excluded from the analysis (not shown in the Figure).

Finally, for the portion of our sample for which Body Mass Index (BMI) values were available, we measured a positive correlation between 18:1/18:0 ratios and BMI ($r^2$=0.13, p=0.00) (data not shown).

The sample was stratified based on HDL levels to determine if the relationship between SCD activity (as measured by the 18:1/18:0 ratio) and TG levels was independent of the primary cause of the observed dyslipidemia.

A positive correlation was observed between 18:1/18:0 and TG in persons with high HDL.

Figure 7:
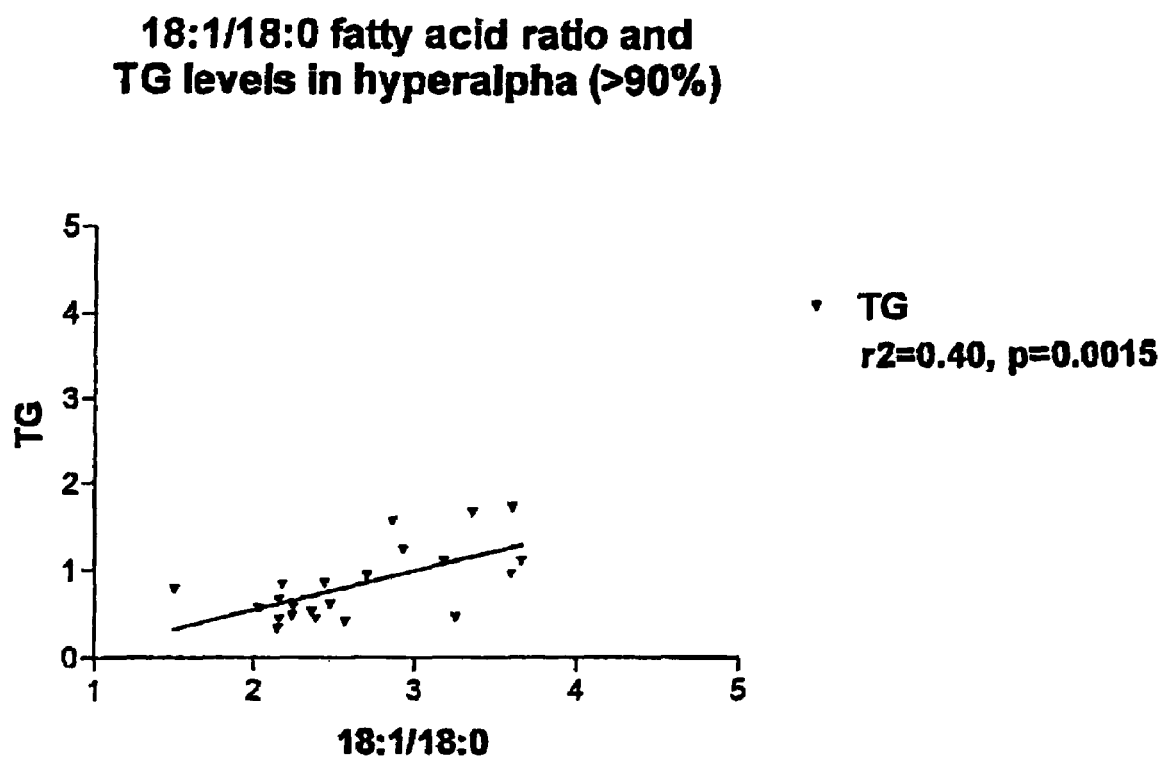
FIG. 7 shows a linear regression analysis of those individuals with a high HDL phenotype (>90$^{th}$ percentile). These individuals demonstrated a significant relationship between the 18:1/18:0 ratio and TG levels ($r^2=0.40$, $p<0.005$).

Analysis of those individuals with a high HDL phenotype (>$90^{th}$ percentile) demonstrated a significant relationship between the 18:1/18:0 ratio and TG levels ($r^2$=0.40, p<0.005) (FIG. 7). The relationship between 18:1/18:0 ratio and HDL levels in this group did not reach significance (data not shown). The 16:1/16:0 ratio did not account for a significant proportion of the variance in total cholesterol, TG or HDL levels in this subset of our cohort.

In order to determine if a stronger relationship between the 18:1/18:0 index and TG levels would be apparent in a genetically homogenous background, the HA-1 and HA-3 families were analyzed separately. Both affected and unaffected family members were included in the analysis. In both families, a similar relationship between 18:1/18:0 and TG levels was observed (HA-1: $r^2$=0.36, p=0.005 (FIG. 8a), HA-3: $r^2$=0.32, p=0.009 (not shown in the figure)). The strength of these relationships was similar to that observed in the entire cohort. 18:1/18:0 ratios also correlated with HDL levels in HA-1, although this relationship did not reach significance in HA-3 (HA-1: $r^2$=0.32, p=0.009 (FIG. 8b), HA-3: $r^2$=0.10, p=0.22 (not shown)).

Figure 9:
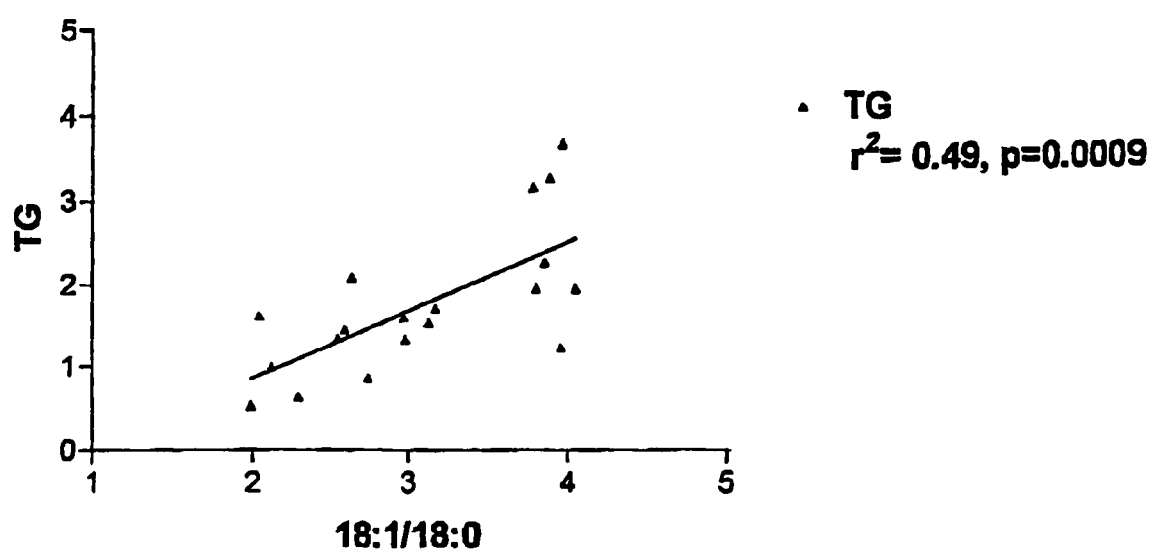
FIG. 9 shows the relationship observed between the 18:1/18:0 ratio and TG levels ($r^2=0.49$, $p=0.0009$) when only persons with low HDL (<5$^{th}$ percentile) are considered.

A positive correlation was also observed between 18:1/18:0 and TG in those with low HDL. When all individuals with low HDL (<5$^{th}$ percentile) were analyzed as a group, a significant relationship was observed between the 18:1/18:0 ratio and TG levels ($r^2$=0.49, p=0.0009) (FIG. 9). As observed in our analysis of the high HDL patient subset, the relationship between the 18:1/18:0 ratio and HDL did not meet significance in the low HDL group (data not shown). In addition, no significant result was noted when the 16:1/16:0 ratio was regressed with HDL, TG and total cholesterol values.

Analysis of family NL-001, which segregated a low HDL phenotype of unknown genetic etiology, and family NL-0020, which segregated an ABCA1 mutation, tended towards the relationships noted above between fatty acid ratios and lipid parameters when affected individuals in each family were considered. However, these results did not reach statistical significance due to the small number of individuals analyzed in each case (NL-001: FIG. 10a, b and NL0020: FIG. 11a, b). A general trend towards higher 18:1/18:0 ratios in older Tangiers patients was noted. This could be an effect independent of the disease, although an age dependent effect on the 18:1/18:0 ratio was noted in neither of the HA-1 and HA-3 families nor in the entire cohort (not shown in FIG. 11).

Figure 12:
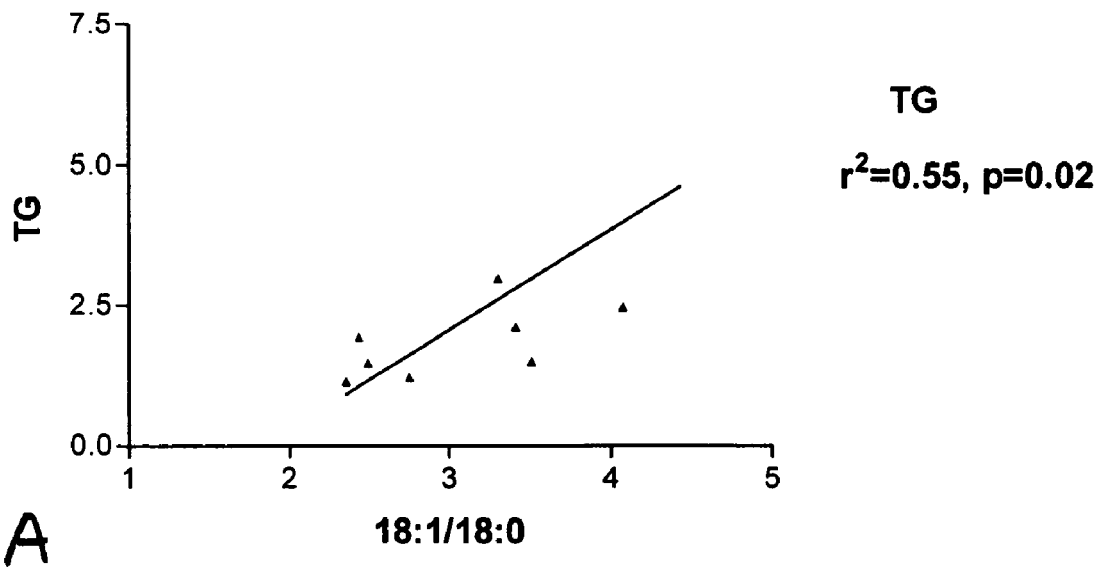
FIG. 12 is a plasma fatty acid analysis showing the relationship between the 18:1/18:0 ratio and TG levels ($r^2=0.56$, $p=0.02$) (Panel A), HDL levels (r2=0.64, $p=0.0095$) (Panel B) and total cholesterol levels (r2=0.50, $p=0.03$) in nine persons with Familial Combined Hyperlipidemia (FCHL) (Panel C).
Figures 2, 12:
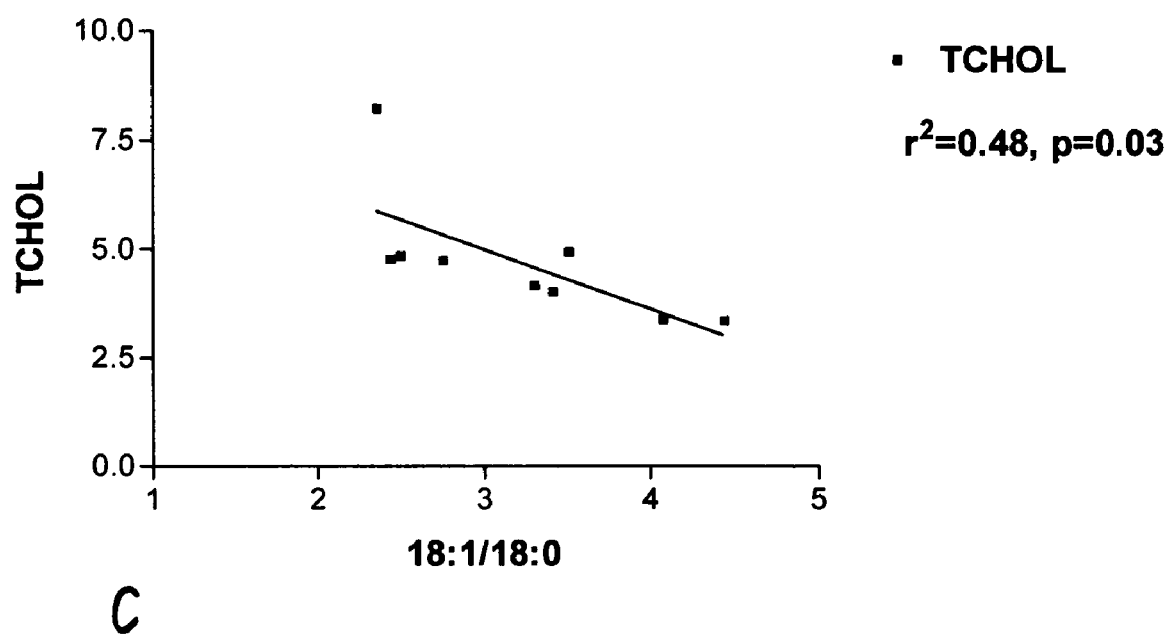
FIG. 2. Plasma lipoprotein profiles in SCD1 Knock-out and Asebia Male Mice. The top two panels depict the triglyceride content of the lipoprotein fractions, the bottom two panels depict the cholesterol content of the lipoprotein fractions.

FIG. 12 shows the relationship between the 18:1/18:0 ratio and TG levels (r2=0.56, p=0.03) (FIG. 12a), HDL levels (r2=0.64, p=0.009) (FIG. 12b) and total cholesterol levels (r2=0.50, p=0.03) in persons with Familial Combined Hyperlipidemia (FCHL) (FIG. 12c).

Our analysis is the first demonstration in humans that SCD function, as measured by the 16:1/16:0 and 18:1/18:0 desaturation indices, correlates positively with plasma TG levels and inversely with plasma HDL. Importantly, we observe this correlation irrespective of the underlying cause of hyper- or hypo-triglyceridemia, suggesting that the relationship between SCD activity and TG levels is a generalized effect. Therefore, inhibition of SCD activity in humans is linked to decreased serum TG (or VLDL) levels, increased total cholesterol levels, increased HDL levels, and decreased body-mass-index (BMI), independent of the primary cause of TG elevation. Importantly, SCD1 inhibitors could be used as a combination therapy in patients also being treated for FCHL.

In summary, when taken together, Examples 1 and 2 establish for the first time a positive correlation between SCD1 activity and TG levels in mammals, as well as an inverse correlation between SCD1 activity and HDL in humans. Our analysis of the asebia and SCD1 KO are definitive in their implication of SCD1 as the major contributor to the desaturation index. We have used this index as a surrogate for SCD1 activity in our human studies. Thus, inhibitors of SCD1 function in mammals, including humans, are likely to both lower TG and raise HDL.

EXAMPLE 3

Plasma Fatty Acid Analysis in a Mouse Model of Dyslipidemia

In order to confirm the above described relationship observed in humans between the 18:1/18:0 desaturation index and TG levels. We also performed plasma fatty acid analysis in a mouse model of the human disease FCHL. In the mouse hyperlipidemic strain ("hyplip") TG levels are elevated as compared to wild-type.

The hyperlipidemic mouse HcB-19 showed an elevated 18:1/18:0 desaturation index. This mouse model of familial combined hyperlipidemia (HcB-19) displays elevated levels of TG, cholesterol, as well as increased secretion of VLDL and apoB (Castellani et al, Mapping a gene for combined hyperlipidaemia in a mutant mouse strain. Nat Genet; 18(4): 374-7 (1998).

Figure 13:
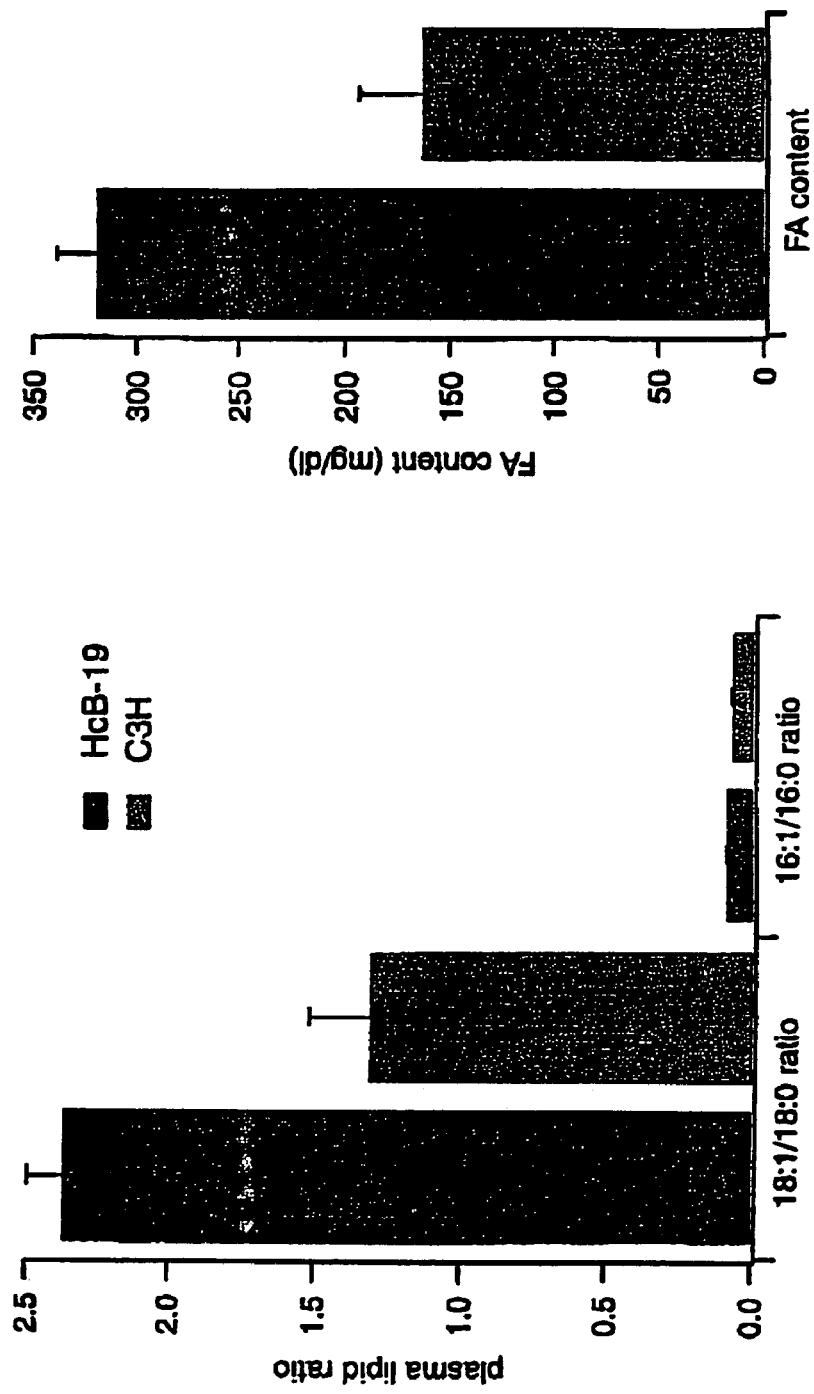
FIG. 13 is a plasma fatty acid analysis showing a significantly elevated 18:1/18:0 ratio in hyperlipidemic mice (HcB-19) when compared to unaffected controls of the parental strain (C3H).

Plasma fatty acid analysis demonstrated that these animals have a significantly elevated 18:1/18:0 ratio when compared to unaffected controls of the parental strain (FIG. 13). The HcB-19 animals did not, however, show a significant elevation of the 16:1/16:0 index when compared to controls. Therefore, we observe a positive correlation between the 18:1/18:0 desaturation index and TG levels in this animal model of FCHL.

EXAMPLE 4

Transcriptional Regulators of SCD1 and Their Use as Drug Screening Targets

This example reports, for the first time, the complete genomic promoter sequence of human SCD1. This promoter is used herein to identify regulatory elements that modulate and control SCD1 expression in humans, and identifies regulatory proteins that are suitable targets for small molecule intervention to modulate expression of SCD1 in humans.

The human SCD1 promoter sequence is set forth at SEQ ID No. 1. This sequence has not been accurately annotated in Genbank and has been reported as 5'UTR in a number of records.

FIG. 14 illustrates the location of regulatory sequences and binding sites in the homologous region of the mouse SCD1 and human SCD1 promoter and 5'-flanking regions. The top scale denotes the position relative to the transcriptional start site. Important promoter sequence elements are indicated.

The human SCD1 promoter structure is similar to that of the mouse SCD1 isoform and contains conserved regulatory sequences for the binding of several transcription factors, including the sterol regulatory element binding protein (SREBP), CCMT enhancer binding protein-alpha (C/EBPa) and nuclear factor-1 (NF-1) that have been shown to transactivate the transcription of the mouse SCD gene. Cholesterol and polyunsaturated fatty acids (PUFAs) decreased the SCD promoter-luciferase activity when transiently transfected into HepG2 cells. The decrease in promoter activity in the reporter construct correlated with decreases in endogenous SCD mRNA and protein levels. Transient co-transfection into HepG2 cells of the human SCD promoter-luciferase gene construct together with expression vector for SREBP revealed that SREBP trans-activates the human SCD promoter. Our studies indicate that like the mouse SCD1 gene, the human SCD gene is regulated by polyunsaturated fatty acids and cholesterol at the level of gene transcription and that SREBP plays a role in the transcriptional activation of this gene.

Construction of the Chimeric Promoter Luciferase Plasmid

A human placenta genomic library in bacteria-phage I EMBL3 was screened with a 2.0 kb PstI insert of the mouse pC3 cDNA (Ntambi, J. M., Buhrow, S. A., Kaestner, K. H., Christy, R. J., Sibley, E., Kelly, T. J. Jr., and M. D. Lane. 1988. Differentiation-induced gene expression in 3T3-L1 preadipocytes: Characterization of a differentially expressed gene encoding stearoyl-CoA desaturase. J. Biol. Chem. 263: 17291-17300. ) as a radioactive probe and seven plaques were isolated. Two of these plaques were purified to homogeneity, the DNA isolated and designated HSCD1and HSCD3. A DNA primer based on the sequence corresponding to the first exon of the cDNA of the published human stearoyl-CoA desaturase gene (Zhang, L., G. E. Lan, S. Parimoo, K. Stenn and S. M. Proutey. 1999. Human stearoyl-CoA desaturase alternative transcripts generated from a single gene by usage of tandem polyadenylation sites. Biochem. J. 340: 255-264) was synthesized and used to sequence the two phage clones by the dideoxy nucleotide chain termination method. A preliminary sequence was generated and primers upstream 5'NNNNGGTACCTTNNGAAAAGAACAGCGCCC 3'  SEQ ID No. 5 and downstream:

5'NNNNAGATCTGTGCGTGGAGGTCCCCG 3'  SEQ ID No. 6 were designed to amplify approximately 540 bases of the promoter region upstream of the transcription start site: These primers contain inserted restriction enzyme sites (underlined), Kpn1 for upstream, and BgIII for downstream, with a 4 base overhang region to allow restriction enzyme digestion. PCR was then performed on the phage clones and the amplified 500 bp fragment was isolated from a 1% agarose gel.

The amplified fragment was digested with Kpn1 and BgIII and then cloned into the Kpn1 and BgIII sites of the pGL3 basic vector (Promega) that contains the luciferase reporter gene and transformed into DH5 competent *E. coli* cells. Plasmid DNA was purified on Qiagen columns and sequenced by the dideoxynucleotide chain termination method using as primers corresponding to DNA sequences within the multiple cloning site but flanking the inserted DNA. The SCD promoter luciferase gene construct that was generated was designated as pSCD-500.

Isolation and Analysis of RNA—Total RNA was isolated from HepG2 cells using the acid guanidinium-phenol-chloroform extraction method. Twenty micrograms of total RNA was separated by 0.8% agarose/2.2 M formaldehyde gel electrophoresis and transferred onto nylon membrane. The membrane was hybridized with $^{32}$P-labeled human SCD cDNA probe generated by PCR as follows: pAL15 probe was used as control for equal loading.

Immunoblotting—Cell extracts were prepared from HepG2 cells that had been treated with the various fatty acids or cholesterol as described by Heinemann et al (17). The same amount of protein (60 μg) from each fraction was subjected to 10% SDS-polyacrylamide gel electrophoresis and transferred to Immobilon-P transfer membranes at 4° C. After blocking with 10% non-fat milk in TBS buffer (pH 8.0) plus 0.5% Tween at 4° C. overnight, the membrane was washed and incubated with rabbit anti-rat SCD as primary antibody (17) and goat anti-rabbit IgG-HRP conjugate as the secondary antibody. Visualization of the SCD protein was performed with ECL western blot detection kit.

Effect of Cholesterol, Polyunsaturated Fatty Acids and Arachidonic Acid on the Expression of hSCD1

Cell Culture and DNA transfections—HepG2 cells, were grown in Low Glucose DMEM supplemented with 10% Fetal Bovine Serum and 1% Penicillin/Streptomycin solution and maintained at 37 C, 5% $CO_2$ in a humidified incubator. Cells were passaged into 6 cm dishes to give 40-70% confluence in about 12-16 hours. Cells were then transfected with 5 μg plasmid DNA per plate of pSCD-500 or the Basic PGL3 reporter as well as well as the pRL-TK, internal controls (Promega) using the LT-1 transfection reagent (Pan Vera). After 48 hours, cells were rinsed with PBS and then treated in Williams' E Media, a fatty acid-free media, containing insulin, dexamethasone, and appropriate concentrations of albumin-conjugated fatty acids as indicated in figures and legends. Cells were also treated with ethanol alone (as control) or cholesterol (10 μg/mL) and 25-OH cholesterol (1 μg/mL) dissolved in ethanol. After an additional 24 h, extracts were prepared and assayed for luciferase activity. Non-transfected cells were used as the blank and Renilla Luciferase was used as an internal control. Cell extracts were assayed for protein according to Lowry, and all results were normalized to protein concentration as well as to renilla luciferase counts. Each experiment was repeated at least three times, and all data are expressed as means ±SEM.

Results:

The sequence of the amplified promoter region of the SCD1 gene is shown at SEQ ID. No. 1.

When compared to the mouse SCD1 promoter sequence, it was found that several functional regulatory sequences identified in the mouse SCD1 promoter are absolutely conserved at the nucleotide level and also with respect to their spacing within the proximal promoters of the two genes (FIG. 14). Both the TTAATA homology, the C/EBPα and NF-1 are in the same locations in both the mouse SCD1 and human promoters. Further upstream the sterol regulatory element (SRE) and the two CCMT box motifs that are found in the polyunsaturated fatty acid responsive element (PUFA-RE) of the mouse SCD1 and SCD2 promoters. The spacing of these elements is conserved in the three promoters.

Figure 15:
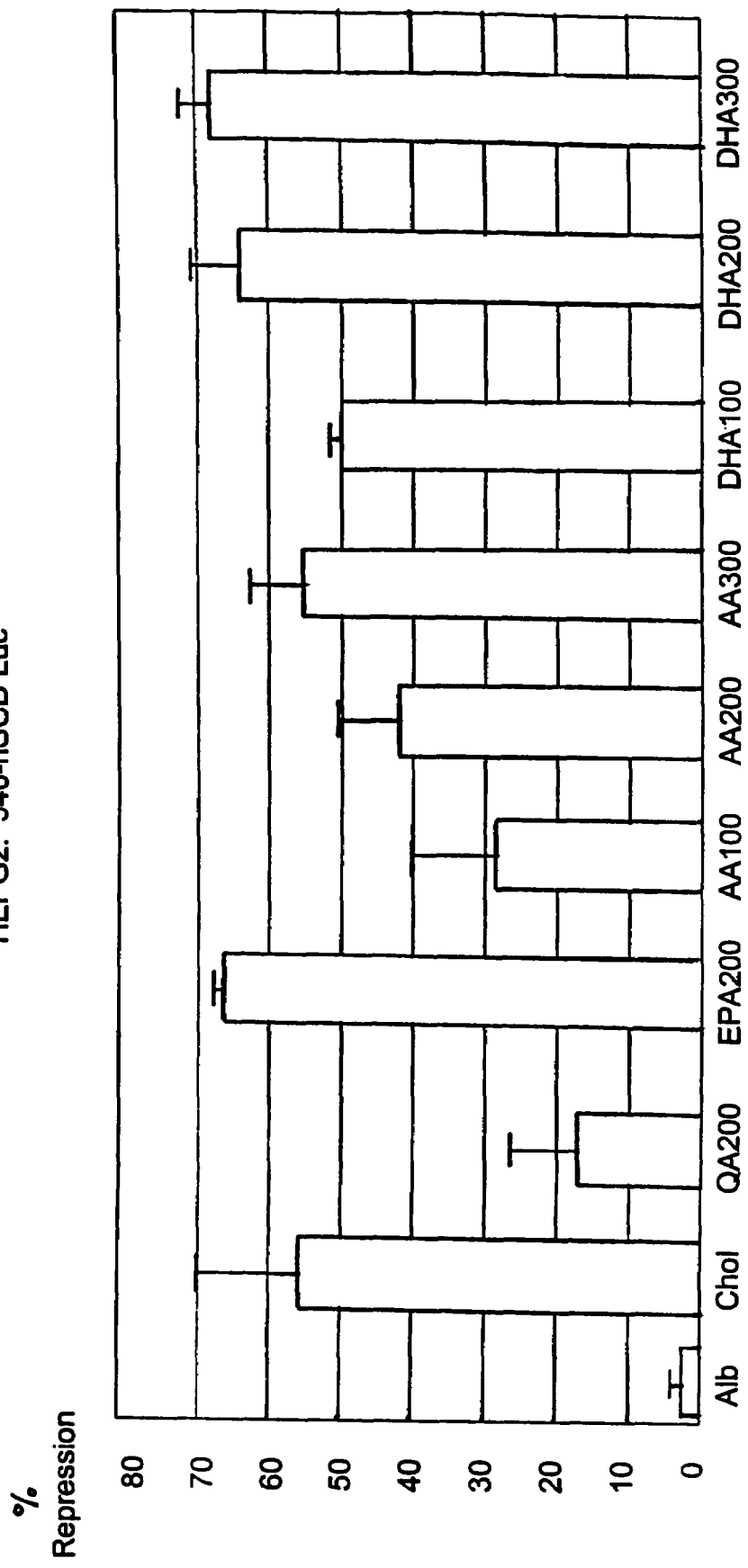
FIG. 15. Human HepG2 cells cultured and treated with a range of doses of arachidonic acid, DHA or 10 μg/ml cholesterol or EPA as indicated. Total mRNA was isolated and quantified.

We tested whether the human SCD gene expression was also repressed by cholesterol and polyunsaturated fatty acids. Human HepG2 cells were cultured and then treated with 100 μM arachidonic acid, DHA or 10 μg/ml cholesterol and 1 μg/ml of 25-hydroxycholesterol cholesterol as we have described previously. Total mRNA was isolated and subjected to northern blot analysis using a probe corresponding to the human cDNA and generated by the PCR method using primers based on published human SCD cDNA sequence. FIG. 15 shows that M, DHA and cholesterol decreased the human SCD mRNA expression in a dose dependent manner. The western blot of the protein extracts of the cells treated with PUFAs and cholesterol shows that PUFAs and cholesterol decreased the levels of the SCD protein as well (data not shown).

To assess the possible effect of SREBP binding on the activity of the human SCD promoter the human luciferase promoter construct was co-transfected in HepG2 cells together with an expression vector containing SREBP1a. After 72 h, extracts of the transfected cells were assayed for luciferase activity. Data were normalized to cell extract expressing the Renilla luciferase as an internal control. As shown in figure SREBP transactivates the promoter in a dose dependent manner giving rise to an increase up to 40-fold. This experiment shows that SREBP plays a role in regulating the human SCD gene.

Published reports indicated that the mature form of SREBP, in addition to activating the lipogenic genes, also mediates PUFA and cholesterol repression of lipogenic genes, including mouse SCD1. To observe the regulatory effects of mature SREBP-1a and PUFAs on the activity of SCD promoters, HepG2 hepatic cells were transiently co-transfected with 20 ng (per 6-cm dish) of plasmid DNA containing the human SCD promoter as described above but this time the transfections were carried out in the presence of cholesterol to inhibit the maturation of the endogenous SREBP and thus ensure that there was little mature form of the endogenous SREBP present in the cells. After transfection, the cells were then treated with, arachidonic acid, EPA and DHA as albumin complexes and luciferase activity was then assayed using a luminometer. If SREBP mediates PUFA repression of the human SCD gene, SCD promoter activity would not diminish upon treatment the transfected cells with PUFA. However addition of M, EPA or DHA continued to repress SCD promoter activity with only a slight attenuation (data not shown). Thus, SREBP maturation does not seem to exhibit the selectivity required to explain PUFA control of SCD gene transcription suggesting that PUFA may utilize a different protein in addition to the SREBP to repress human SCD gene transcription.

These results establish that hSCD1 is transcriptionally regulated by SREBP, NF-Y, C/EBPalpha, PUFA-RE and alternate proteins and transcription regulators. Each one of these proteins is therefore be an attractive drug screening target for identifying compounds which modulate SCD1 expression in a cell; and thereby being useful for treating the human diseases, disorders and conditions which are taught by the instant invention.

EXAMPLE 5

The SCD1 Knock-Out Displays Cutaneous and Ocular Abnormalities.

To investigate the physiological functions of SCD, we have generated SCD1 knock-out (SCD1−/−) mice. We found that the levels of C16:1 were dramatically decreased in the tissues of SCD1−/− mice whereas a dramatic decrease in C18:1 was noted only in liver where SCD1 alone and not SCD2 is normally expressed. In tissues such as the eyelid, adipose and skin where both SCD1 and SCD2 are expressed, 18:1was only slightly decreased. The monounsaturated fatty acids levels of the brain and eyeball which do not express SCD1 were unchanged. The liver and skin of the SCD−/− mice were deficient in cholesterol esters and triglycerides while the, eyelid in addition was deficient in eyelid-specific wax esters of long chain monounsaturated fatty acids mainly C20:1. In addition the eyelid of the SCD−/− mice had higher levels of free cholesterol. The SCD−/− mice exhibited cutaneous abnormalities with atrophic sebaceous gland and narrow eye fissure with atrophic meibomian glands which is similar to the dry eye syndrome in humans. These results indicate that SCD1 deficiency can affect the synthesis not only of monounsaturated fatty acids as components of tissue cholesterol ester and triglycerides but other lipids such as wax esters of the eyelid.

Gross Pathology and Histolgical Examination of SCD−/− Knock-Out Mice.

SCD−/− mice were healthy and fertile but they have cutaneous abnormalities. These abnormalities started around weaning age (3-4 weeks) with dry skin, fine epidermal scaling, and hair loss which became more severe with aging. In addition, the mice exhibited narrow eye fissures. Pathological examination of the skin and eyelids showed the wild-type mice had a prominent and well-differentiated sebaceous and meibomian glands (data not shown). On the other hand, skin and eyelid of SCD−/− appeared atrophic acinar cells in the sebaceous and meibomian glands (data not shown). No abnormalities were found in cornea and retina (data not shown).

SCD−/− Mice have Low Levels of Eyelid and Skin Neutral Lipids

Figure 16:
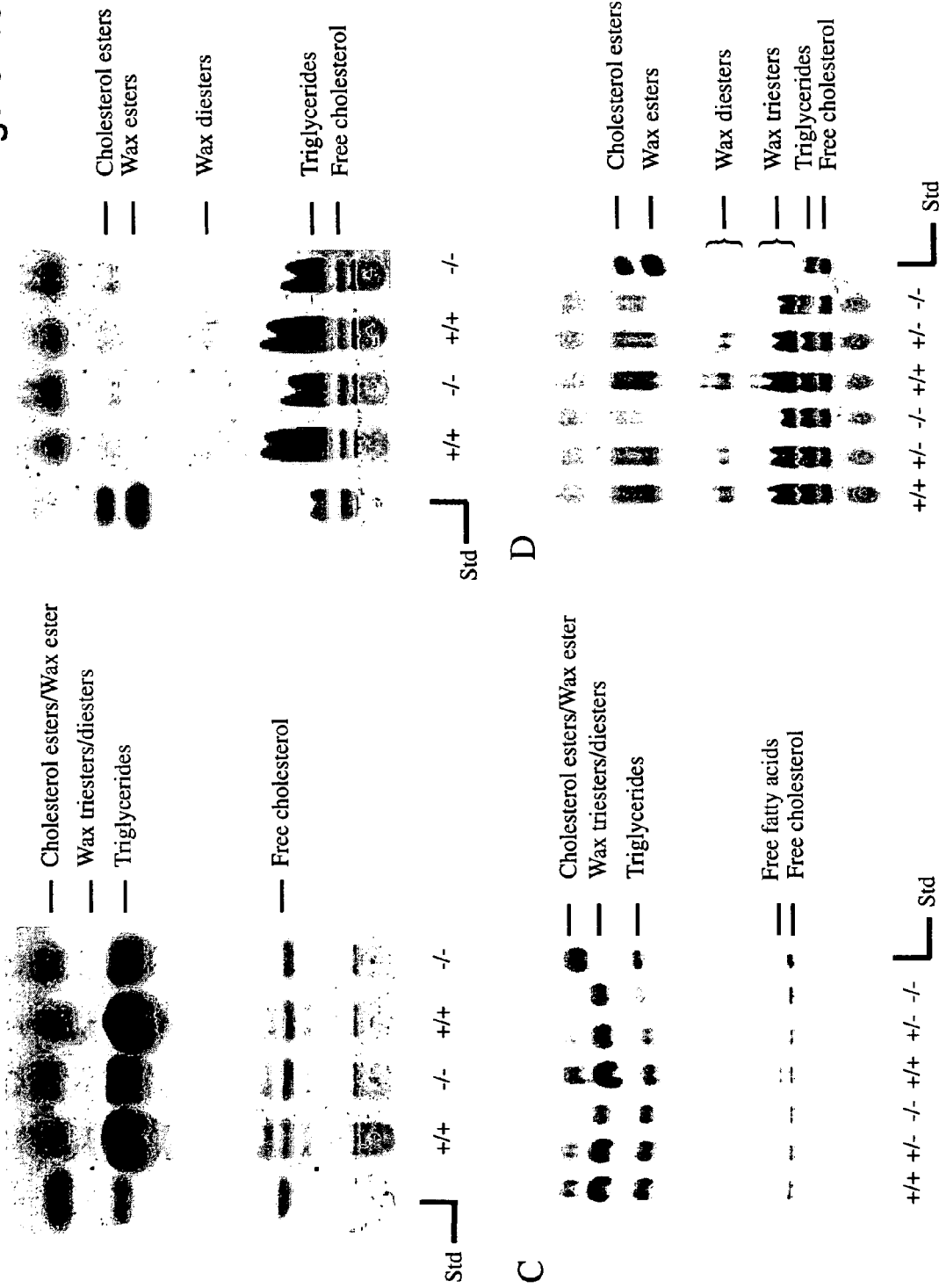
FIG. 16. TLC of lipid extracts from skin (A and B) and eyelids (C and D) of wild-type, heterozygotes and SCD−/− mice. Total lipids were extracted from eyelids of wild-type, heterozygotes and SCD−/− mice. Lipid extracts were pooled and analyzed by high performance TLC (HPTLC, A and C; hexane ether/ether/acetic acid=90:25:1, B and D; Benzene:hexane; 65:35). Same amounts of lipid extract (from 0.5 mg of eyelid) were subjected in each lane. Each lane represents lipids from eyelids of two mice.
Figure 17:
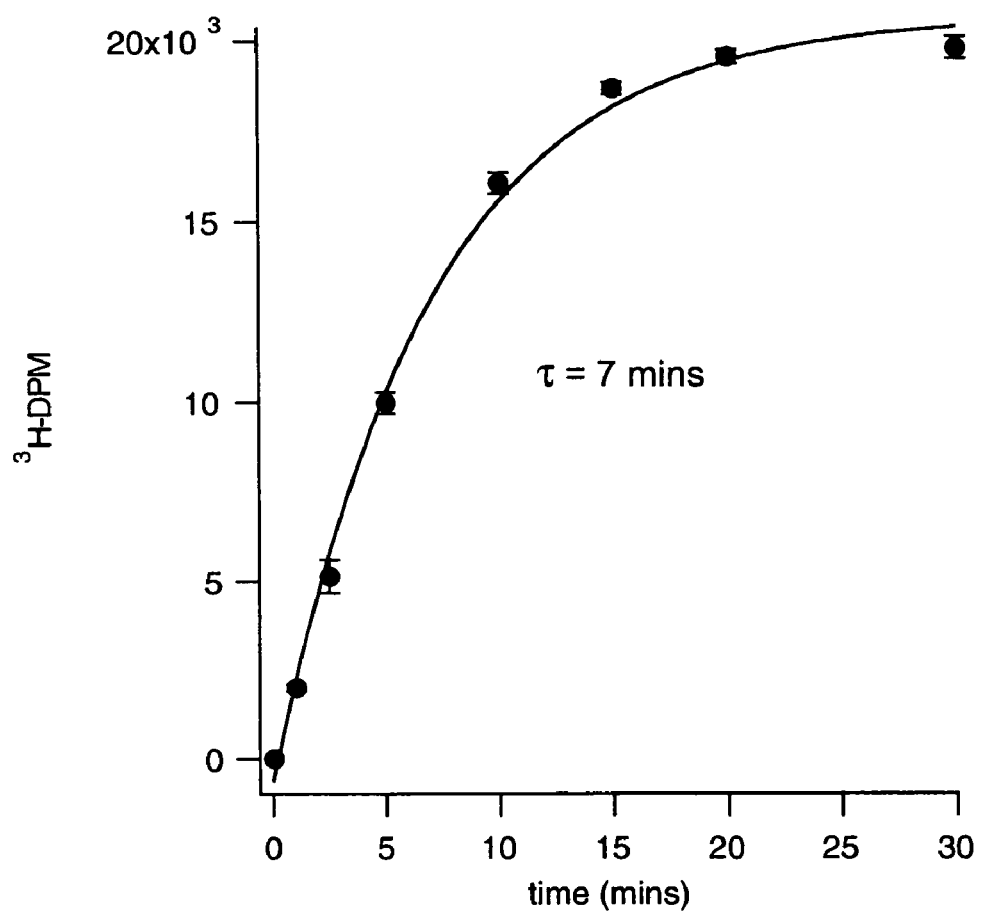
FIG. 17 shows an assay for SCD1 desaturase activity by quantifying transfer of 3H from stearate to water. The figure shows a time course of 3H-water production at room temperature. Microsomes from wild type livers were used for this experiment. A turnover number for SCD1 activity under these conditions was estimated at 2 nmol/min/mg protein, which is about half that observed at 37° C.
Figure 18:
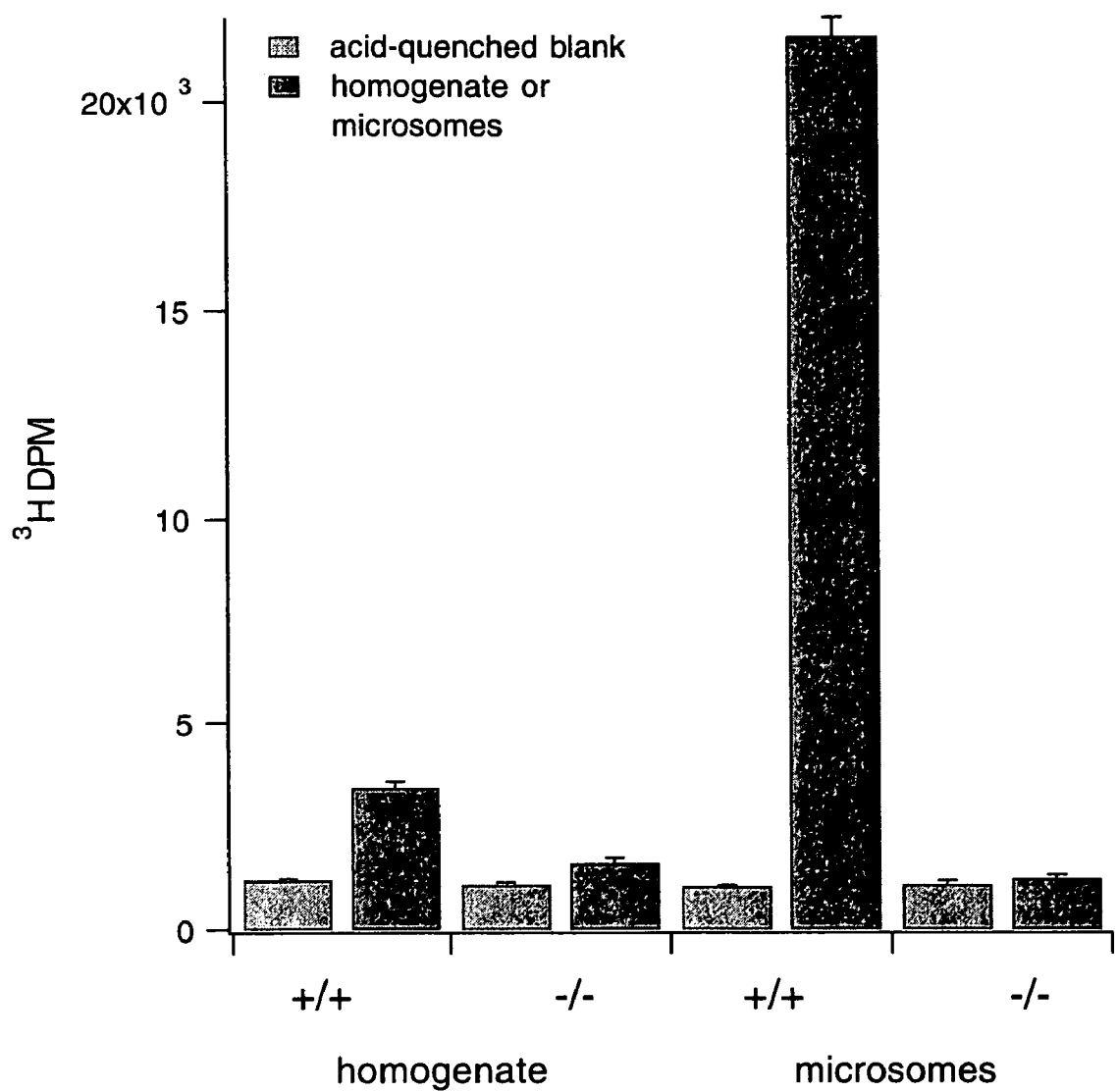
FIG. 18 shows validation that the assay monitors specifically SCD1-dependent desaturation of stearoyl-CoA. Livers were collected from wild type and SCD1 knockout mice following 3 days on a high carbohydrate fat-free diet (this induces SCD1 expression in liver by about 50-fold), homogenized and a portion used for microsome purification. 3H-water production was determined for 15 minutes at RT (room temperature) in both homogenate and microsome preparations at equivalent protein concentration, followed by quenching the reaction with acid and using charcoal to separate substrate from product. Quenching the sample with acid prior to the addition of substrate offers a blank, or control containing background radioactivity without any desaturation reaction. The figure shows that desaturation activity in microsomes is greatly enriched compared to the homogenate for wild type livers, while the microsomes from the −/− SCD1 knockout animal has very little activity. The "window", or SCD1-dependent desaturation in this assay, is a highly visible and significant 160-fold difference between wild type and SCD1 knockout microsomes.

We measured free cholesterol (FC) and cholesterol ester (CE), triglycerides and wax ester contents in the eyelid. Thin layer chromatography (TLC) of lipids extracted from eyelid of SCD1−/− mice demonstrated markedly reduced cholesterol ester and triglyceride and wax ester levels compared to the lipids extracted from eyelid of wild-type mice (FIG. 16A). Table 3 compares eyelid lipid contents between SCD−/− and wild type mice.

TABLE 3

| Genotype | +/+ | −/− |
|---|---|---|
| Cholesterol ester content (mg/g eyelid) | 18.1 ± 0.7 | 4.8 ± 0.3 |
| Free cholesterol content (mg/g eyelid) | 5.3 ± 0.5 | 8.4 ± 0.2 |
| Wax triester ((mg/g eyelid) | 36.8 ± 4.4 | 10.3 ± 0.8 |
| Triglycerides (mg/g eyelid) | 13.8 ± 0.6 | 5.5 ± 0.4 |

Each value of the table denotes the mean ±SD (n=4). All mice were 6 weeks old and fed a chow diet. Bold values of the −/− column denote a statistical significance (p<0.01) between the wild type and SCD−/− mice.

As shown in Table 3, and shows that the cholesterol ester content in eyelid and skin of SCD1−/− mice was decreased by 74%, while free cholesterol increased by 1.75-fold. There was a reduction in the CE and triglyceride level in the liver of the SCD−/− as well but there was no difference in free cholesterol content in liver (data not shown). The triglyceride and wax ester contents in the eyelid of the SCD−/− mice decreased by 60% and 75%, respectively.

FIG. 16B shows use of a different solvent according to Nicolaids et al (Nicolaides, N., and Santos, E. C. (1985). The di- and triesters of the lipids of steer and human meibomian glands. Lipids 20, 454-67) consisting of hexane/benzene (45:65) was used to resolve the different wax esters shows that the triester is the major wax ester. These triesters as well as the diesters were decreased by 72% in the SCD−/− mice. The eyelid of wax triester content decreased by 72% in the SCD−/− mice. Similar to eyelid, cholesterol ester and triglyceride contents in the skin of SCD−/− mice decreased by 43% and 53%, respectively while free cholesterol increased by 1.9-fold (Table 3, and FIGS. 16A and B). Finally, the absolute monounsaturated fatty acid content in each fraction was dramatically reduced in the SCD1−/− mice with corresponding increases in the saturated fatty acids (data not shown).

Dietary 18:1 Did Not Restore Abnormalities of Skin and Eyelid in SCD−/− Mice

Oleate is one of the most abundant fatty acids in the diet. The cellular monounsaturated fatty acids used for cholesterol ester and triglyceride synthesis, could be synthesized either de novo by Fatty Acid Synthase and SCD or by incorporation of exogenous oleate indirectly from the diet. To determine whether dietary oleate could substitute for the endogenously synthesized oleate and restore the hair, skin and eye abnormalities of the SCD−/− mice, we supplemented the semi-purified mouse diets with high levels of 18:1n-9 (50% of total fat) as triolein, and then fed these diets to SCD−/− mice for 2 weeks. However, these abnormalities were not restored by these diets which contained high monounsaturated fatty acids. This suggests that SCD1 specific inhibitors would act to reduce TG levels regardless of diet. Instead, cholesterol ester, wax ester and triglyceride levels in the eyelids of SCD−/− mice fed with high 18:1n-9 were still lower than those of SCD+/+ mice (data not shown), suggesting that endogenously synthesized monounsaturated fatty acids are required for the synthesis of the cholesterol esters triglycerides and wax esters of mebum.

In the present study, we have established SCD1 null mice and have shown that SCD deficiency caused substrate-selective and tissue-selective expression. The level of palmitoleate in SCD−/− mice is decreased by greater than 50% in all tissues including liver, which expressed SCD1 in wild-type mice. On the other hand, the alternations of oleate level were tissue-specific.

Similar to asebia mice which have a spontaneous mutation of SCD1, SCD−/− mice exhibited abnormalities of hair growth, skin, and eye with complete penetrance. These phenotypes were noticeable from weaning age. Histological examination of the skin and eye lid showed that the atropic sebaceous gland in the skin and meibomian gland in the border of eyelid where SCD1 is abundantly expressed, lacked sebaceous and meibomian secreted lipids, the so-called, sebum and mebum, respectively. In fact, we found that neutral lipids including triglyceride, several kinds of wax esters and cholesterol ester which are known to be components of sebum and mebum, were markedly reduced in the eyelid and also from the epidermis (data not shown) of the SCD−/− mice.

Chronic blepharitis similar to the eye lid abnormalities we have described in the SCD−/− mice, is one of the most common frustrating disease in humans. Shine and McCulley (Shine, W. E., and McCulley, J. P. (1998). Keratoconjunctivitis sicca associated with meibomian secretion polar lipid abnormality. Arch Ophthalmol 116, 849-52) have reported that chronic blephatitis may be due to lipid abnormalities in mebum. The nature of these lipid abnormalities were not characterized in detail. They however, found that mebum from patients with meibomian keratoconjunctivitis have decreased levels of oleic acid, a major product of SCD whereas that from patients with meibomian seborrhea have increased levels of 18:1. These observations, together with our present study, suggest that the alternation of SCD activity can be implicated in chronic blepharitis. Thus, the SCD may become a potential target for the development of therapeutic and preventive drugs for the treatment of eye diseases.

Promoter Sequence of Human Stearoyl-CoA Desaturase 1

SEQ ID No. 1
```
ggtccccgcc ccttccagag agaaagctcc cgacgcggga tgccgggcag aggcccagcg gcgggtggaa gagaagctga gaaggagaaa cagaggggag ggggagcgag gagctggcgg cagagggaac agcagattgc gccgagccaa tggcaacggc aggacgaggt ggcaccaaat tcccttcggc caatgacgag ccggagttta cagaagcctc attagcattt ccccagaggc aggggcaggg gcagaggccg ggtggtgtgg tgtcggtgtc ggcagcatcc ccggcgccct gctgcggtcg ccgcgagcct cggcctctgt ctcctccccc tcccgccctt acctccacgc gggaccgccc gcgccagtca actcctcgca ctttgcccct gcttggcagc ggataaaagg gggctgagga aataccggac acggtcaccc gttgccagct ctagccttta aattcccggc tcggggacct ccacgcaccg cggctagcgc cgacaaccag ctagcgtgca aggcgccgcg gctcagcgcg taccggcggg cttcgaaacc gcagtcctcc ggcgacccg aactccgctc cggagcctca gccccct
```

REFERENCE LIST

1. Mihara, K. Structure and regulation of rat liver microsomal stearoyl-CoA desaturase gene. *J. Biochem.* (Tokyo) 108, 1022-1029 (1990).
2. Thiede, M. A. & Strittmatter, P. The induction and characterization of rat liver stearyl-CoA desaturase mRNA. *J. Biol. Chem.* 260, 14459-14463 (1985).
3. Kaestner, K. H., Ntambi, J. M., Kelly, T. J., Jr. & Lane, M. D. Differentiation-induced gene expression in 3T3-L1 preadipocytes. A second differentially expressed gene encoding stearoyl-CoA desaturase. *J. Biol. Chem.* 264, 14755-14761 (1989).
4. Ntambi, J. M. et al. Differentiation-induced gene expression in 3T3-L1 preadipocytes. Characterization of a differentially expressed gene encoding stearoyl-CoA desaturase. *J. Biol. Chem.* 263, 17291-17300 (1988).
5. Zhang, L., Ge, L., Parimoo, S., Stenn, K. & Prouty, S. M. Human stearoyl-CoA desaturase: alternative transcripts generated from a single gene by usage of tandem polyadenylation sites. *Biochem. J.* 340 (Pt 1), 255-264 (1999).
6. Zheng, Y. et al. Scd1 is expressed in sebaceous glands and is disrupted in the asebia mouse [letter]. *Nat. Genet.* 23, 268-270 (1999).
7. Sundberg, J. P. et al. Asebia-2J (Scd1(ab2J)): a new allele and a model for scarring alopecia. *Am. J. Pathol.* 156, 2067-2075 (2000).
8. Miyazaki, M., Kim, Y. C., Keller, M. P., Attie, A. D. & Ntambi, J. M. The biosynthesis of hepatic cholesterol esters and triglycerides is impaired in mice with a disruption of the gene for stearoyl-CoA desaturase 1. *J. Biol. Chem.* (2000).
9. Spector, A. A. & Yorek, M. A. Membrane lipid composition and cellular function. *J. Lipid Res.* 26, 1015-1035 (1985).
10. Enser, M. & Roberts, J. L. The regulation of hepatic stearoyl-coenzyme A desaturase in obese-hyperglycaemic (ob/ob) mice by food intake and the fatty acid composition of the diet. *Biochem. J.* 206, 561-570 (1982).
11. Enser, M. The role of insulin in the regulation of stearic acid desaturase activity in liver and adipose tissue from obese-hyperglycaemic (ob/ob) and lean mice. *Biochem. J.* 180, 551-558 (1979).
12. Enser, M. Desaturation of stearic acid by liver and adipose tissue from obese-hyperglycaemic mice (ob/ob). *Biochem. J.* 148, 551-555 (1975).
13. Jones, B. H. et al. Adipose tissue stearoyl-CoA desaturase mRNA is increased by obesity and decreased by polyunsaturated fatty acids. *Am. J. Physiol* 271, E44-E49 (1996).
14. Kim, Y. C., Gomez, F. E., Fox, B. G. & Ntambi, J. M. Differential regulation of the stearoyl-CoA desaturase genes by thiazolidinediones in 3T3-L1 adipocytes. *J. Lipid Res.* 41, 1310-1316 (2000).
15. Li, J. et al. Partial characterization of a cDNA for human stearoyl-CoA desaturase and changes in its mRNA expression in some normal and malignant tissues. *Int. J. Cancer* 57, 348-352 (1994).
16. Wood, C. B. et al. Reduction in the stearic to oleic acid ratio in human malignant liver neoplasms. *Eur. J. Surg. Oncol.* 11, 347-348 (1985).
17. Habib, N. A. et al. Stearic acid and carcinogenesis. *Br. J. Cancer* 56, 455-458 (1987).
18. Tronstad, K. J., Berge, K., Bjerkvig, R., Flatmark, T. & Berge, R. K. Metabolic effects of 3-thia fatty acid in cancer cells. *Adv. Exp. Med. Biol.* 466, 201-204 (1999).
19. DeWille, J. W. & Farmer, S. J. Postnatal dietary fat influences mRNAS involved in myelination. *Dev. Neurosci.* 14, 61-68 (1992).
20. Garbay, B. et al. Regulation of oleoyl-CoA synthesis in the peripheral nervous system: demonstration of a link with myelin synthesis. *J. Neurochem.* 71, 1719-1726 (1998).

21. Marcelo, C. L., Duell, E. A., Rhodes, L. M. & Dunham, W. R. In vitro model of essential fatty acid deficiency. *J. Invest Dermatol.* 99, 703-708 (1992).
22. Tebbey, P. W. & Buttke, T. M. Stearoyl-CoA desaturase gene expression in lymphocytes [published erratum appears in Biochem Biophys Res Commun Sep. 16, 1992; 187(2):1201]. *Biochem. Biophys. Res. Commun.* 186, 531-536 (1992).
23. Tebbey, P. W. & Buttke, T. M. Molecular basis for the immunosuppressive action of stearic acid on T cells [published erratum appears in Immunology October 1990;71(2):306]. *Immunology* 70, 379-386 (1990).
24. Stampfer et al. A prospective study of cholesterol, apolipoproteins, and the risk of myocardial infraction. *N. Engl. J. Med.* 325, 373-381 (1991).
25. Schmidt et al. Clustering of dyslipidemia, hyperuricemia, diabetes, and hypertension and its association with fasting insulin and central and overall obesity in a general population. Atherosclerosis Risk in Communities Study Investigators *Metabolism* 45 (6):699-706 (1996).
26. Park et al. Inhibition of hepatic stearoyl-CoA desaturase activity by trans-10, cis-12 conjugated linoleic acid and its derivatives. Biochim Biophys Acta. 1486(2-3):285-92 (2000).
27. Choi et al. The trans-10, cis-12 isomer of conjugated linoleic acid downregulates stearoyl-CoA desaturase 1 gene expression in 3T3-L1 adipocytes. *J Nutr.* 130(8): 19204 (2000)

What is claimed is:

1. A method for identifying an agent that modulates plasma triglyceride levels in a mammal comprising administering to a mammal an agent that has Stearoyl-coenzyme A-desaturase (SCD1)-modulating activity in an in vitro microsome-based assay, wherein said agent tested in said assay does not comprise coenzyme A and does not substantially inhibit Δ-5 or Δ-6 -desaturase and detecting a change in plasma triglyceride level in said mammal as a result of said administering thereby identifying said agent as a plasma triglyceride modulating agent.

2. A method for identifying an agent that modulates plasma triglyceride levels in a mammal comprising administering to a mammal an agent that has Stearoyl-coenzyme A-desaturase (SCD1)-modulating activity in an in vitro cell-based assay wherein said agent tested in said assay does not comprise coenzyme A and does not substantially inhibit Δ-5 or Δ-6 desaturase and detecting a change in plasma triglyceride level in said mammal as a result of said administering thereby identifying said agent as a plasma triglyceride modulating agent.

3. The method of claim 1, wherein said agent that has SCD1-modulating activity was first identified as having SCD1-modulating activity using said in vitro microsome-based assay.

4. The method of claim 1, wherein said plasma triglyceride modulating activity is a decrease in plasma triglyceride level.

5. The method of claim 1, wherein said mammal is a human.

6. The method of claim 2, wherein said agent that has SCD1-modulating activity was first identified as having SCD1- modulating activity using said in vitro cell-based assay.

7. The method of claim 2, wherein said plasma triglyceride modulating activity is a decrease in plasma triglyceride level.

8. The method of claim 2, wherein said mammal is a human.

* * * * *

UNITED STATES PATENT AND TRADEMARK OFFICE
CERTIFICATE OF CORRECTION

PATENT NO. : 7,696,151 B2
APPLICATION NO. : 11/178808
DATED : April 13, 2010
INVENTOR(S) : Michael R. Hayden Page 1 of 2

It is certified that error appears in the above-identified patent and that said Letters Patent is hereby corrected as shown below:

In the Specification:

At column 5, line 28, delete "r2" and insert -- $r^2$ --

At column 5, line 29, delete "r2" and insert -- $r^2$ --

At column 5, line 54, delete "3H" and insert -- $^3H$ --

At column 5, line 55, delete "3H" and insert -- $^3H$ --

At column 14, line 63, delete "3H" and insert -- $^3H$ --

At column 36, line 20, delete "α-$^3$ $^2$P]dCTP" and insert -- [α-$^{32}$P]dCTP --

At column 37, line 62, delete "CHCl3" and insert -- $CHCl_3$ --

At column 37, line 64, delete "N2" and insert -- $N_2$ --

At column 38, line 8, delete "?9?16:1?, 16:0?, ?9?18:" and insert -- 9 16:1, 16:0, 9 18: --

At column 39, line 25, delete "r2" and insert -- $r^2$ --

At column 39, line 26, delete "r2" and insert -- $r^2$ --

At column 39, line 27, delete "r2" and insert -- $r^2$ --

At column 40, line 37, delete "CCMT" and insert -- CCAAT --

Signed and Sealed this
Twenty-fifth Day of January, 2011

David J. Kappos
*Director of the United States Patent and Trademark Office*

CERTIFICATE OF CORRECTION (continued)
U.S. Pat. No. 7,696,151 B2

In the Specification:

At column 41, line 9, delete "NNNNGGTACCTTNNGAAAAGAACAGCGCCC" and insert -- NNNN<u>GGTACC</u>TTNNGAAAAGAACAGCGCCC --

At column 41, line 14, delete "NNNNAGATCTGTGCGTGGAGGTCCCCG" and insert -- NNNN<u>AGATCT</u>GTGCGTGGAGGTCCCCG --

At column 42, line 21, delete "CCMT" and insert -- CCAAT --